United States Patent
Kim

(10) Patent No.: US 11,773,381 B2
(45) Date of Patent: Oct. 3, 2023

(54) CELL PENETRATING PEPTIDE, CONJUGATE COMPRISING SAME, AND COMPOSITION COMPRISING CONJUGATE

(71) Applicants: GemVax & KAEL CO., LTD., Daejeon (KR); Sang Jae KIM, Seoul (KR)

(72) Inventor: Sang Jae Kim, Seoul (KR)

(73) Assignee: Gem Vax & KAEL CO., LTD., Daejeon (KR)

( * ) Notice: Subject to any disclaimer, the term of this patent is extended or adjusted under 35 U.S.C. 154(b) by 348 days.

(21) Appl. No.: 17/032,781

(22) Filed: Sep. 25, 2020

(65) Prior Publication Data

US 2021/0062167 A1 Mar. 4, 2021

Related U.S. Application Data

(62) Division of application No. 15/869,518, filed on Jan. 12, 2018, now Pat. No. 10,822,595, which is a division of application No. 14/429,637, filed as application No. PCT/KR2013/008438 on Sep. 17, 2013, now Pat. No. 9,902,945.

(30) Foreign Application Priority Data

| Sep. 19, 2012 | (KR) | 10-2012-0104144 |
| Sep. 19, 2012 | (KR) | 10-2012-0104173 |
| Sep. 28, 2012 | (KR) | 10-2012-0109207 |
| Sep. 28, 2012 | (KR) | 10-2012-0109216 |
| Feb. 18, 2013 | (KR) | 10-2013-0017169 |

(51) Int. Cl.

| C07K 14/00 | (2006.01) |
| C12N 9/12 | (2006.01) |
| A23L 33/18 | (2016.01) |
| A61K 49/00 | (2006.01) |
| C07K 7/08 | (2006.01) |
| A61K 8/64 | (2006.01) |
| A61K 8/66 | (2006.01) |
| A61Q 19/00 | (2006.01) |
| G01N 33/58 | (2006.01) |
| A61K 47/64 | (2017.01) |
| A61K 38/00 | (2006.01) |

(52) U.S. Cl.
CPC ............ *C12N 9/1276* (2013.01); *A23L 33/18* (2016.08); *A61K 8/64* (2013.01); *A61K 8/66* (2013.01); *A61K 47/64* (2017.08); *A61K 49/0002* (2013.01); *A61K 49/0043* (2013.01); *A61K 49/0056* (2013.01); *A61Q 19/00* (2013.01); *C07K 7/08* (2013.01); *C07K 14/00* (2013.01); *G01N 33/582* (2013.01); *A23V 2002/00* (2013.01); *A61K 38/00* (2013.01); *A61K 2800/10* (2013.01); *A61K 2800/57* (2013.01); *C07K 2319/10* (2013.01); *G01N 2458/30* (2013.01)

(58) Field of Classification Search
CPC ................................ A61K 47/64; C07K 14/00
See application file for complete search history.

(56) References Cited

U.S. PATENT DOCUMENTS

| 6,166,178 A * | 12/2000 | Cech ............ C12N 9/1241 |
| | | 530/828 |
| 7,030,211 B1 | 4/2006 | Gaudernack et al. |
| 7,078,491 B1 | 7/2006 | Harrington |
| 7,195,911 B2 | 3/2007 | Cech et al. |
| 7,794,723 B2 | 9/2010 | Gaudernack et al. |
| 8,252,282 B2 | 8/2012 | Santos |
| 9,527,888 B2 | 12/2016 | Kim |
| 9,572,900 B2 | 2/2017 | Kim |
| 9,631,184 B2 | 4/2017 | Kim |
| 9,757,473 B2 | 9/2017 | Kim |
| 9,902,945 B2 | 2/2018 | Kim |
| 10,383,928 B2 * | 8/2019 | Gaudernack ... C12Y 207/07049 |
| 2010/0003229 A1 | 1/2010 | Santos |
| 2011/0318380 A1 | 12/2011 | Brix et al. |
| 2015/0125438 A1 | 5/2015 | Kim |
| 2016/0120966 A1 | 5/2016 | Kim |
| 2017/0081376 A1 | 3/2017 | Kim |
| 2017/0112941 A1 | 4/2017 | Panitch et al. |
| 2017/0112942 A1 | 4/2017 | Kim |

(Continued)

FOREIGN PATENT DOCUMENTS

| JP | 2002520293 A | 7/2002 |
| KR | 20100085527 A | 7/2010 |

(Continued)

OTHER PUBLICATIONS

Cho, Y.J., "A Godsend About to Arrive," GemVax (082270), Hana Daetoo Securities Co., Ltd., Company Report, 8 pages (Sep. 10, 2012).

Fonesca, S.B., et al., "Recent advances in the use of cell-penetrating peptides for medical and biological applications," *Adv. Drug Deliv. Rev.* 61:953-964, Elsevier B.V., Netherlands (2009).

Heitz, F., et al., "Twenty years of cell-penetrating peptides: from molecular mechanisms to therapeutics," *Br. J. Pharmacal.* 757:195-206, The British Pharmacological Society, United Kingdom (2009).

(Continued)

*Primary Examiner* — Karen Cochrane Carlson
(74) *Attorney, Agent, or Firm* — Clark & Elbing LLP; Susan M. Michaud

(57) ABSTRACT

The present invention relates to a conjugate of cell penetrating peptide and an active ingredient; and its use. Specifically, a conjugate including a cell penetrating peptide which is a peptide comprising any one amino acid sequence of SEQ ID NO: 1 to SEQ ID NO: 156, a fragment of any one sequence of SEQ ID NO: 1 to SEQ ID NO: 156, or a peptide having above 80% homology with the above-mentioned sequence; and a composition comprising the same are disclosed.

21 Claims, 35 Drawing Sheets

Specification includes a Sequence Listing.

(56) References Cited

U.S. PATENT DOCUMENTS

2017/0275603 A1  9/2017  Kim
2017/0327802 A1  11/2017  Kim

FOREIGN PATENT DOCUMENTS

| WO | WO-0002581 A1 | 1/2000 |
| WO | WO-2005107818 A2 | 11/2005 |
| WO | WO-2009025871 A1 | 2/2009 |
| WO | WO-2011101173 A1 | 8/2011 |

OTHER PUBLICATIONS

Lee, S-A., et al., "Heat shock protein-mediated cell penetration and cystosolic delivery of macromolecules by a telomerase-derived peptide vaccine," *Biomaterials* 34:7945-7505, Elsevier Ltd., United Kingdom (2013).

Luft, R., et al., "A case of severe hypermetabolism of nonthyroid origin with a defect in the maintenance of mitochondrial respiratory control: a correlated clinical, biochemical, and morphological study," *J. Clin. Invest.* 41(9):1776-1804, American Society for Clinical Investigation, United States (1962),.

Smith, D.B. and Johnson, K.S., "Single-step purification of polypeptides expressed in *Escherichia coli* as fusions with glutathione S-transferase," *Gene* 67:31-40, Elsevier Science Publishers B.V., Netherlands (1988).

International Search Report for International Patent Application No. PCT/KR2013/008438, Korean Intellectual Property Office, Republic of Korea, dated Dec. 23, 2013, 3 pages.

International Preliminary Report on Patentability for International Patent Application No. PCT/KR2013/008438, The International Bureau of WIPO, Switzerland, dated Mar. 24, 2015, 6 pages.

Written Opinion for International Patent Application No. PCT/KR2013/008438, Korean Intellectual Property Office, Republic of Korea, dated Dec. 23, 2013, 5 pages.

Santos, J.H., et al., "Mitochondrial hTERT exacerbates free-radical-mediated mtDNA damage," *Aging Cell* 3:399-411, Wiley-Blackwell Publishing Ltd., United Kingdom (Jul. 2004).

Non-Final Office Action dated Apr. 12, 2016, in United States U.S. Appl. No. 14/400,322, Kim, S.J., et al., filed Nov. 10, 2014.

Final Office Action dated Sep. 7, 2016, in United States U.S. Appl. No. 14/400,322, Kim, S.J., et al., filed Nov. 10, 2014.

Final Office Action dated Apr. 13, 2017, in U.S. Appl. No. 14/400,322, Kim, S.J., et al., filed Nov. 10, 2014.

Advisory Action dated Jul. 24, 2017, in U.S. Appl. No. 14/400,322, Kim, S.J., et al., filed Nov. 10, 2014.

Non-Final Office Action dated Apr. 25, 2016, in U.S. Appl. No. 14/400,321, Kim, S.J., et al., filed Nov. 10, 2014.

Non-Final Office Action dated Mar. 26, 2018, in U.S. Appl. No. 15/354,139, Kim, S.J., et al., filed Nov. 17, 2016.

Non-Final Office Action dated Nov. 2, 2016, in U.S. Appl. No. 14/429,637, Kim, S.J., et al., filed Mar. 19, 2015.

Final Office Action dated Mar. 29, 2017, in U.S. Appl. No. 14/429,637, Kim, S.J., et al., filed Mar. 19, 2015.

Advisory Action dated Jul. 5, 2017, in U.S. Appl. No. 14/429,637, Kim, S.J., et al., filed Mar. 19, 2015.

Horwich, A.L., et al., "A leader peptide is sufficient to direct mitochondrial import of a chimeric protein," *EMBO J.* 4(5):1129-1135, Wiley-Blackwell, Germany (1985).

Armstrong, J.S., "Mitochondrial Medicine: Pharmacological Targeting of Mitochondria in Disease," *British Journal of Pharmacology* 151:1154-1165, Nature Publishing Group, United Kingdom (2007).

Lopez, M., et al., "Mitochondia-targeted Nitroxides as MRI Contrast Agents and Chemotherapeutics," *Free Radical Biology & Medicine* 45(Suppl. 1): S55, Abstract 131, Elsevier, Netherlands (2008).

Salaklang, J., et al., "Superparamagnetic nanoparticles as a power systems biology characterization tool in the physiological context," *Angewandte Chemie Int. Ed.* 47:7857-7860, Wiley Verlag, Germany (2008).

Non-Final Office Action dated Apr. 22, 2016, in U.S. Appl. No. 14/429,644, Kim, S.J., et al., filed Mar. 19, 2015.

Du, C., et al., "Conformational and topological requirements of cell-permeable peptide function," *J. Peptide Res.* 51(3):235-43, John Wiley & Sons, United States (1998).

Schwarze, S.R., et al. "In vivo protein transduction: delivery of a biologically active protein into the mouse," *Science* 285(5433):1569-72, American Association for the Advancement of Science, United States (1999).

Ge, D., and Levicky, R., "A comparison of five bioconjugatable ferrocenes for labeling of biomolecules," *Chem. Comm.* 46:7190-7192, Royal Society of Chemistry, United Kingdom (2010).

Kalnins, A., et al. "Sequence of the lacZ gene of *Escherichia coli*," *The EMBO Journal* 2(4):593-597, Wiley-Blackwell, Germany (1983).

Non-Final Office Action dated Dec. 22, 2016, in U.S. Appl. No. 14/903,827, Kim, S.J., et al., filed Jan. 8, 2016.

Godet, Y., et al., "Analysis of Spontaneous Tumor-Specific CD4 T-cell Immunity in Lung Cancer Using Promiscuous HLA-DR Telomerase-Derived Epitopes: Potential Synergistic Effect with Chemotherapy Response," *Clinical Cancer Research* 78(10):2943-2953, American Association for Cancer Research Inc., United States (2012).

\* cited by examiner

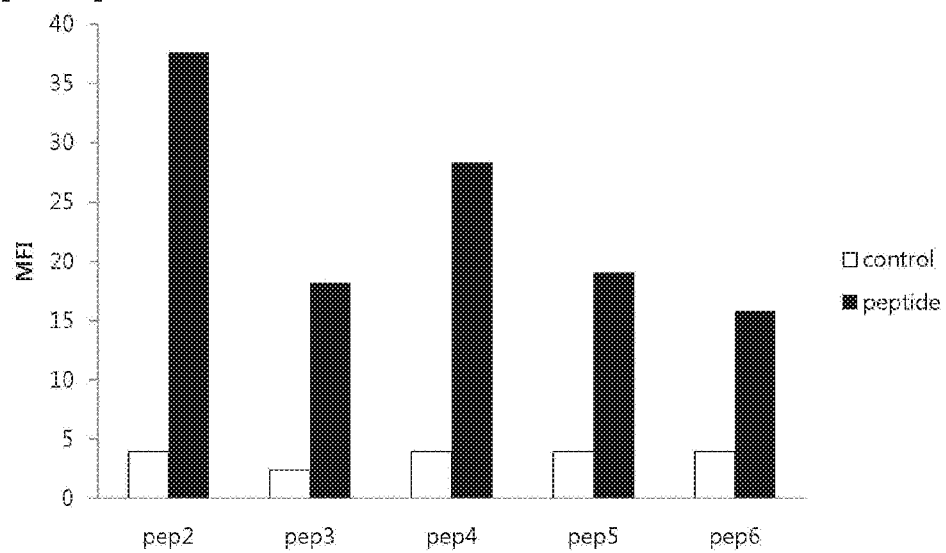
[FIG. 1]
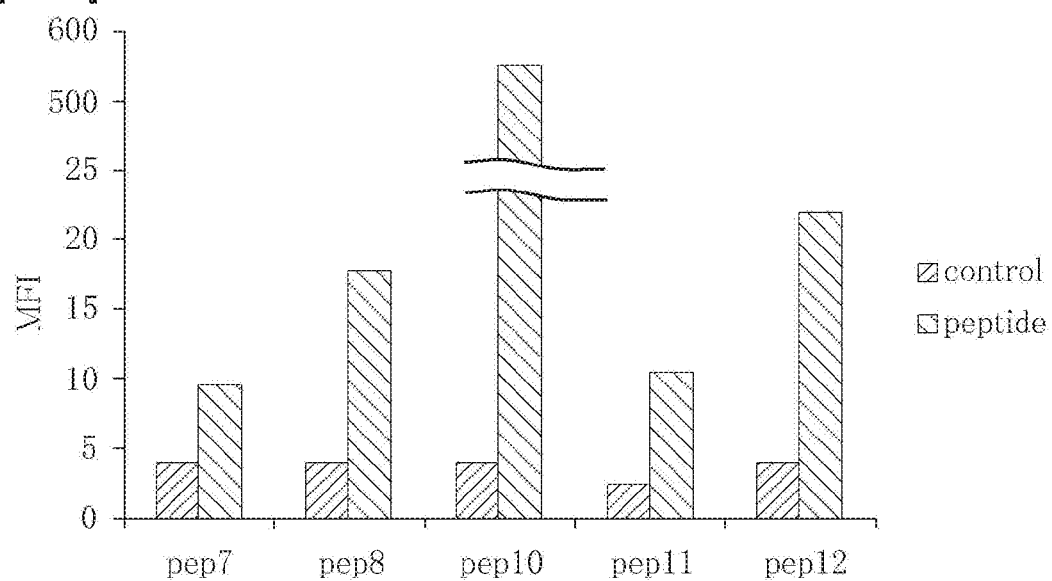
[FIG. 2]

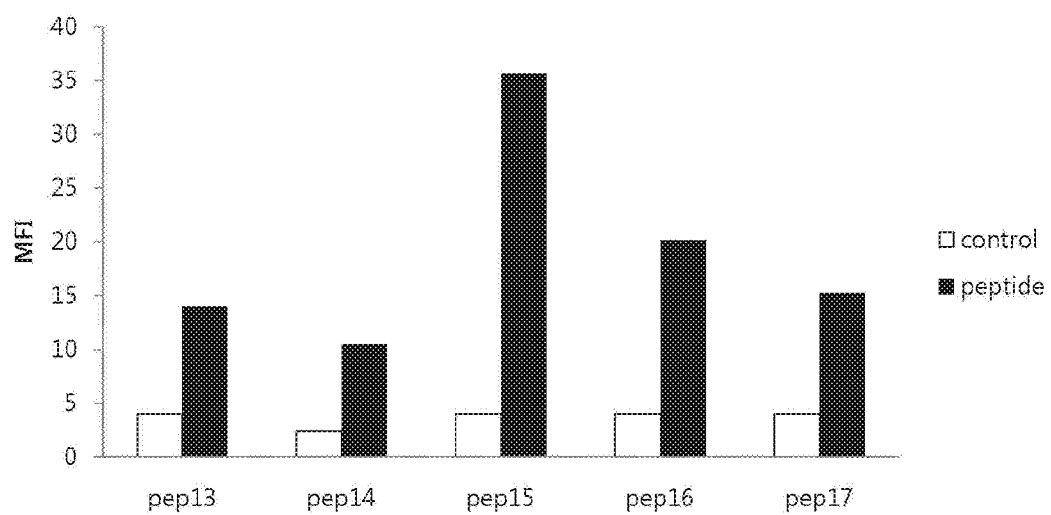
[FIG. 3]
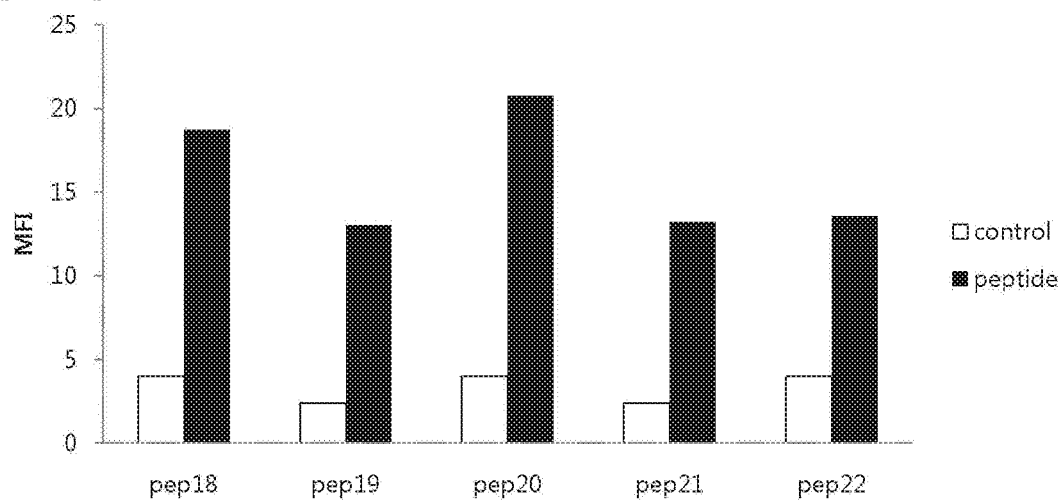
[FIG. 4]

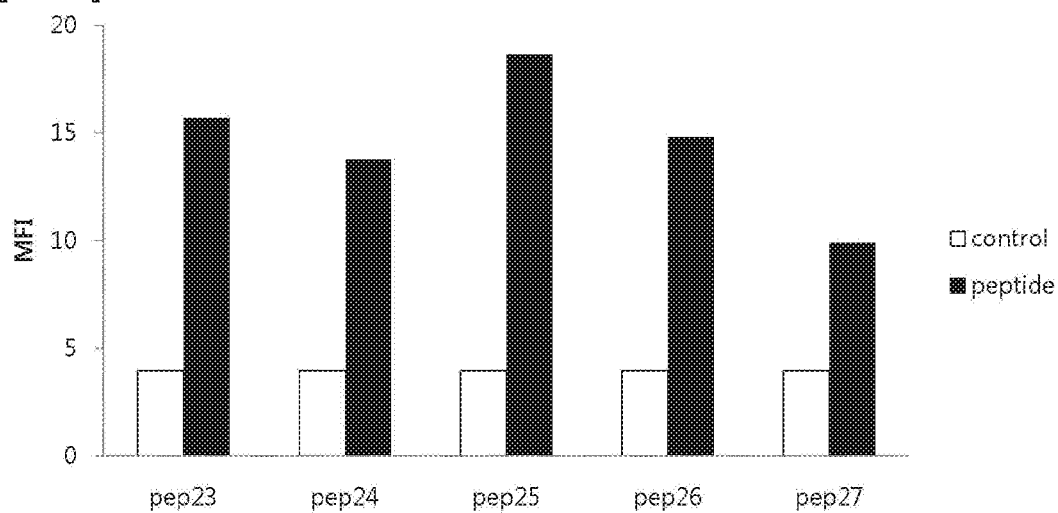
[FIG. 5]
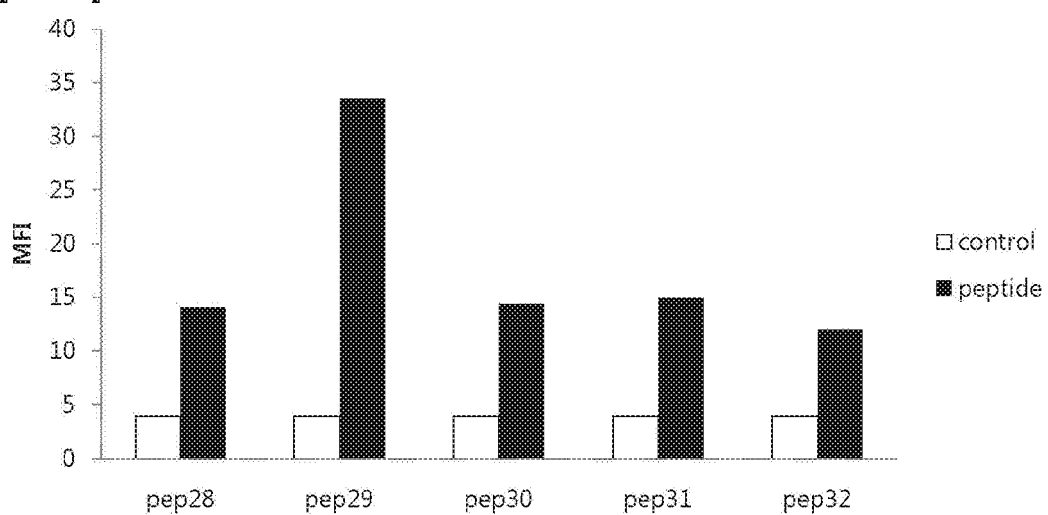
[FIG. 6]

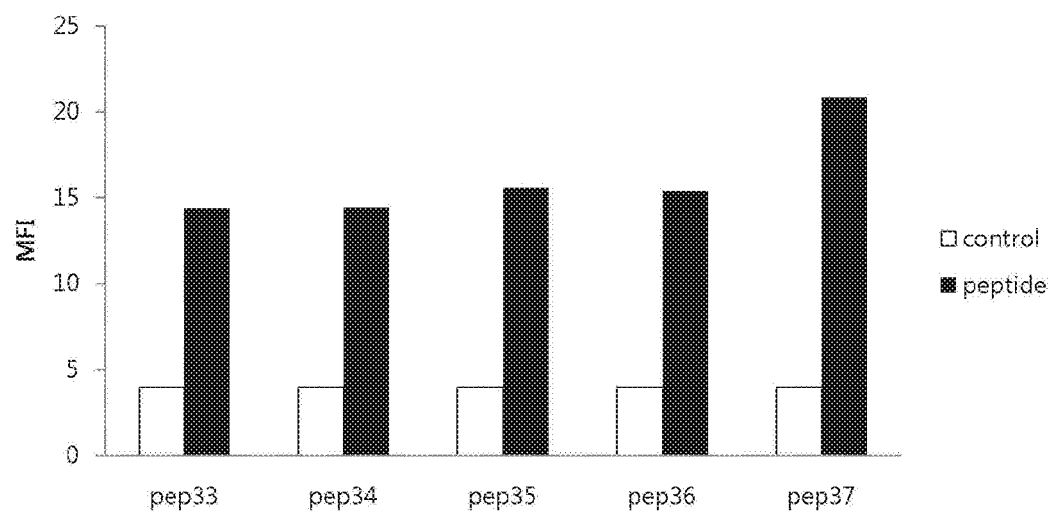
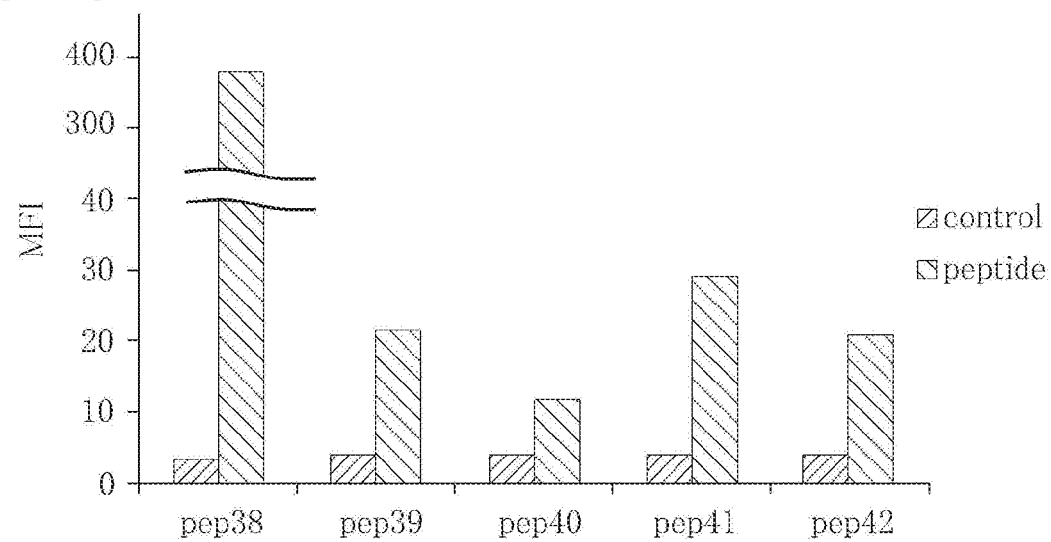

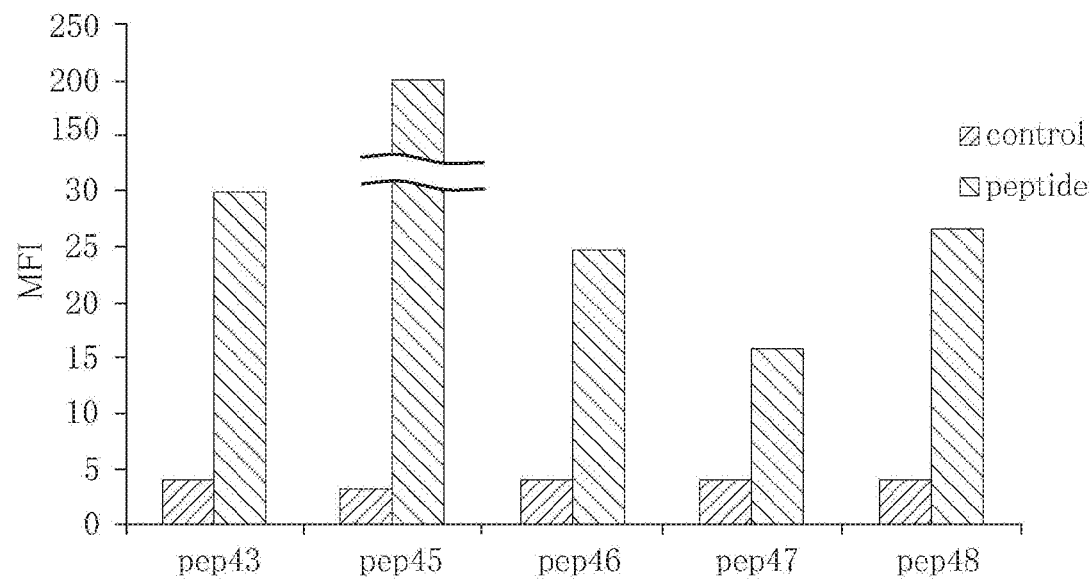
[FIG. 9]
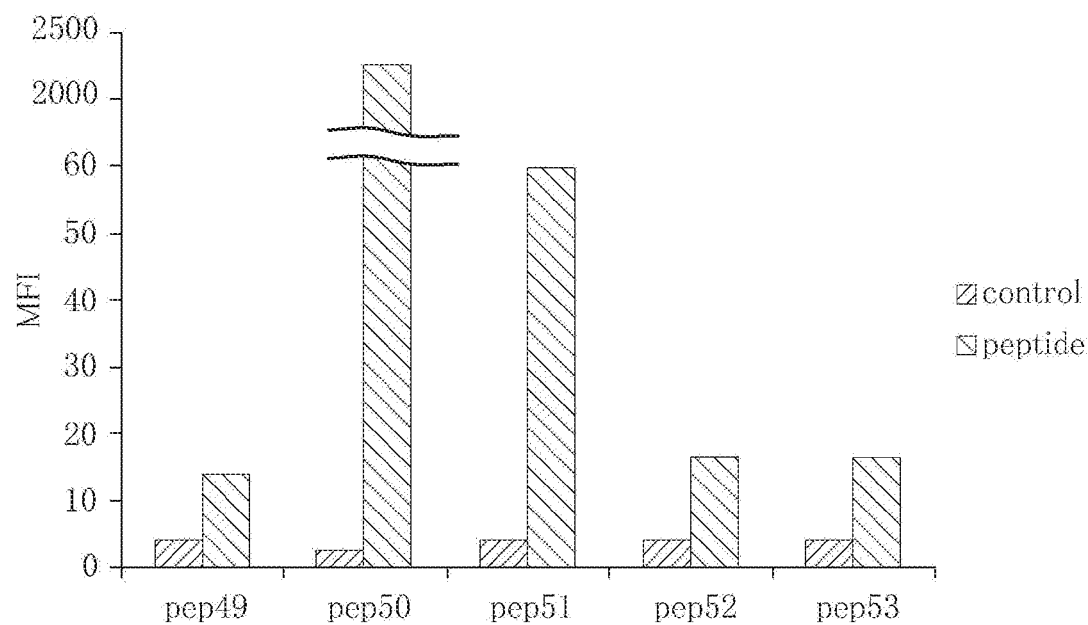
[FIG. 10]

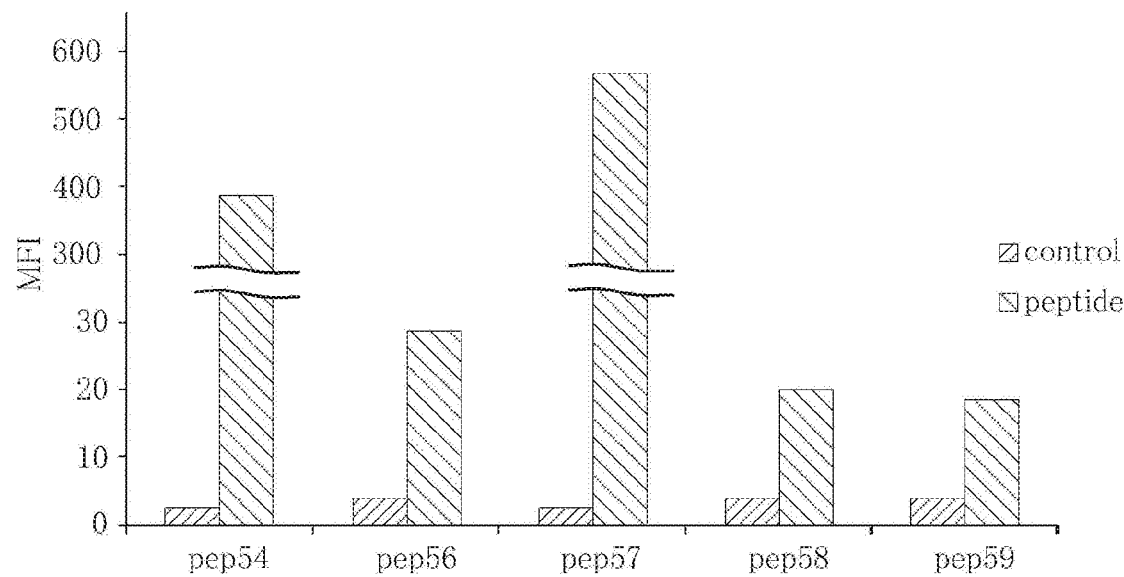
[FIG. 11]
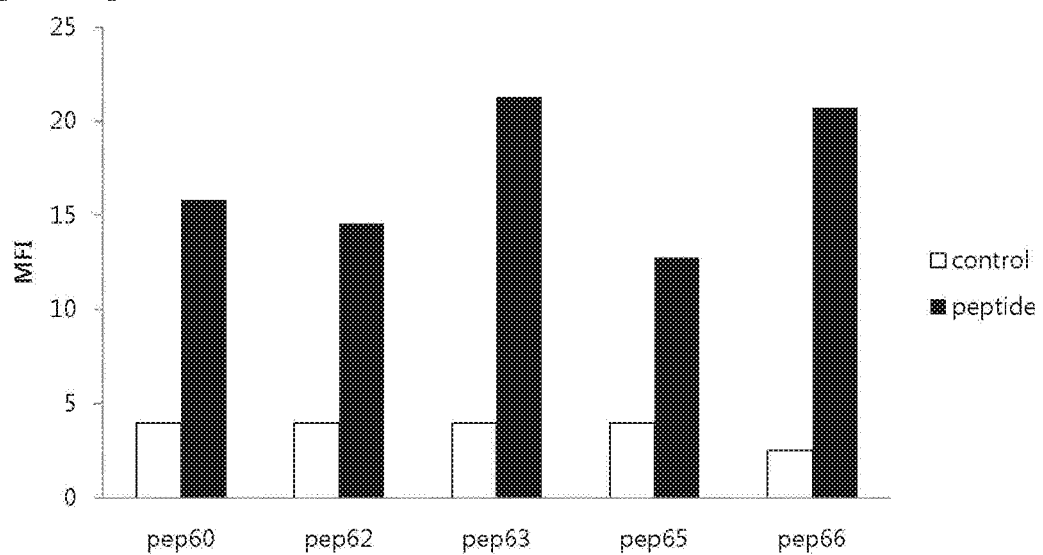
[FIG. 12]

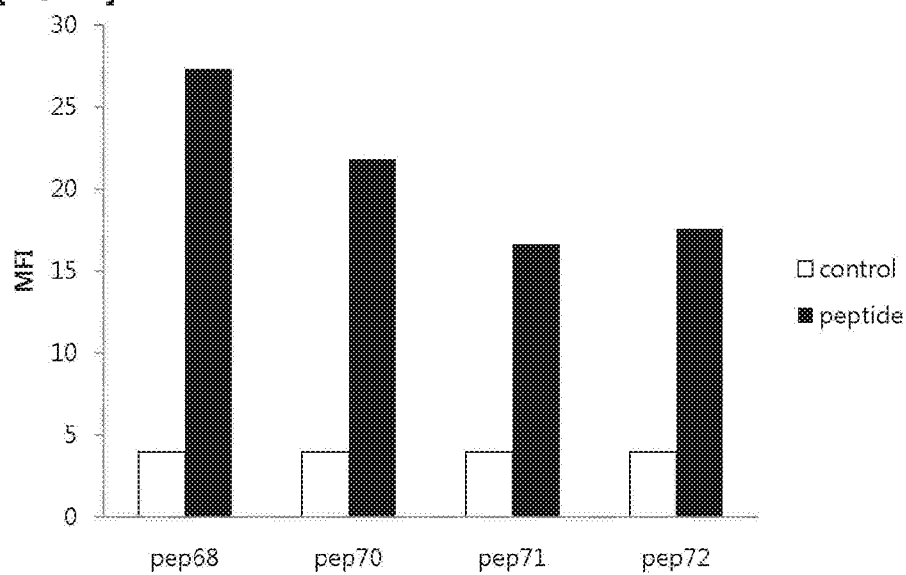
[FIG. 13]
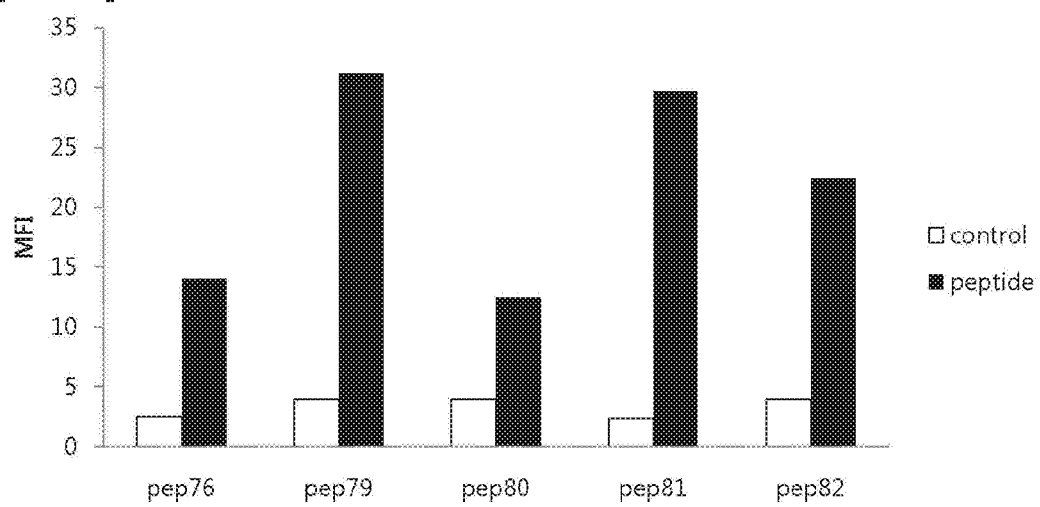
[FIG. 14]

[FIG. 15]
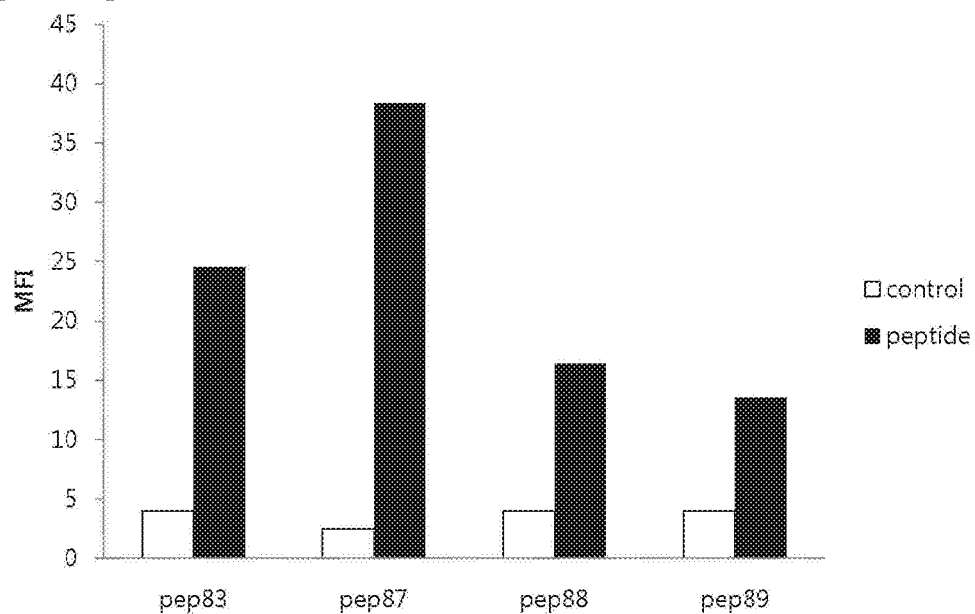
[FIG. 16]
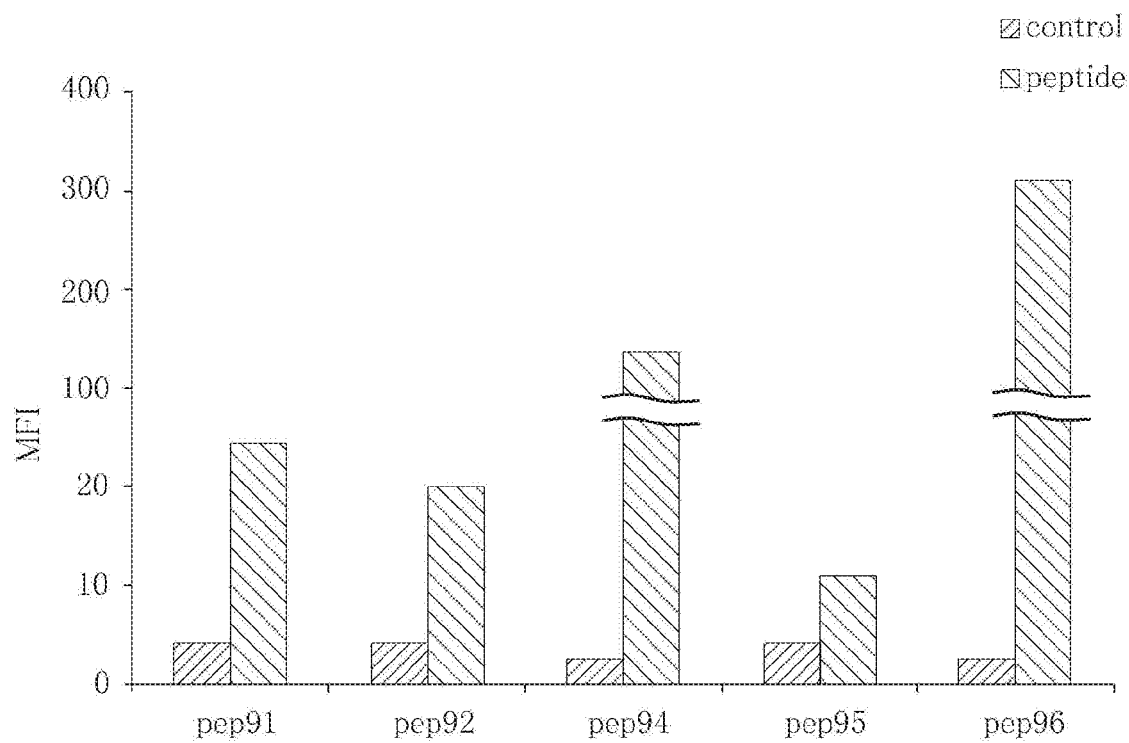

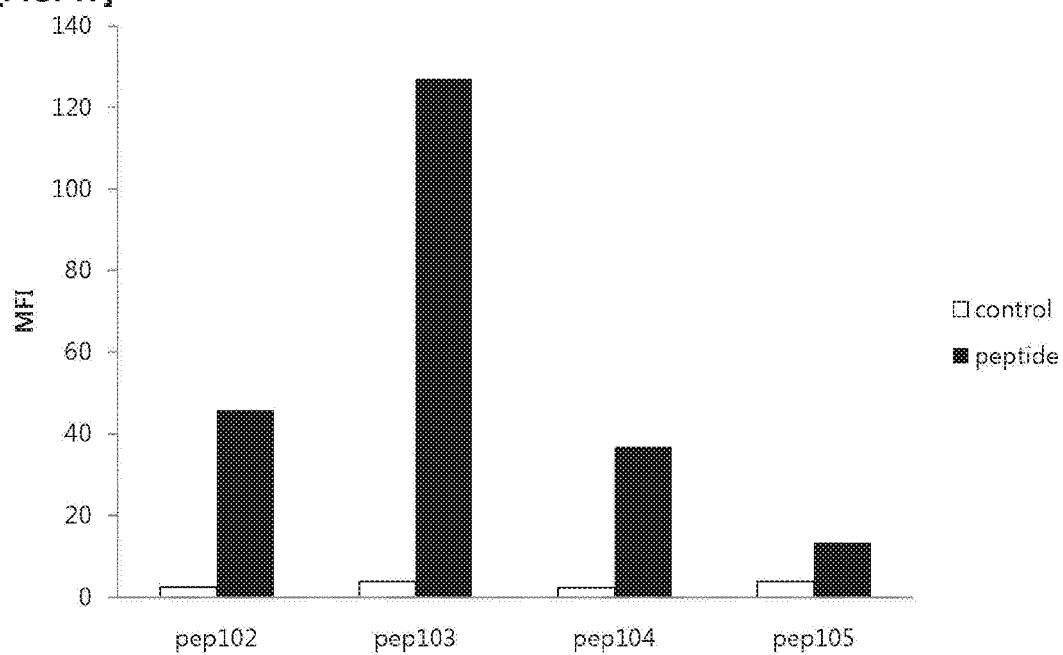
[FIG. 17]
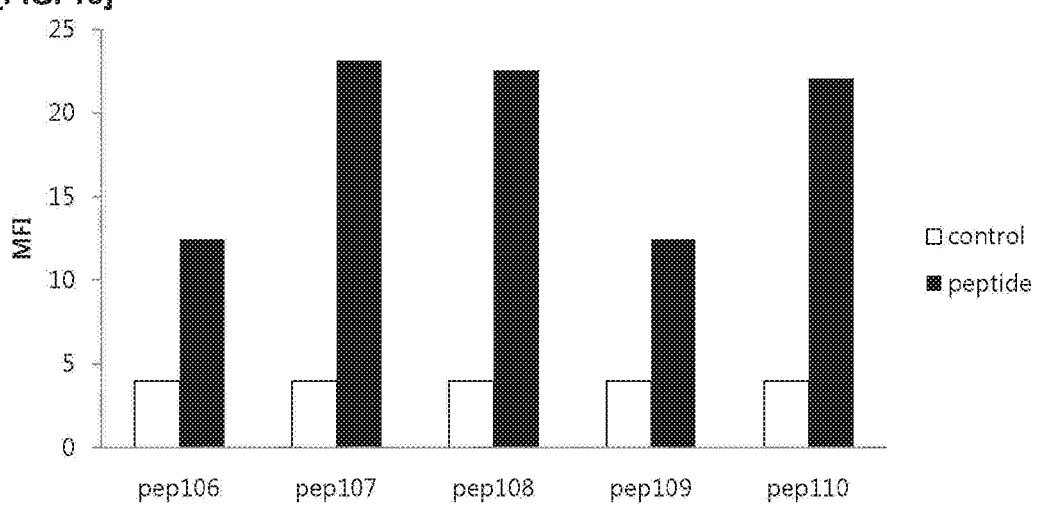
[FIG. 18]

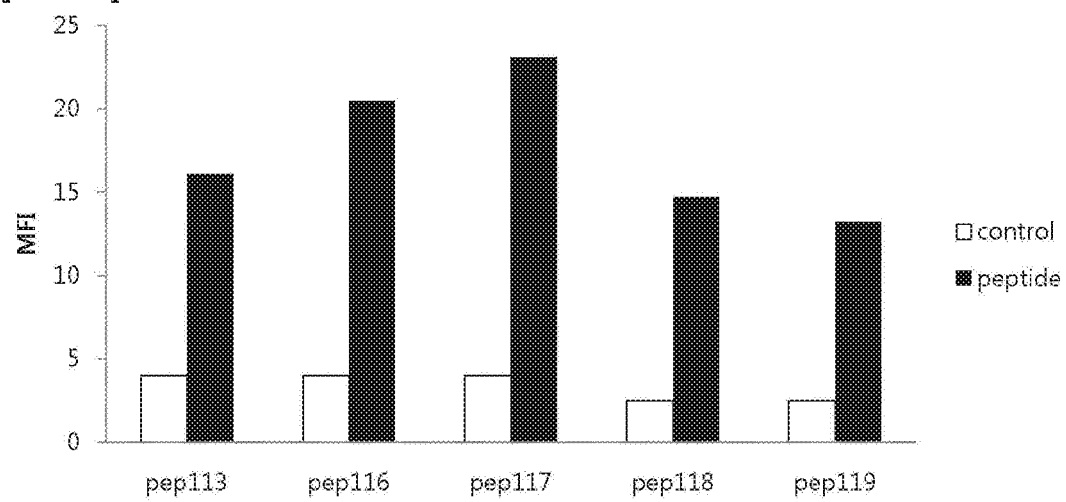
[FIG. 19]
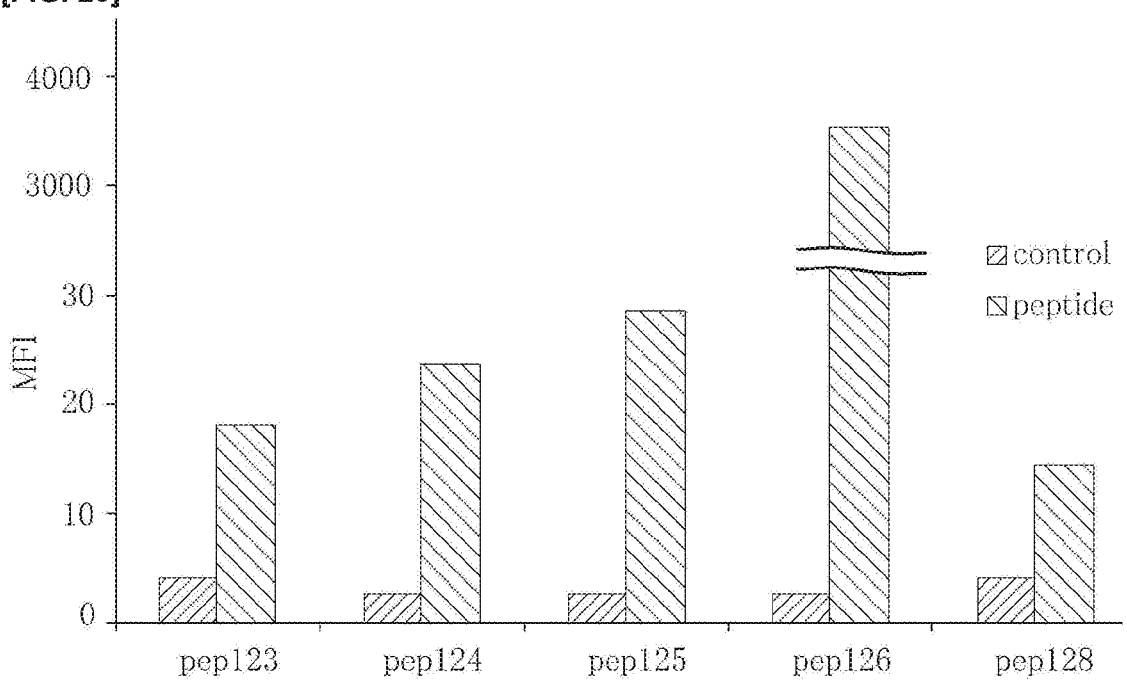
[FIG. 20]

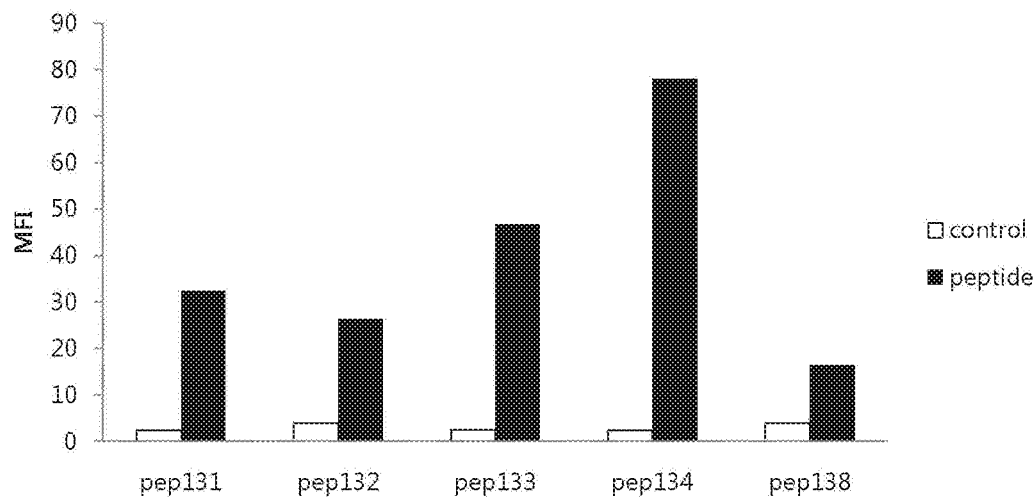
[FIG. 21]
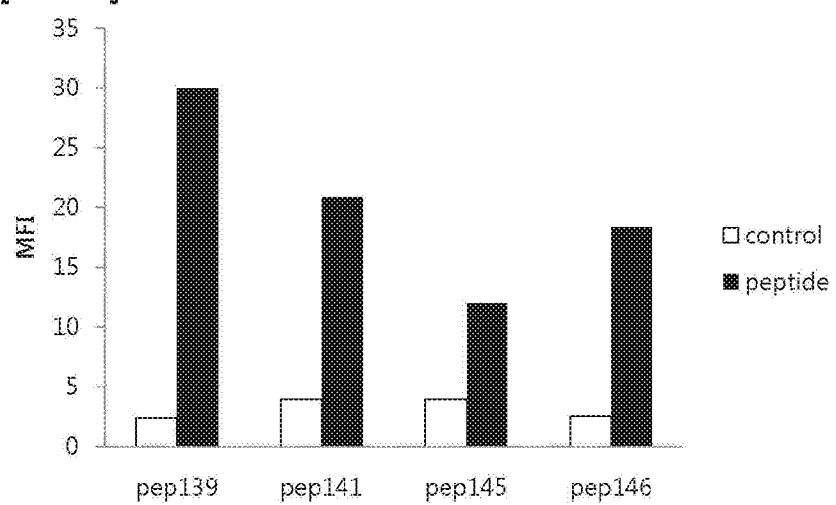
[FIG. 22]

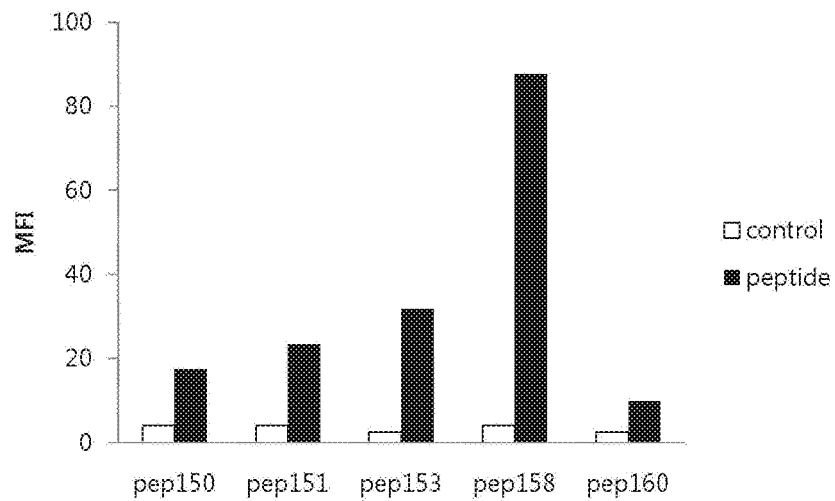
[FIG. 23]
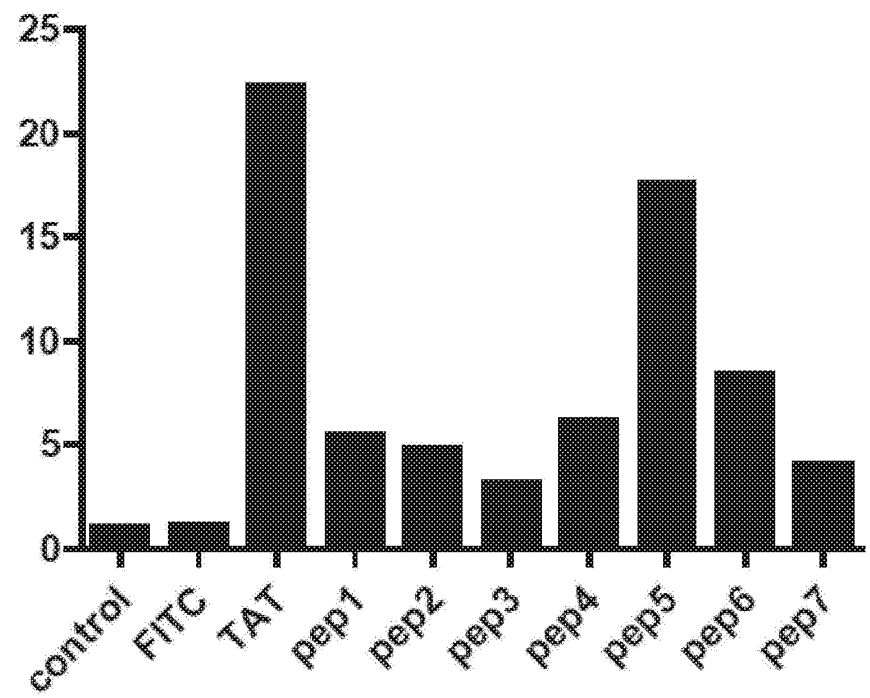
[FIG. 24]

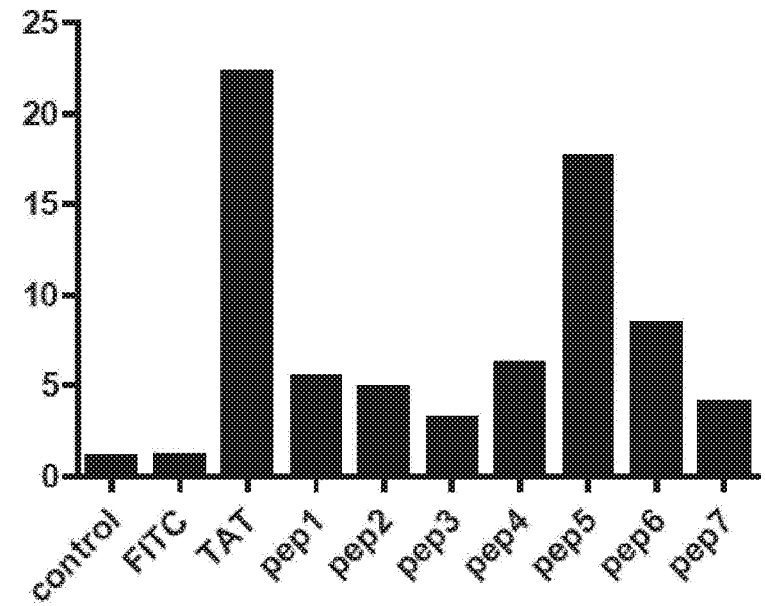
[FIG. 25]
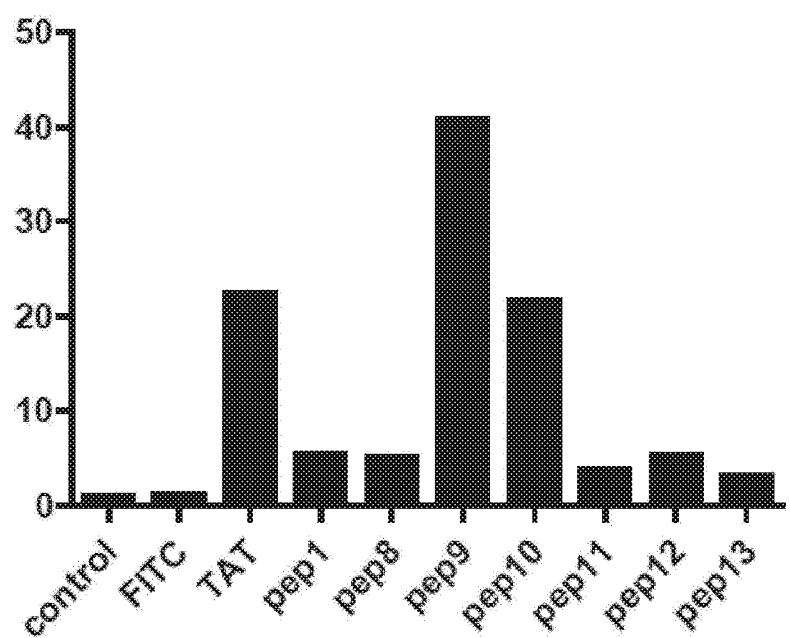
[FIG. 26]

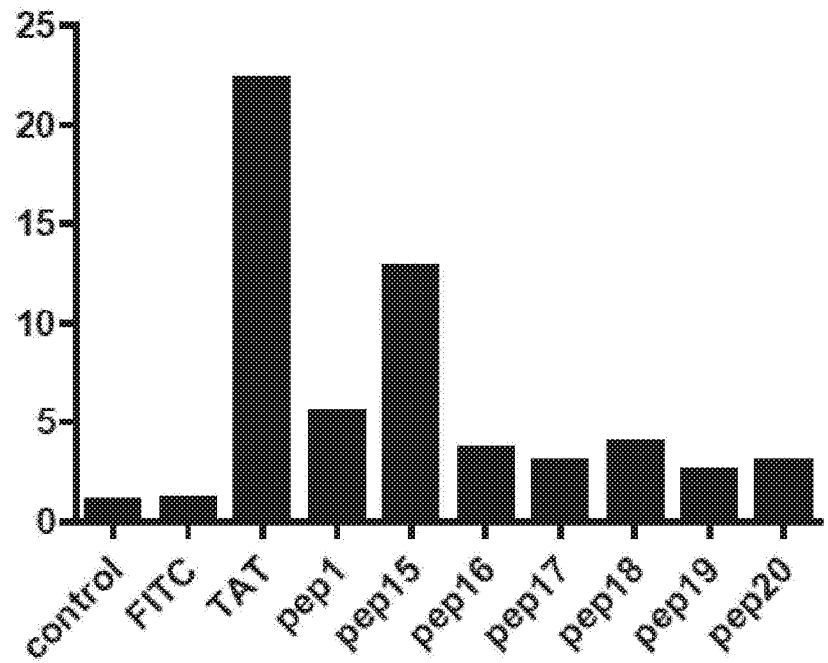
[FIG. 27]
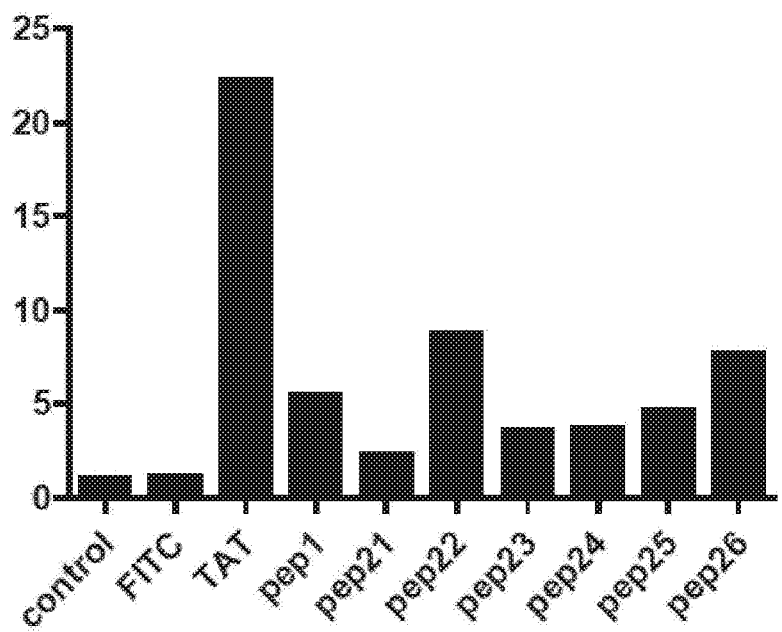
[FIG. 28]

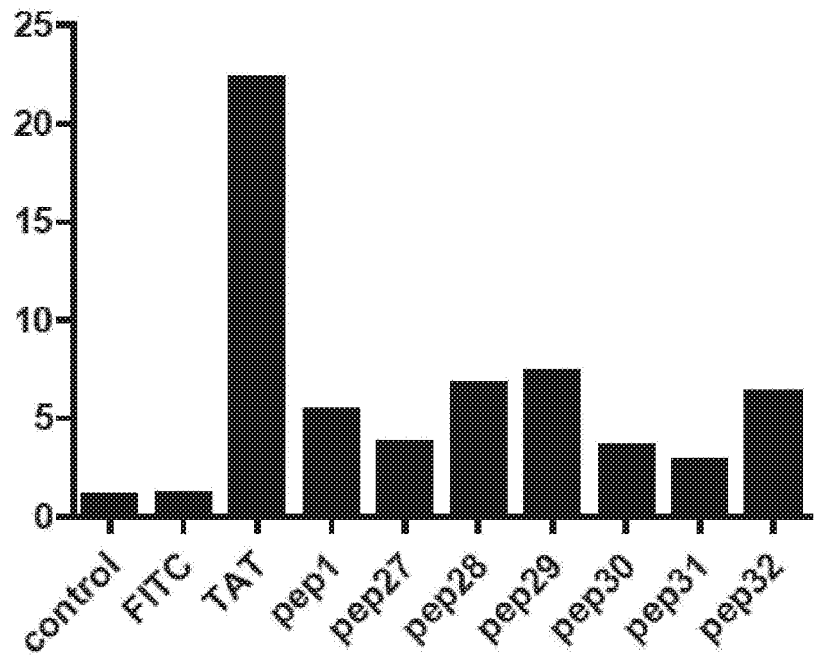
[FIG. 29]
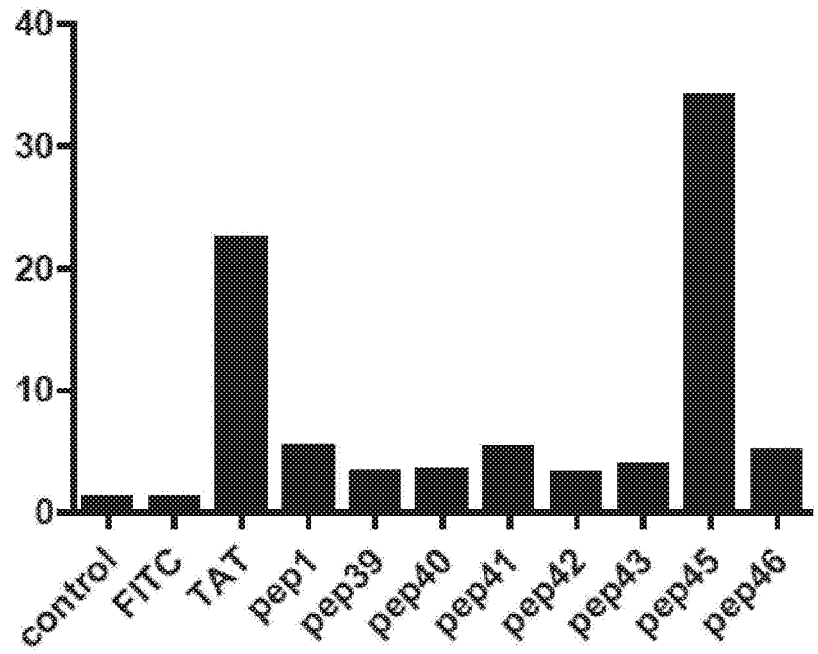
[FIG. 30]

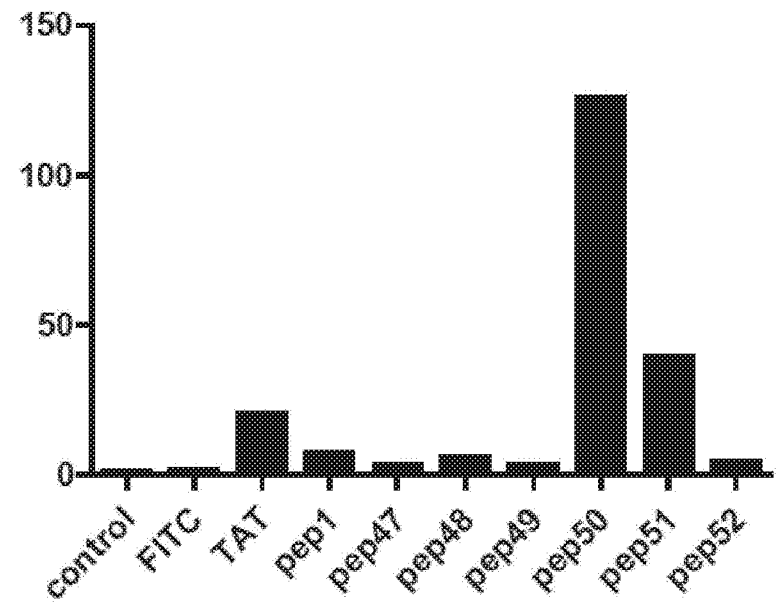
[FIG. 31]
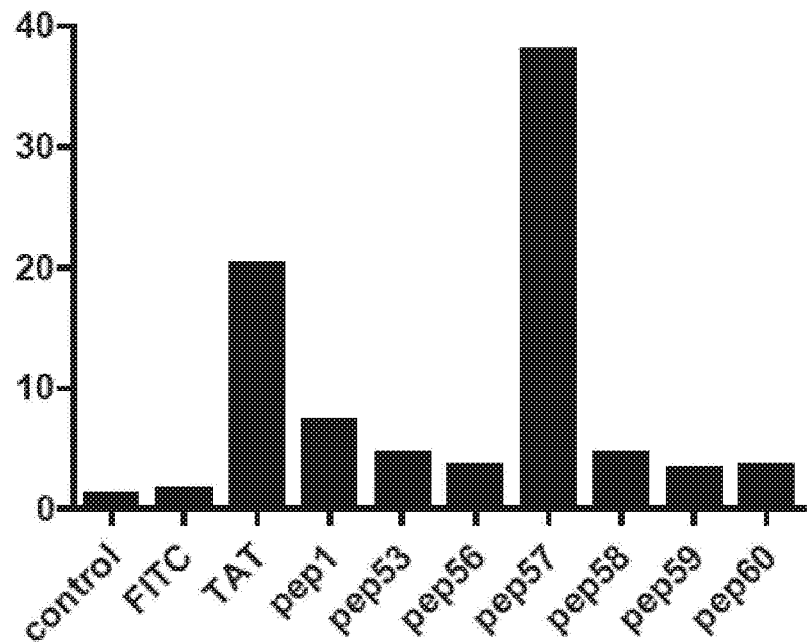
[FIG. 32]

[FIG. 33]
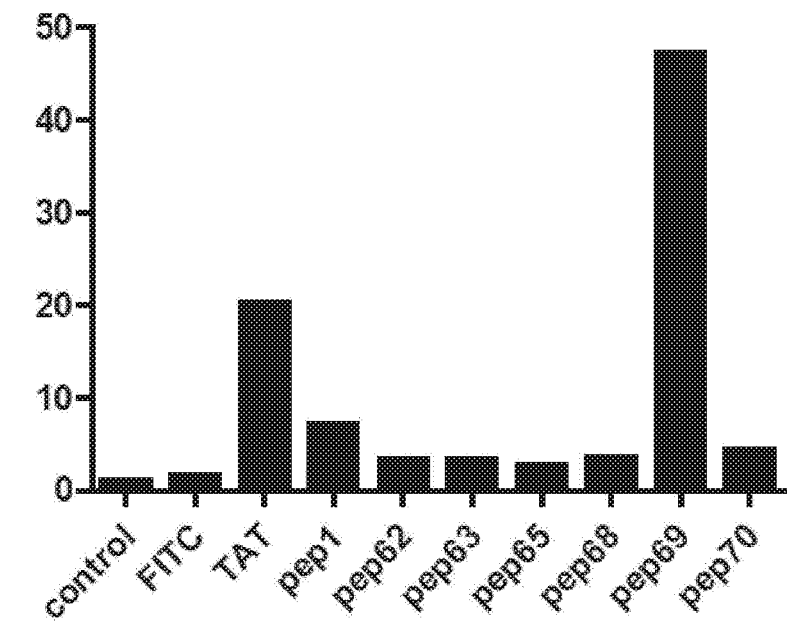
[FIG. 34]
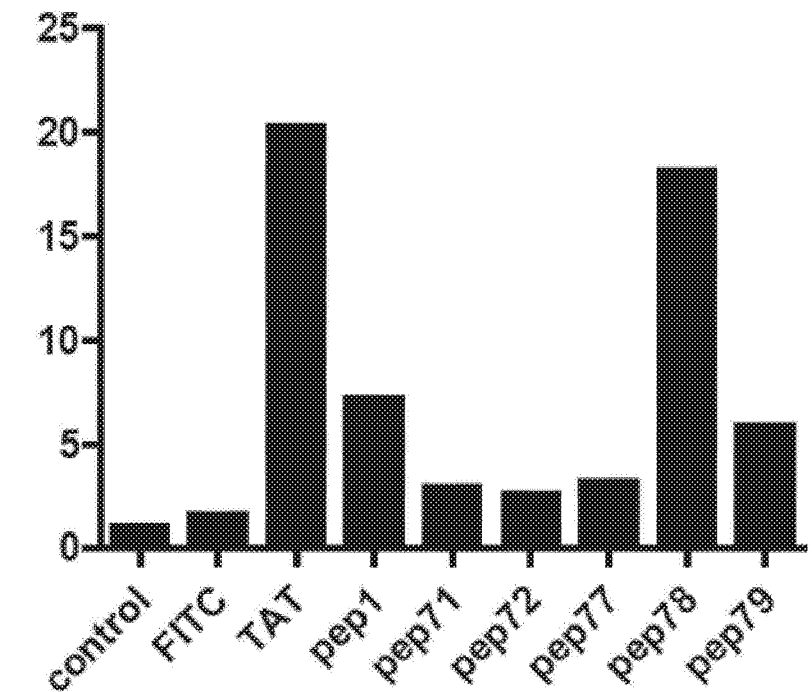

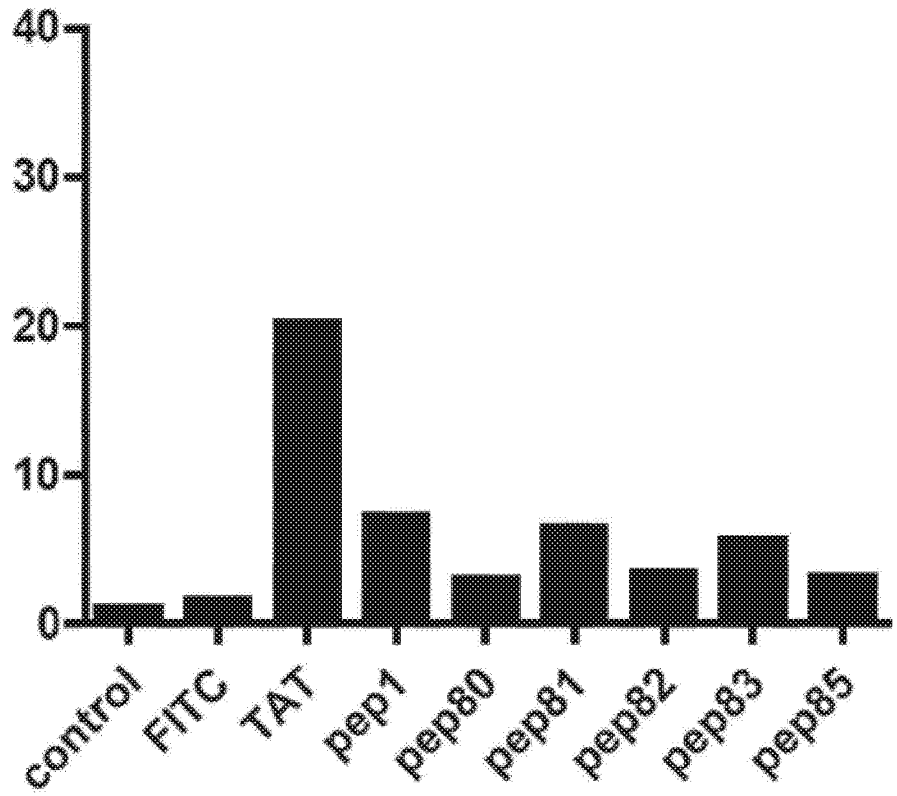
[FIG. 35]
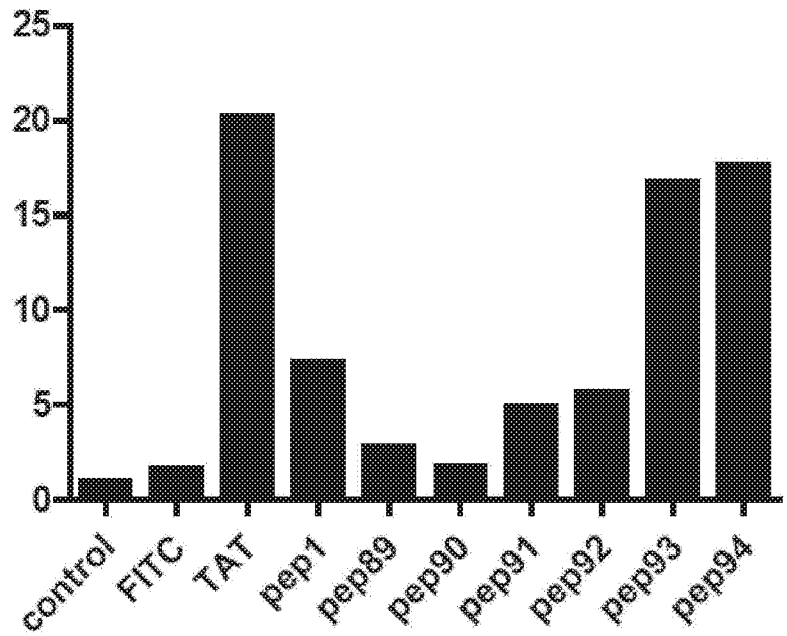
[FIG. 36]

[FIG. 37]
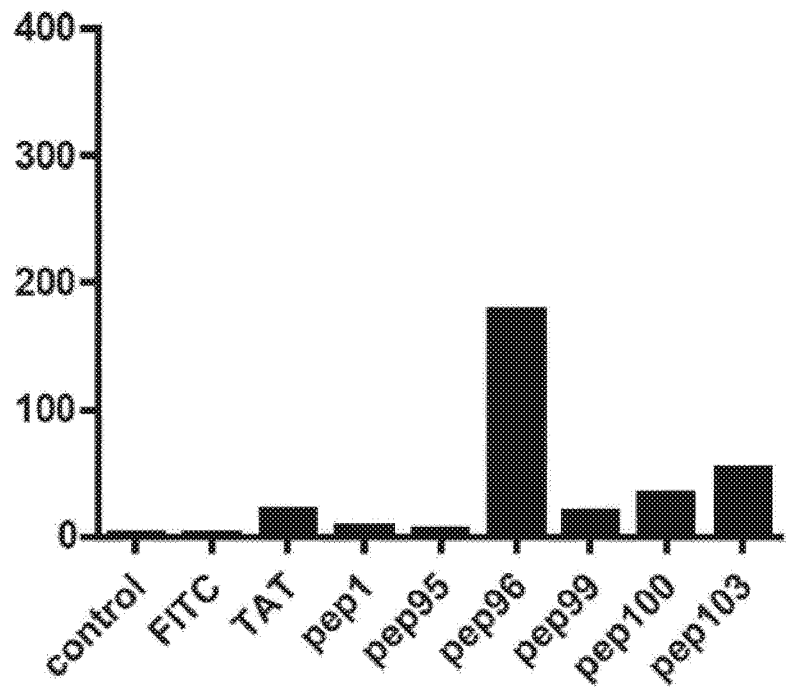
[FIG. 38]
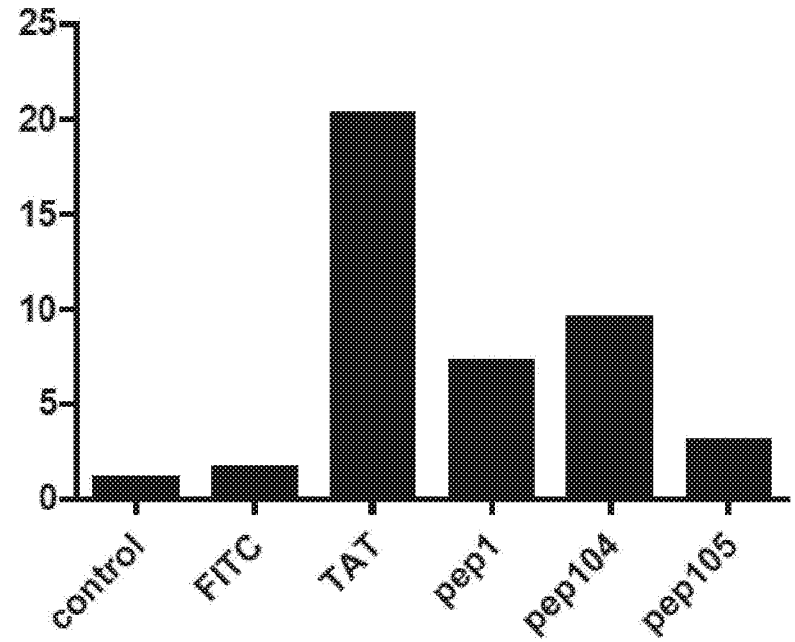

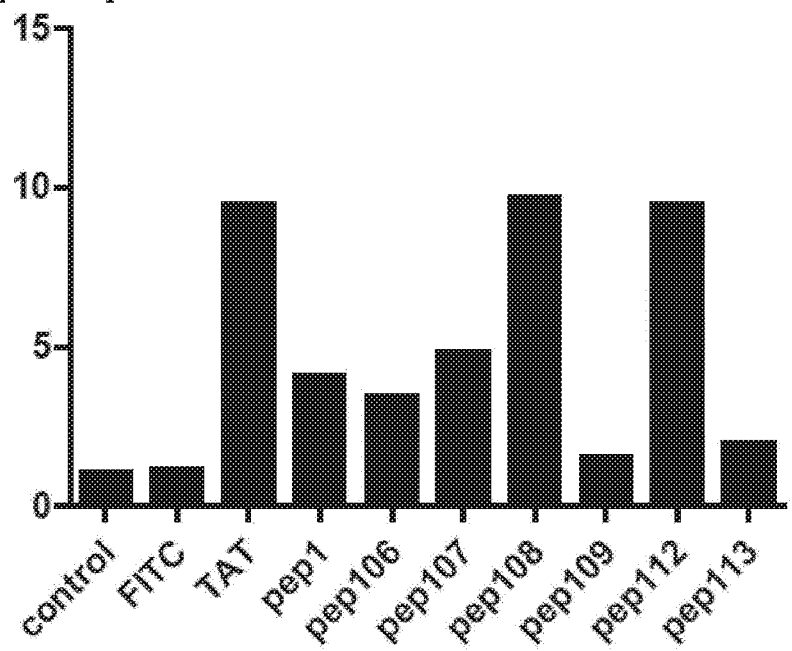
[FIG. 39]
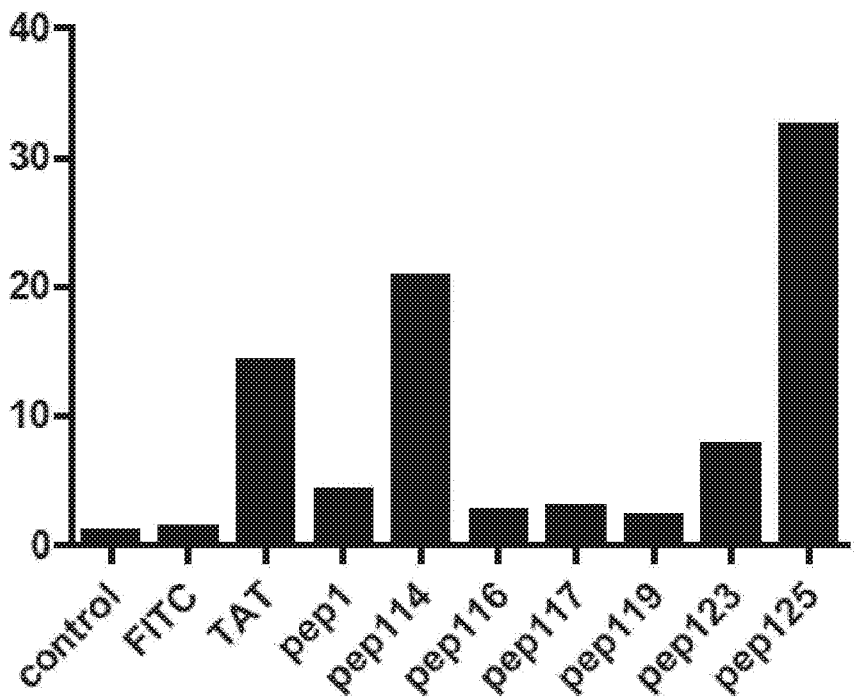
[FIG. 40]

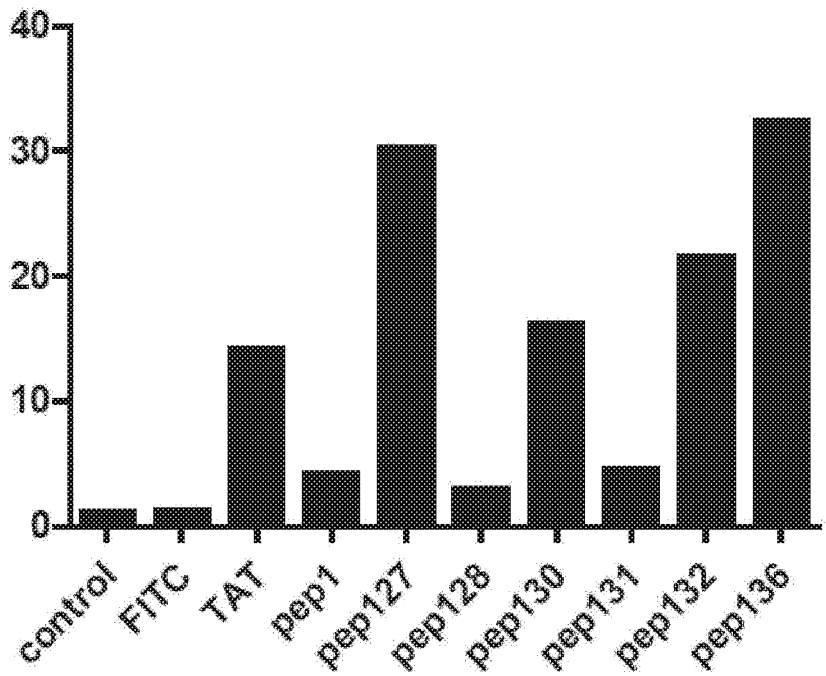
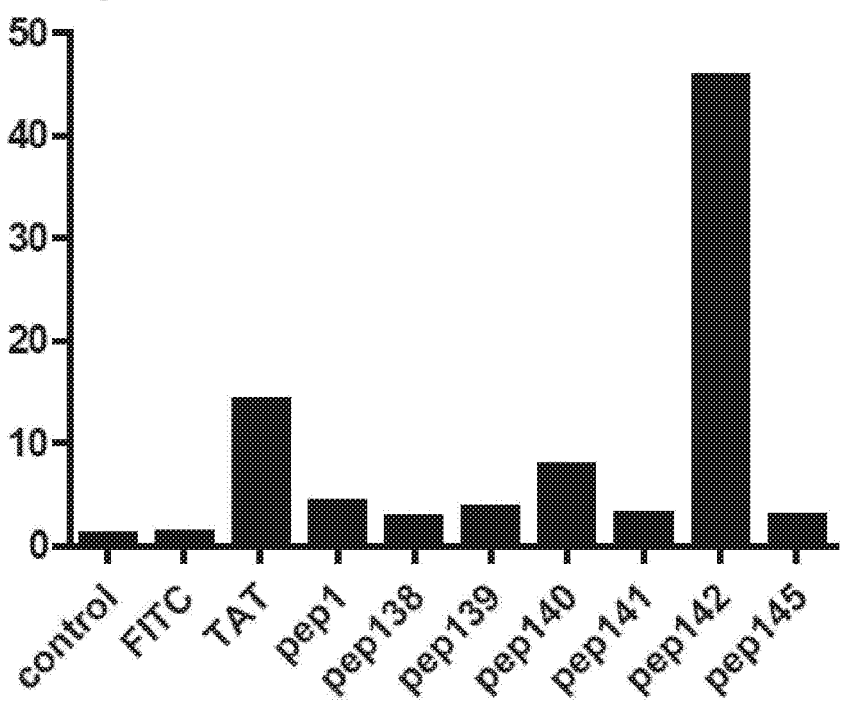

[FIG. 43]
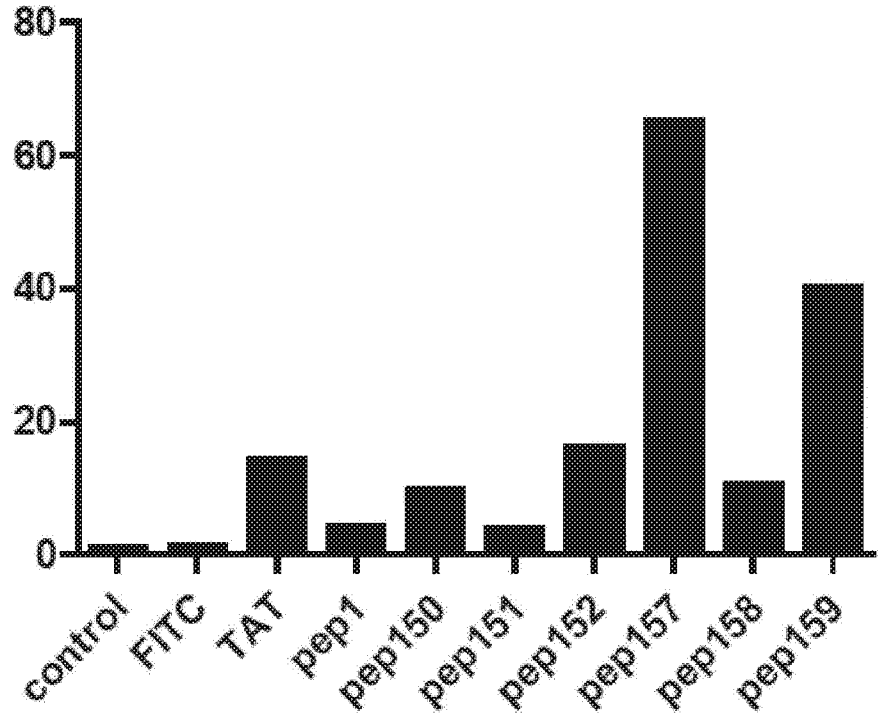
[FIG. 44]
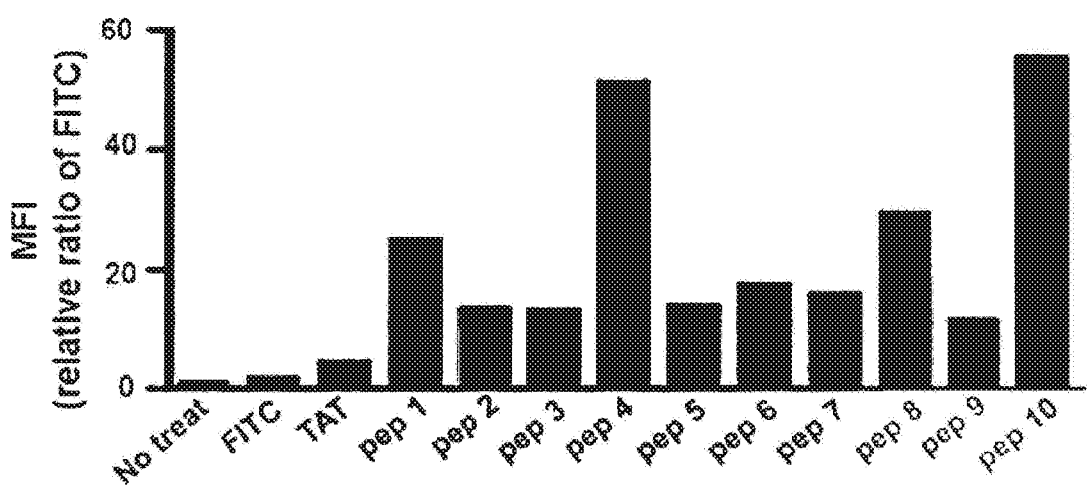

[FIG. 45]
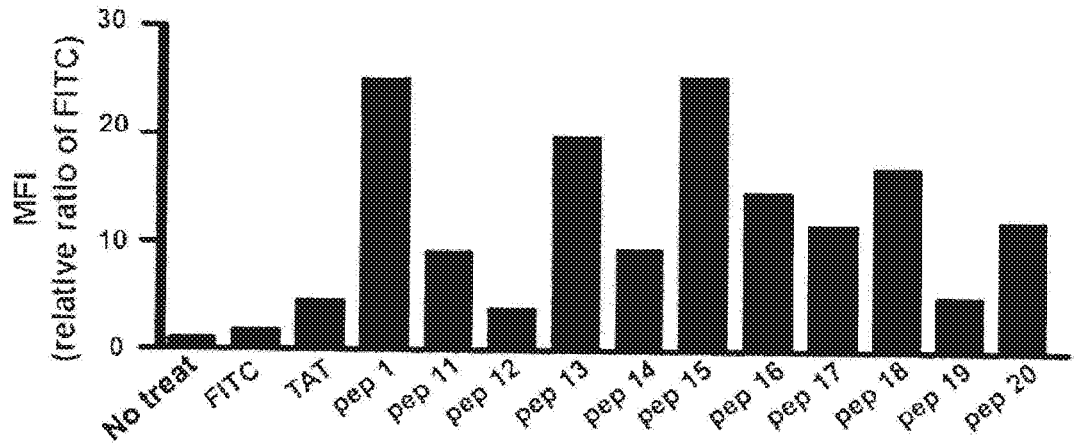
[FIG. 46]
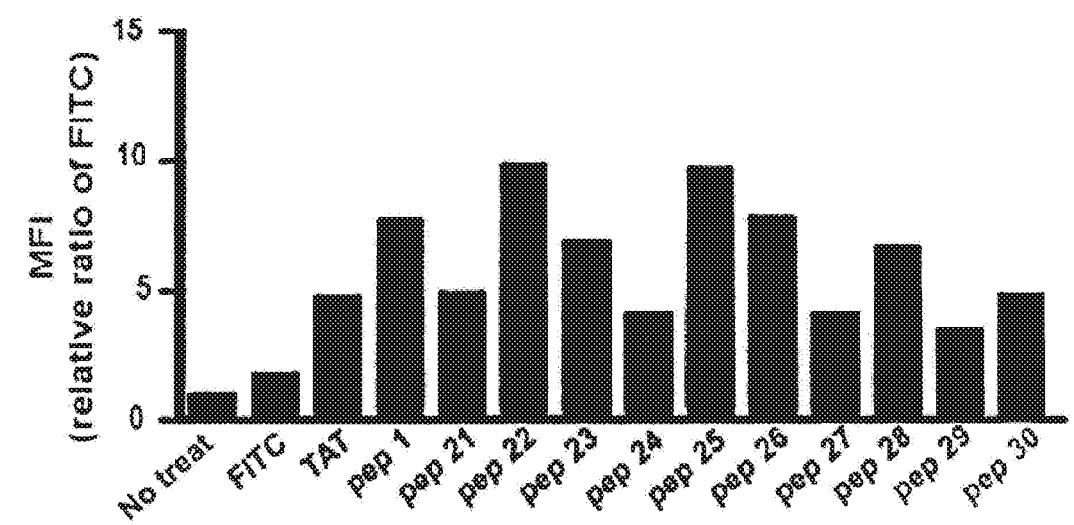
[FIG. 47]
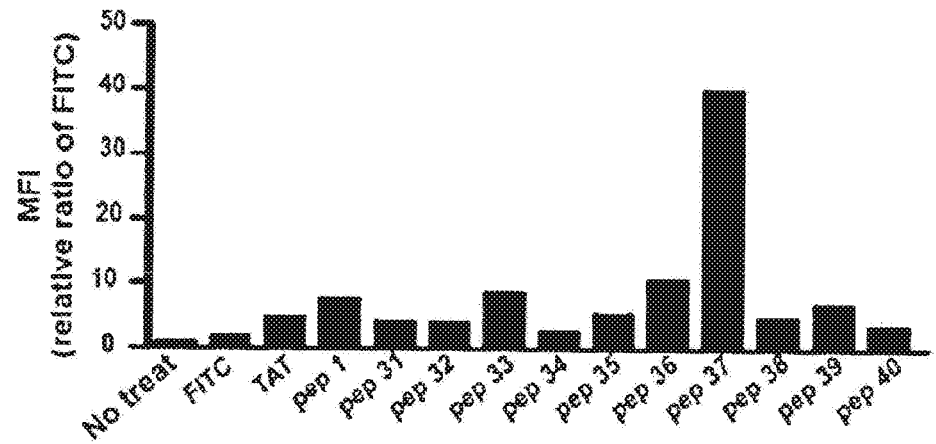

[FIG. 48]
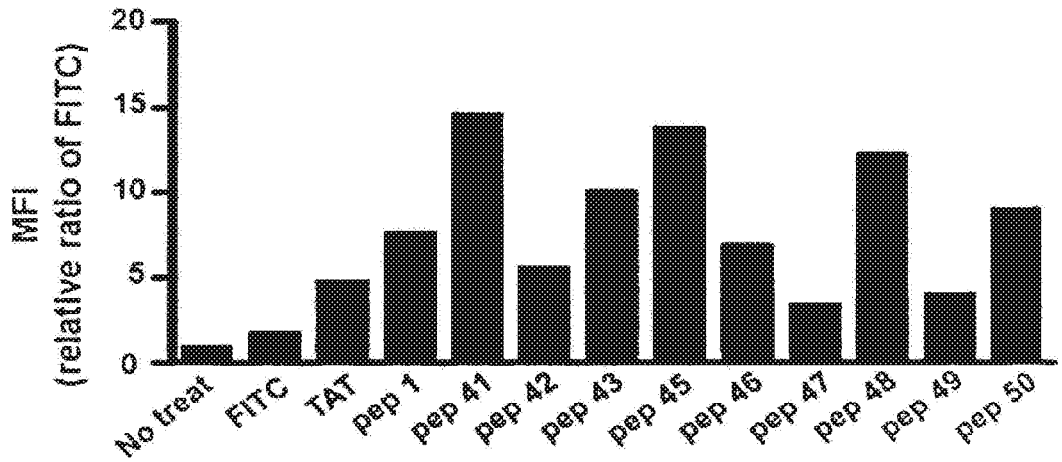
[FIG. 49]
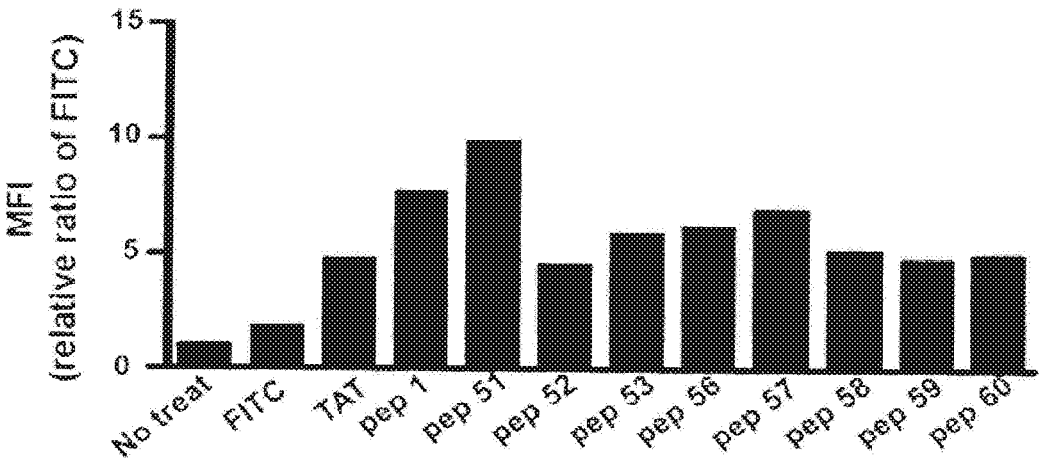
[FIG. 50]
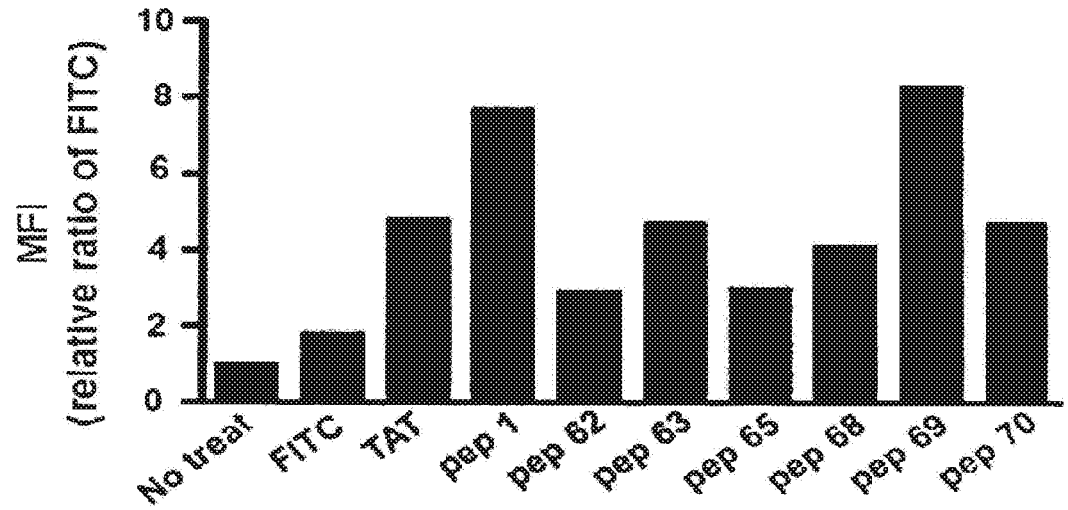

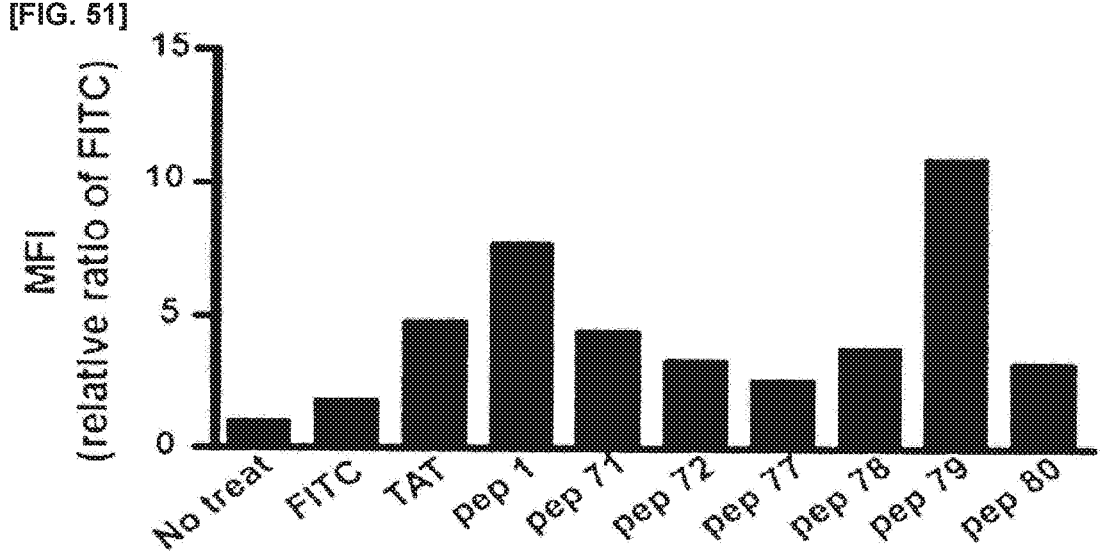
[FIG. 51]
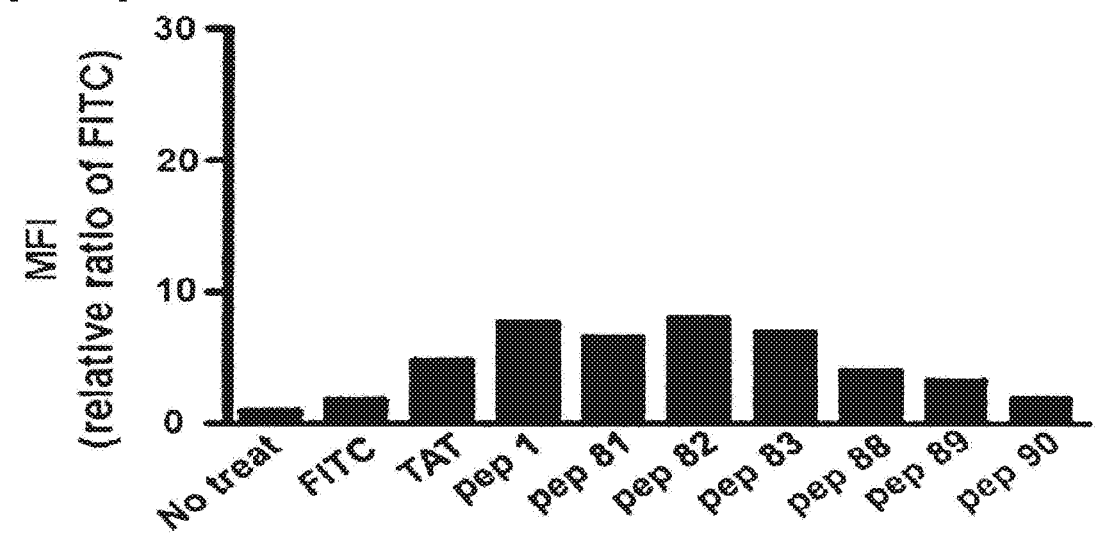
[FIG. 52]
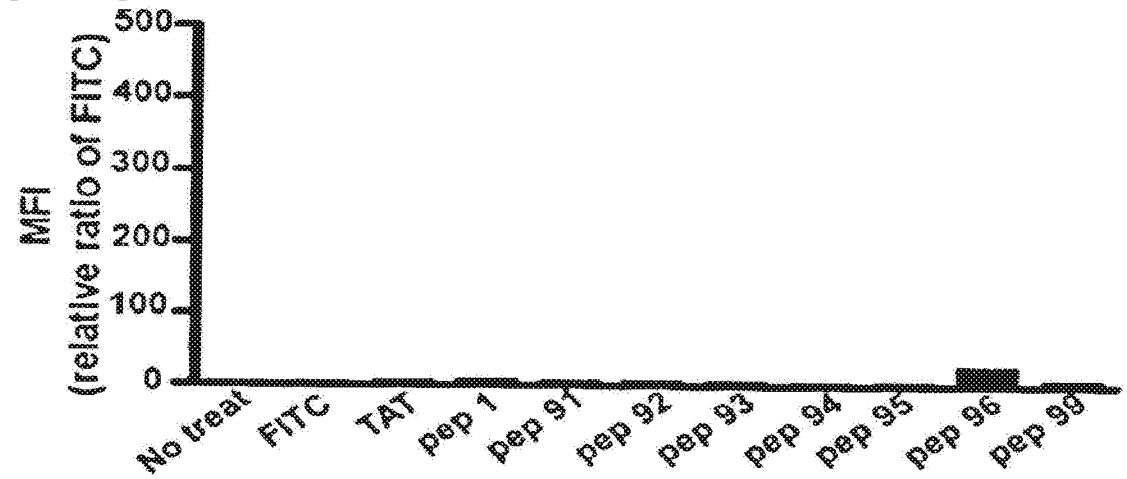
[FIG. 53]

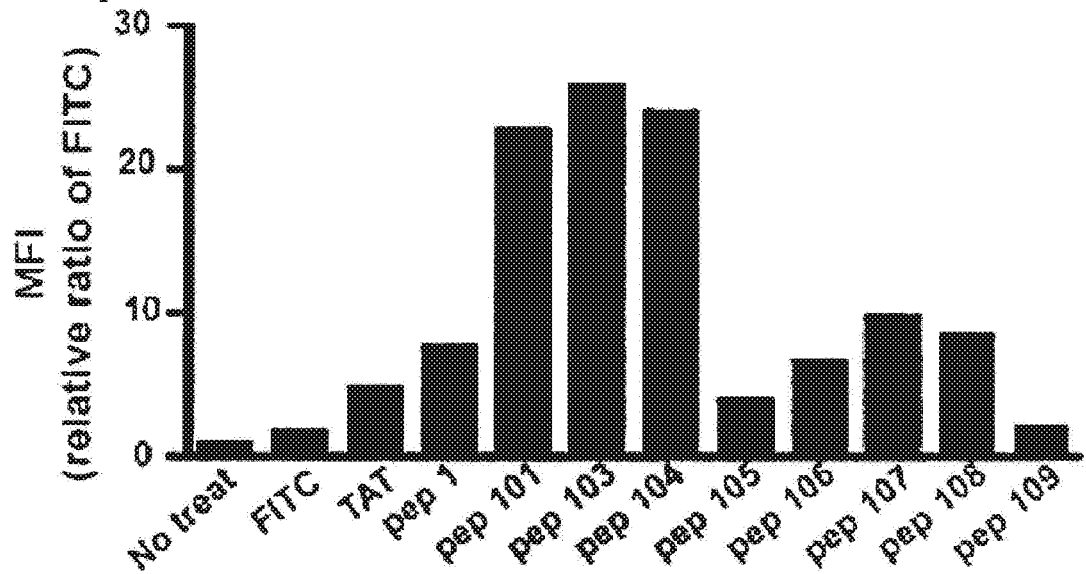
[FIG. 54]
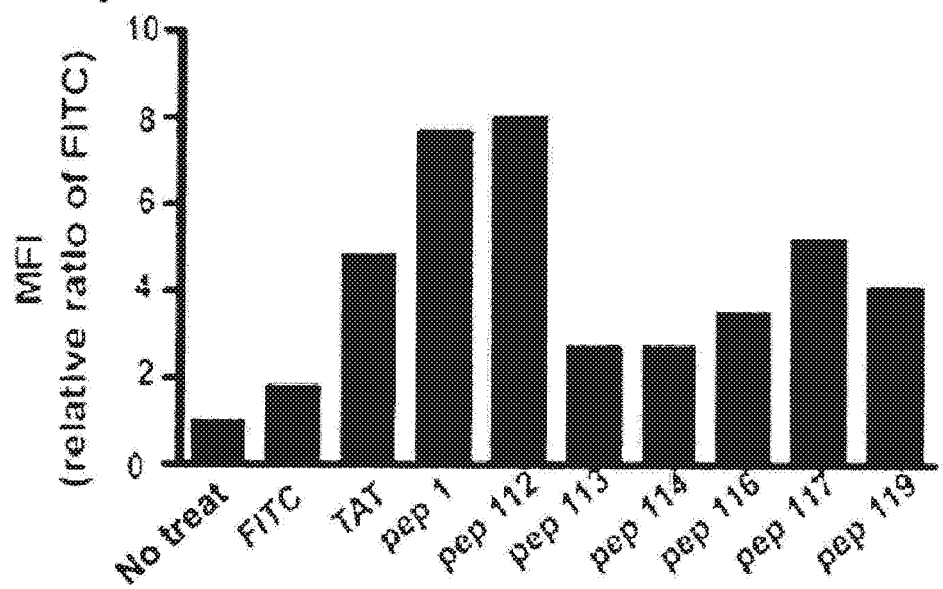
[FIG. 55]

[FIG. 56]
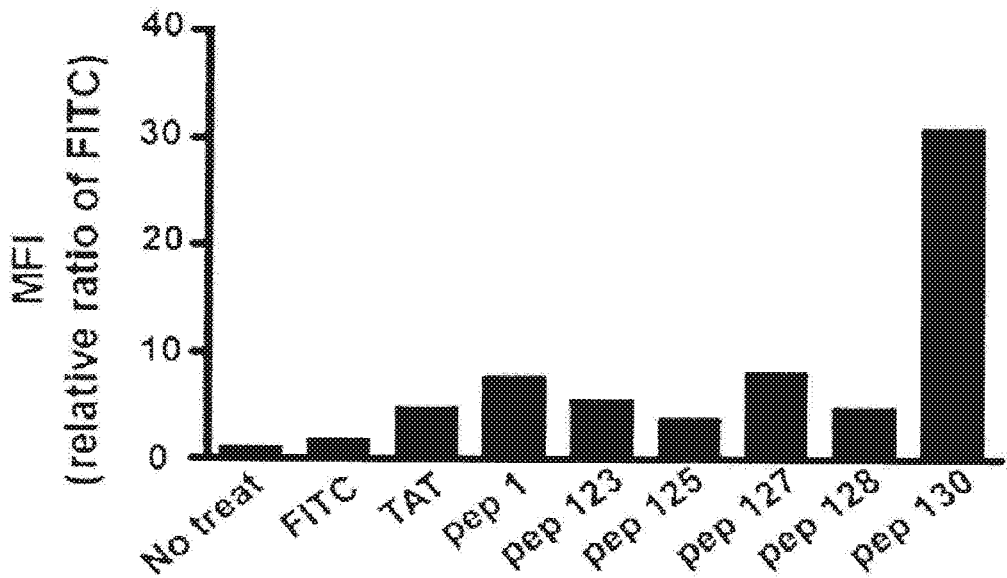
[FIG. 57]
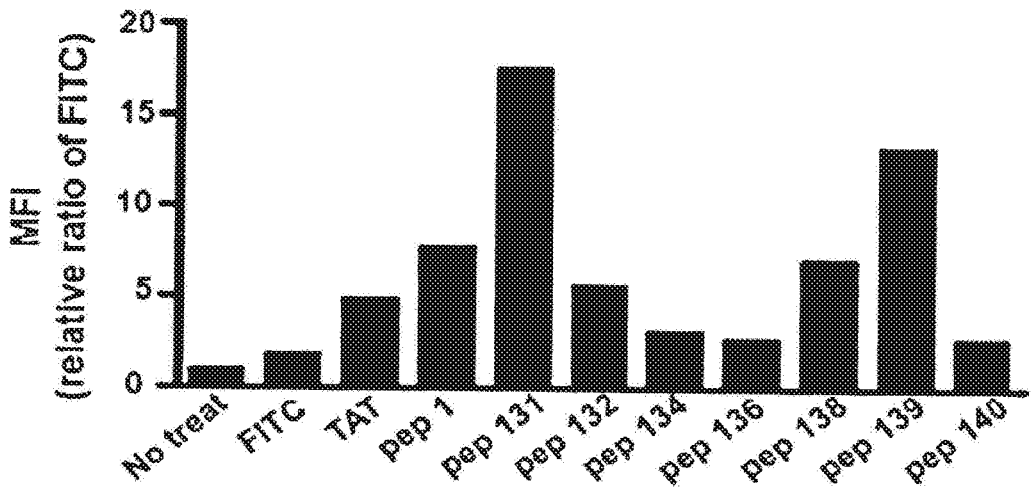

[FIG. 58]
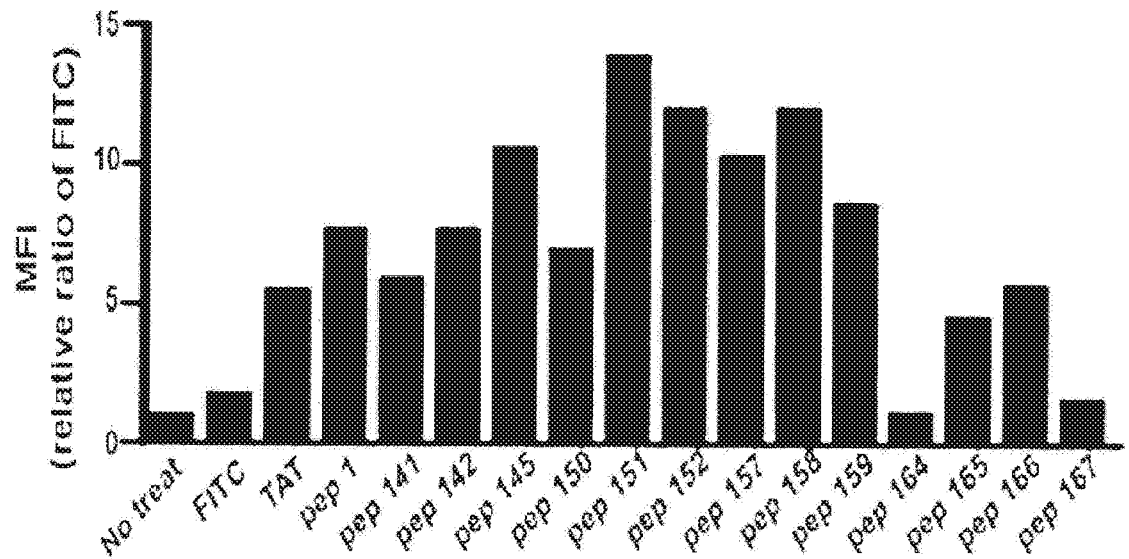
[FIG. 59]
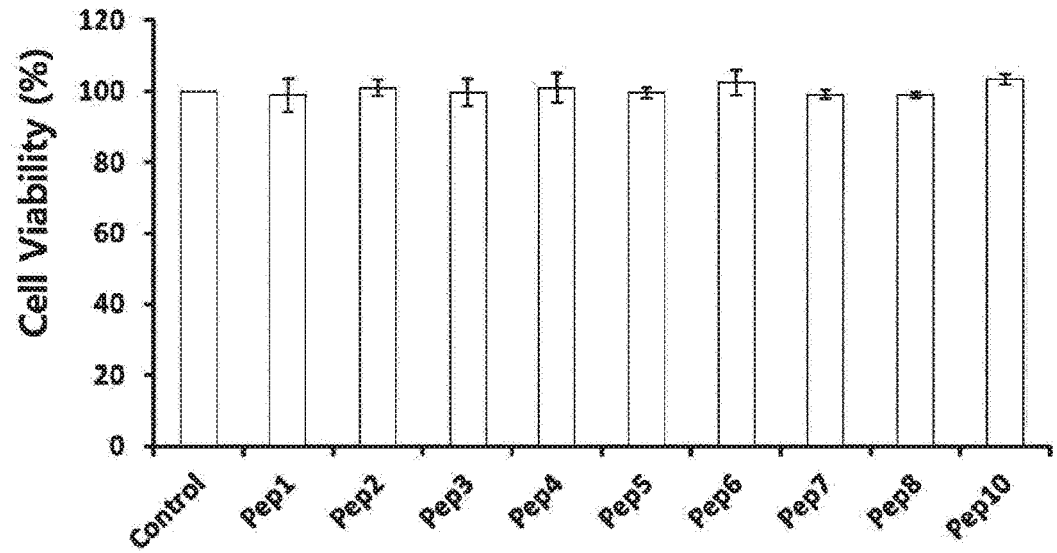

[FIG. 60]
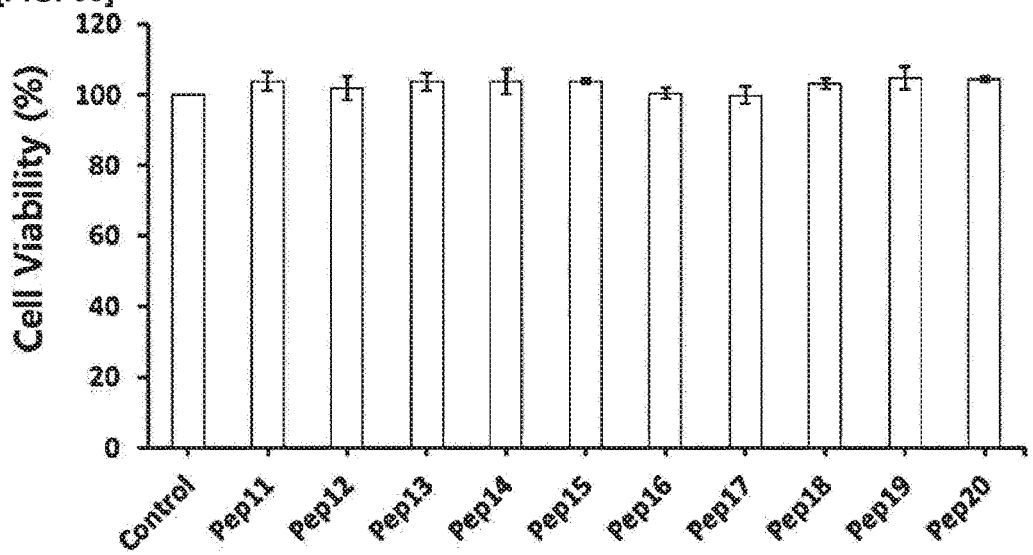
[FIG. 61]
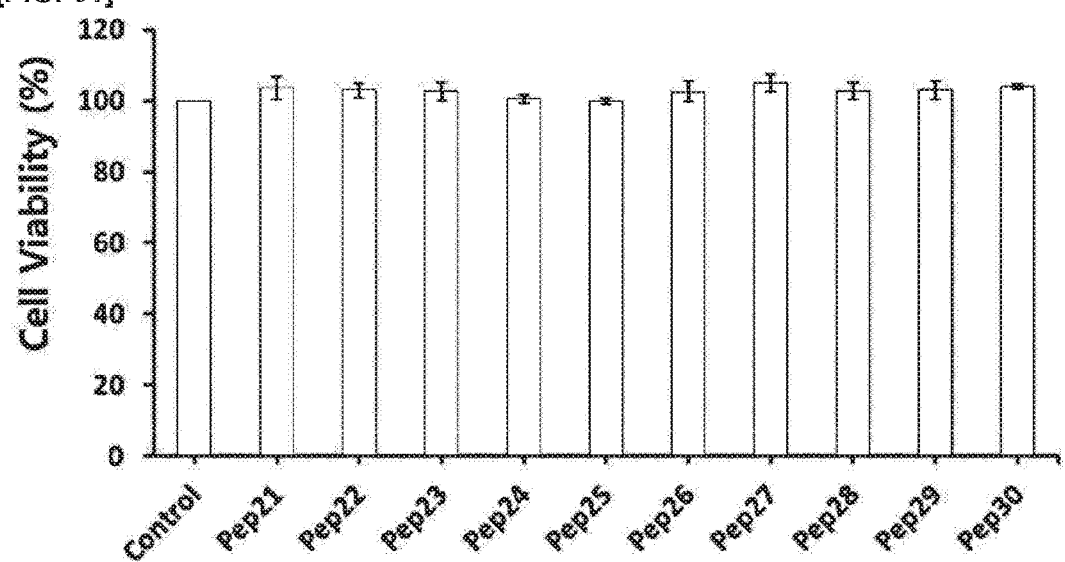

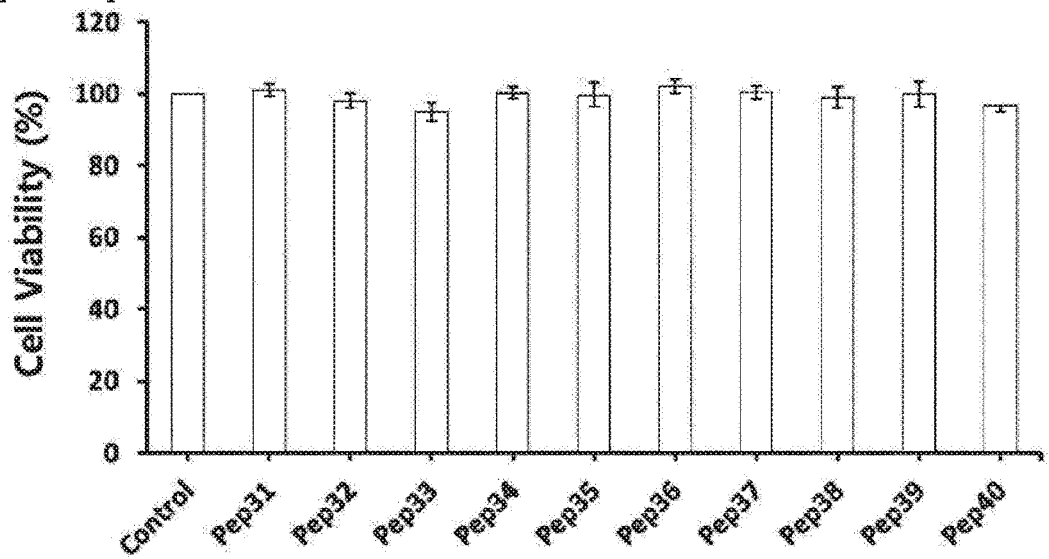
[FIG. 62]
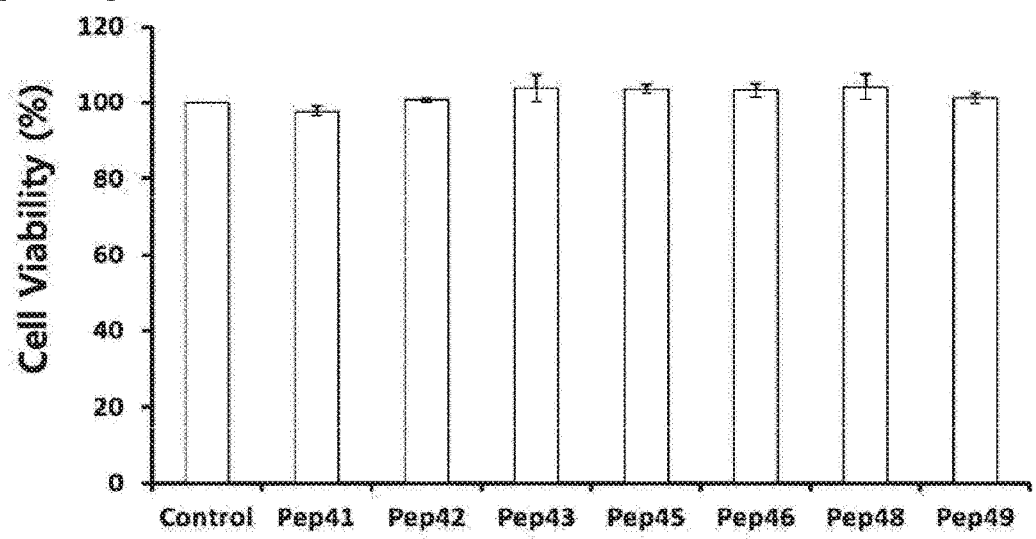
[FIG. 63]

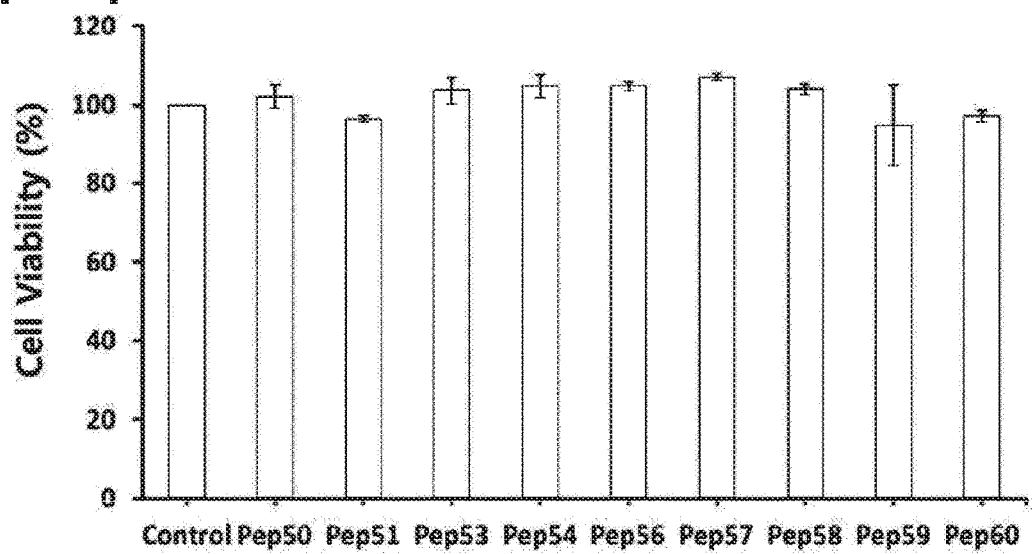
[FIG. 64]
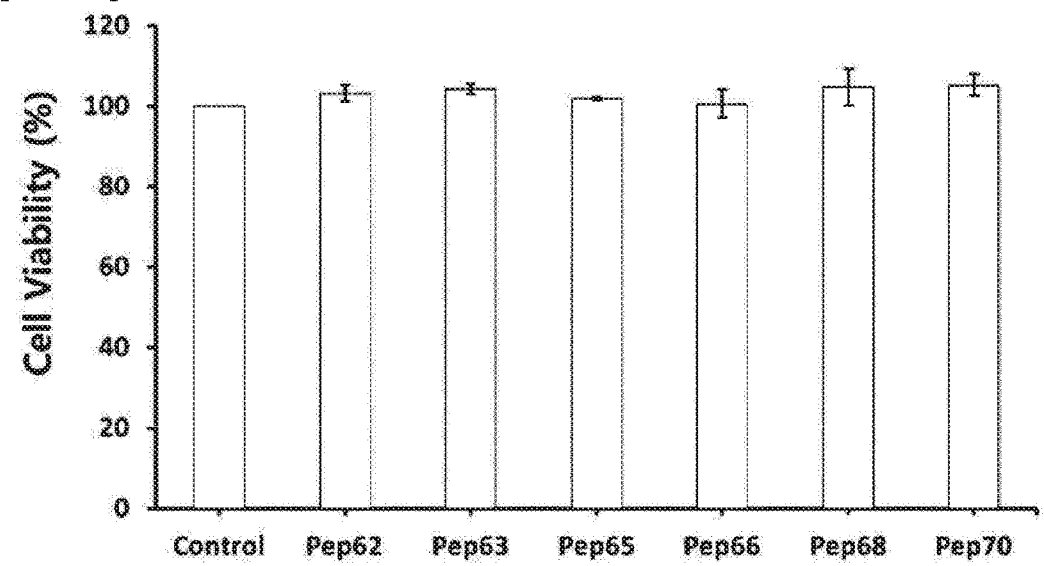
[FIG. 65]

[FIG. 66]
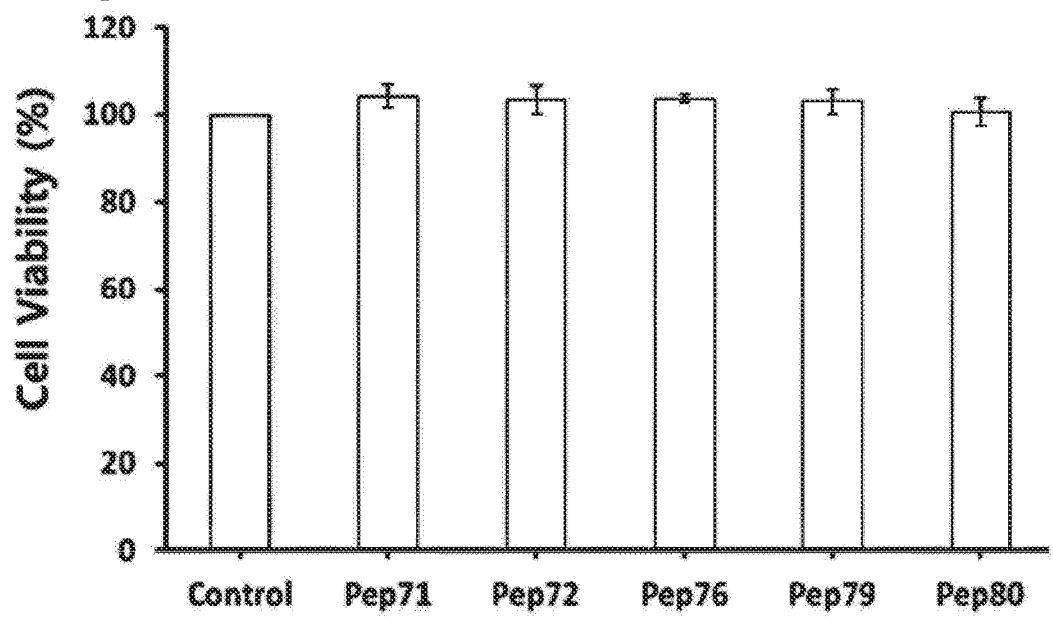
[FIG. 67]
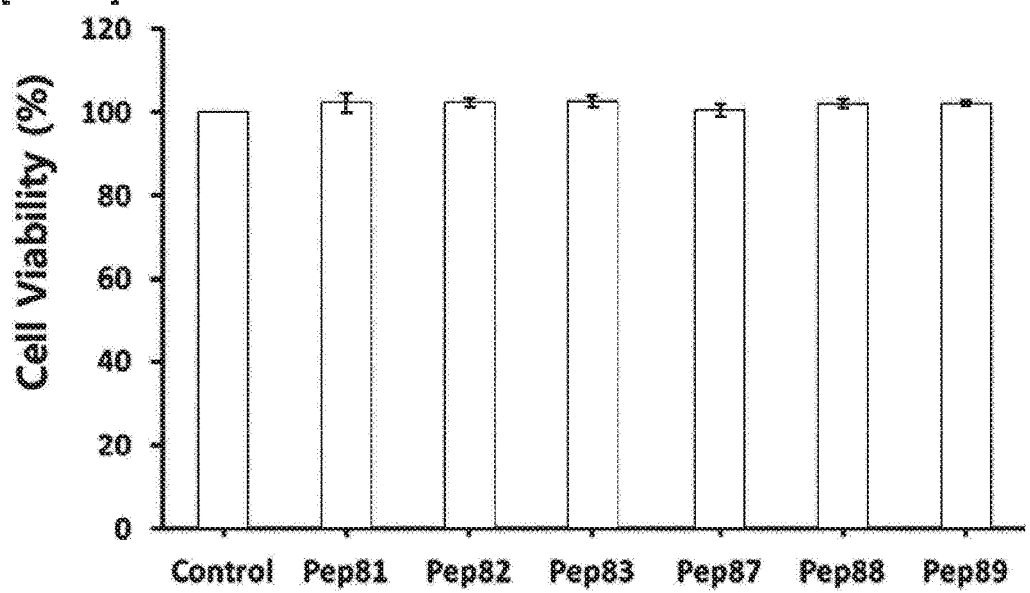

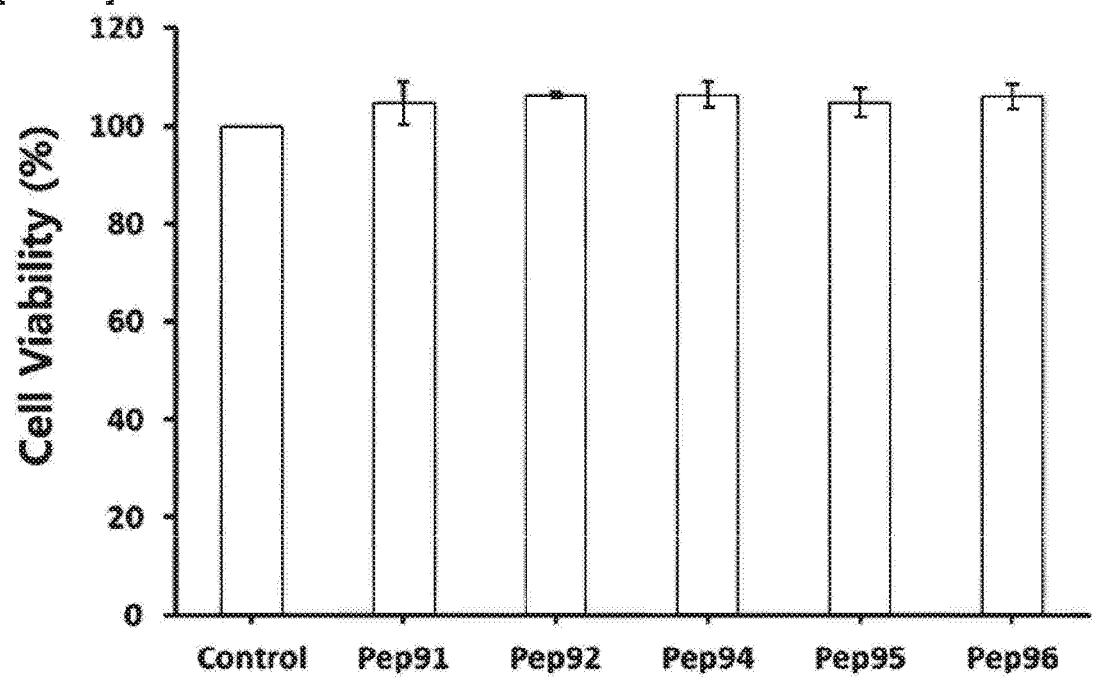
[FIG. 68]
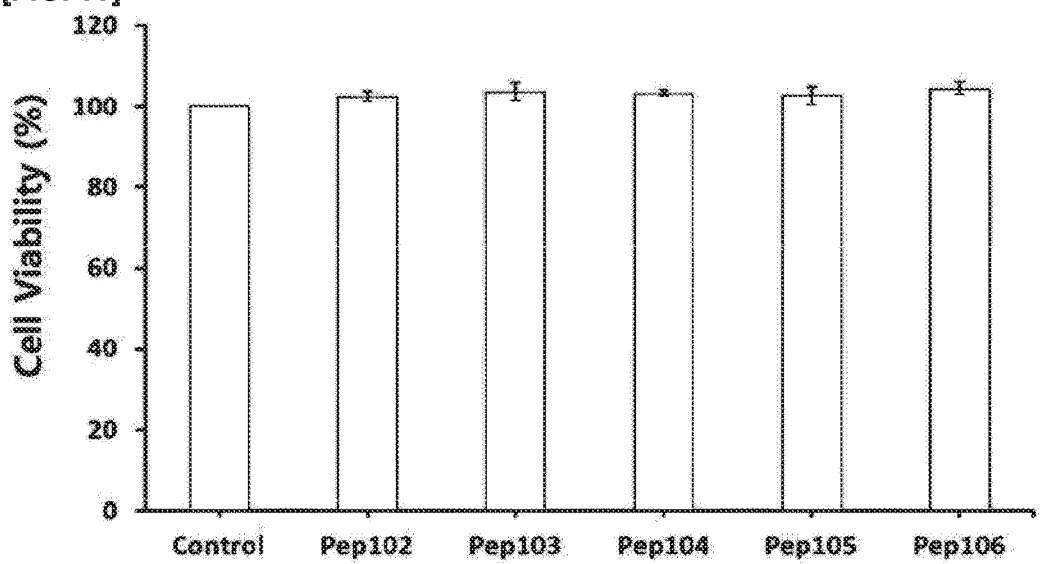
[FIG. 69]

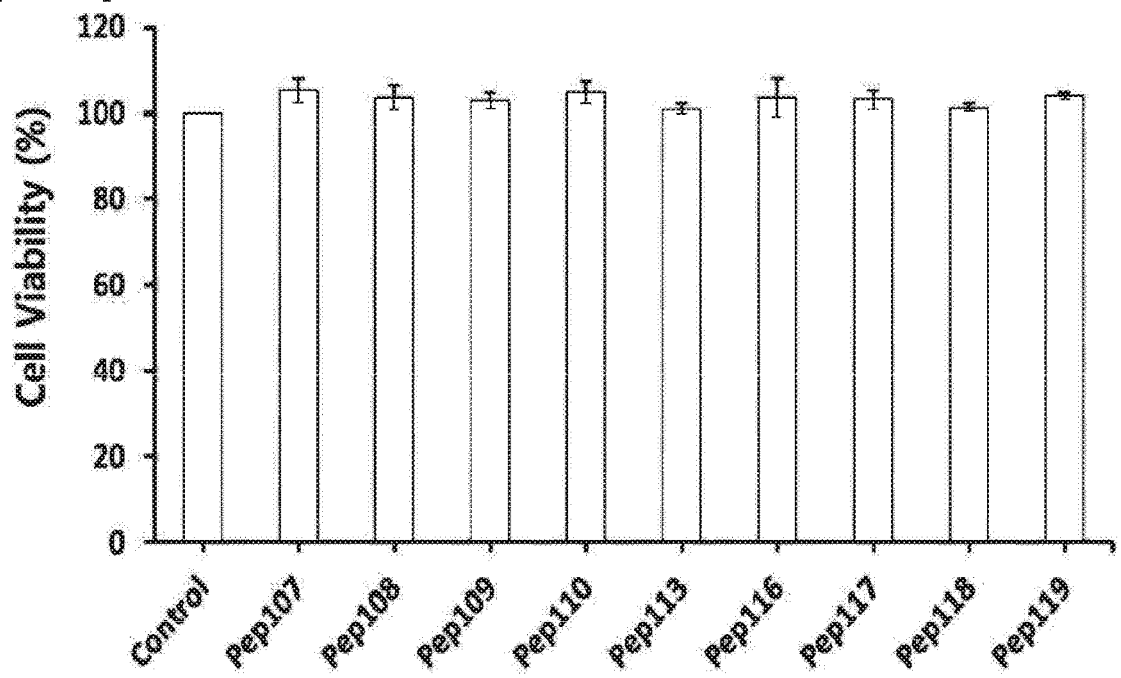
[FIG. 70]
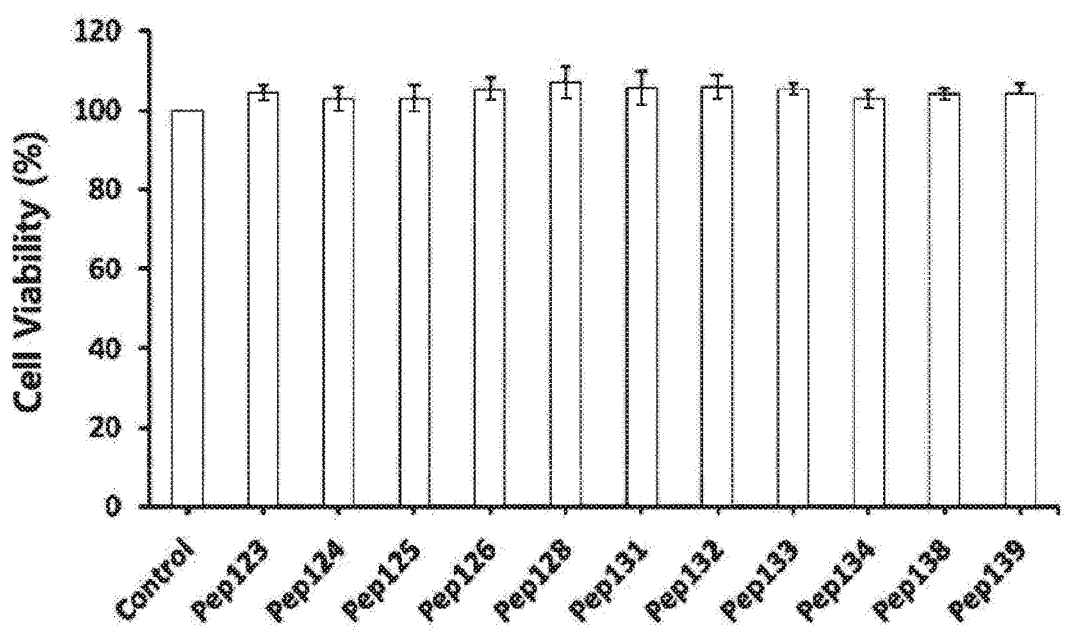
[FIG. 71]

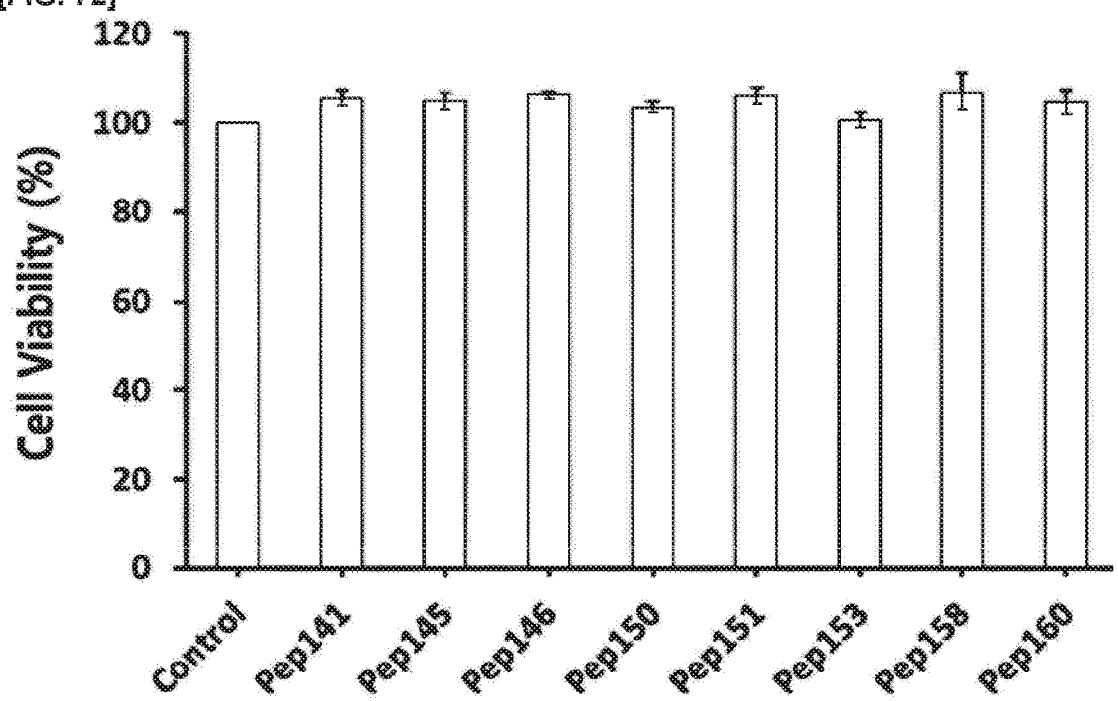
[FIG. 72]

1

CELL PENETRATING PEPTIDE, CONJUGATE COMPRISING SAME, AND COMPOSITION COMPRISING CONJUGATE

CROSS-REFERENCE TO RELATED APPLICATIONS

This application is a divisional application of U.S. application Ser. No. 15/869,518, filed on Jan. 12, 2018, which is a divisional application of U.S. application Ser. No. 14/429,637, filed Sep. 17, 2013, now U.S. Pat. No. 9,902,945, which is the National Stage of International Application No. PCT/KR2013/008438, filed Sep. 17, 2013, which claims the priority benefit of Korean Application Nos. 10-2013-0017169, filed Feb. 18, 2013; 10-2012-0109216, filed Sep. 28, 2012; 10-2012-0109207, filed Sep. 28, 2012; 10-2012-0104144, filed Sep. 19, 2012; and 10-2012-0104173, filed Sep. 19, 2012, each of which is hereby incorporated by reference herein in its entirety.

REFERENCE TO SEQUENCE LISTING

The Sequence Listing submitted Sep. 25, 2020, as a text file named "2473_0810007_Seq_Listing_ST25.txt", created on Sep. 24, 2020, and having a size of 49,017 bytes, is hereby incorporated by reference pursuant to 37 C.F.R. § 1.52(e)(5).

FIELD OF THE INVENTION

The present invention relates to cell penetrating peptides derived from human telomerase reverse transcriptase (hTERT) enzyme, conjugates of the cell penetrating peptides, active ingredients, and compositions comprising the conjugate.

BACKGROUND

Although Low-molecular weight substances, nucleic acids, proteins, nano-particles, etc, have great potentials as therapeutic substances at a molecular level, their uses are limited due to the incompetence to penetrate into tissues and cell membrane. The development of a system to deliver such substances into the cell has been the active area of research over the last two decades. transport the substances inside the cell has been a conversation topic in a treatment of molecular method. Low-molecular weight substances, nucleic acids or nano-particles were transported inside the cell by several reagents, electroporation or heatshock. However, it was difficult to find an adequate method of delivery of proteins inside the cell without disrupting the activity and integrity of proteins. In 1980s, in the research conducted on studying the cell penetrating capacity of HIV, it was found that HIV-TAT protein consisting of specific 11 amino acids play an important role in a process of transportation inside the cell. Thus, in 1990s, studies on finding the right method of transporting proteins inside the cell has been the intense area of research ….

Telomere is known as a repetitive sequence of genetic material found at the ends of chromosomes that prevent chromosomes from damage or merging onto other chromosomes. The length of the telomere is shortened at each cell division, and after a certain number of cell division, the telomere length is extremely shortened to the extent in which the cell stops dividing and dies. On the other hand, the elongation of telomeres is known to extend the life span of a cell. For an example, cancer cells excrete an enzyme called telomerase, which prevents shortening of telomeres, thus resulting in proliferation of cancer cells.

The objective of this invention is to provide a novel peptide.

Another objective of present invention is to provide the polynucleotide that codes the novel peptide.

Another objective of present invention is to provide a cell penetrating peptide.

Another objective of present invention is to provide a useful peptide as a carrier of the active ingredient in a cell.

Another objective of present invention is to provide a conjugate that an active ingredient and cell penetrating peptide are conjugated.

Another objective of present invention is to provide a composition comprising a conjugate of an active ingredient and cell penetrating peptide.

Another objective of present invention is to provide a pharmaceutical composition comprising a conjugate of an active ingredient and cell penetrating peptide.

Another objective of present invention is to provide a functional cosmetic composition comprising a conjugate of an active ingredient and cell penetrating peptide.

Another objective of present invention is to provide a health food composition comprising a conjugate of an active ingredient and cell penetrating peptide.

Another objective of present invention is to provide a contrast agent comprising a conjugate of an active ingredient and cell penetrating peptide.

SUMMARY OF THE INVENTION

The conjugate according to the one embodiment of the present invention may be a conjugate of cell penetrating carrier peptide and active ingredients, wherein the carrier peptide is the peptide comprising any one amino acid sequence of SEQ ID NO: 1 to SEQ ID NO: 156, the peptide having above 80% homology of amino acid sequence with above-mentioned sequences, or the fragment of the above-mentioned peptides, and wherein the peptide having above 80% homology of amino acid sequence with above-mentioned sequences and the fragment of the same are the peptides that maintain cell penetrating ability of any one amino acid sequences of 1 to SEQ ID NO: 156.

According to another embodiment of the conjugate in the present invention, the fragment may be made of 3 or more amino acids.

According to another embodiment of the conjugate in the present invention, the carrier peptide may be made of 30 or less amino acids.

According to another embodiment of the conjugate in the present invention, the above-mentioned carrier peptide may be the peptide having any one or more amino acid sequences of SEQ ID NO: 1 to SEQ NO: 156.

According to another embodiment of the conjugate in the present invention, which comprises any one amino acid sequence selected from the group consisting of: SEQ ID NO: 9, SEQ ID NO: 37, SEQ ID NO: 43, SEQ ID NO: 48, SEQ ID NO: 52, SEQ ID NO: 55. SEQ ID NO: 90, SEQ ID NO: 92 and SEQ ID NO: 121.

The contrast agent according to the one embodiment of the present invention may comprise any one conjugate above-mentioned.

The contrast agent according to the one embodiment of the present invention may be for contrasting a cell.

According to another embodiment of the contrast agent in the present invention, the cell may be a stem cell.

The composition according to one embodiment of the present invention may comprise any one of conjugates above-mentioned.

According to another embodiment of the composition in the present invention, the active ingredient may be for treatment or prevention of disease, and the composition may be pharmaceutical composition.

According to another embodiment of the composition in the present invention, the active ingredient may be the active ingredient for functional cosmetics, and the composition may be cosmetic composition.

According to another embodiment of the composition in the present invention, the active ingredient may be the active ingredient for functional health food, and the composition may be health food composition.

The cytoplasm targeting delivery system of active ingredient according to the one embodiment of the present invention may comprise any one of conjugates mentioned above, wherein the carrier peptide moves into a cytoplasm locally and performs a role of local cytoplasm delivering the mentioned active ingredients, wherein the peptide having above 80% homology of amino acid sequence with above-mentioned sequence and the fragment of the same are the peptides that maintain cell penetrating ability of any one amino acid sequences of SEQ ID NO: 1 to SEQ ID NO: 156.

According to another embodiment of the method in the present invention, the method may be for delivering the active ingredient locally into mitochondria inside a cell.

According to another embodiment of the cell penetrating peptide in the present invention, the above-mentioned carrier peptide may be the peptide having any one or more amino acid sequences of SEQ ID NO: 1 to SEQ ID NO: 156.

The polynucleotide according to the present invention may encode above-mentioned cell penetrating peptide.

The vector according to the present invention may comprise above-mentioned polynucleotide.

The transformed cell according to the present invention may comprise above-mentioned vector.

INDUSTRIAL APPLICABILITY

Active ingredients which are difficult to be transported inside a cell can be easily transported inside a cell by using the peptide, or the conjugate of the peptide and active ingredients, disclosed in the present invention. This means that efficacy of active ingredients can be increased and therefore the dosage can be lowered. As a result, side effects due to a drug administration can be minimized and effectiveness of treatment can be increased. Especially, as delivering drugs locally into mitochondria, mitochondria related diseases or disorders can be improved, and the effectiveness of prophylaxis and treatment of diseases can be increased. In a case of cosmetics, with a small amount of active ingredients, it can create an outstanding effect. By conjugating a peptide with a contrast substance, it can be used as a contrast substance to monitor a process of cell transplantation or transplanted cells in a cell treatment. Especially, it can be effectively used as a contrast substance for stem cells injected within a body.

BRIEF DESCRIPTION OF THE DRAWINGS

FIG. 1 to FIG. 23 represents illustrating that the cellular uptake of the cell numbers from a HeLa cell treated with after the FITC fused to the peptide of SEQ: 1 to SEQ ID NO: 156, and analyzed by FACS. The control cells were treated only FITC.

FIG. 24 to FIG. 43 represents illustrating that the cellular uptake of the cell numbers from a Hur7 cell treated with after the FITC fused to the peptide of SEQ: 1 to SEQ ID NO: 156, and analyzed by FACS. The control cells were treated only FITC.

FIG. 44 to FIG. 58 represents illustrating that the cellular uptake of the cell numbers from a human T lymphocyte cell line (Jurket) treated with after the FITC fused to the peptide of SEQ: 1 to SEQ ID NO: 156, and analyzed by FACS. The control cells were treated only FITC.

FIG. 59 to FIG. 72 represents illustrating that the result of toxicity and cell viability from a HeLa cell treated with after the FITC fused to the peptide of SEQ: 1 to SEQ ID NO: 156, and analyzed by flow cytometry (Flow cytometry). The control cells were treated only FITC.

DETAILED DESCRIPTION OF THE INVENTION

Proteins, Nucleic acids, Peptides or virus etc. have big potentials to be used as therapeutic substances. However, their uses are limited because they cannot penetrate tissues and cell membrane due to molecular level sizes. Although, the size of molecules is small, they cannot penetrate lipid-bilayer due to structure or characteristics of the molecules. Thus, through the use of electroporation, heat shock, etc., there were attempts to transport proteins, nucleic acids, peptides or viruses inside the cell; it was difficult to transfer those without neither damaging cell membrane nor keeping the active states of above molecules. There have been many studies conducted since TAT (Trans-Activating Transcriptional activator) protein derived from HIV (Human Immuno-deficiency Virus) has shown to work as cell penetrating peptide which can transport huge active substances inside the cell. Specifically, there have been studies conducted about substances that can transport huge molecules such as proteins, nucleic acids, peptides or virus inside the cell without causing any toxicity, unlike TAT protein which causes toxicity inside the cell. Therefore, the present invention was completed as present inventors have found that peptides derived from telomerase have outstanding efficacy as cell penetrating peptide without a noticeable toxicity.

Peptides are disclosed in SEQ NO: 1 to SEQ ID NO: 156 shown in Table 1 below. SEQ ID NO: 157 is a full length sequence of the Human telomerase protein. The "name" in Table 1 below was used for distinction of peptides. In a different specific embodiment of the present invention, more than one peptide of the mentioned peptides in SEQ ID NO: 1 to SEQ ID NO: 156 comprise a "synthetic peptide", a synthesized peptide of selected areas of the telomerase. In the present specification, the term "pep" herein relates to a peptide that has any one amino sequence among SEQ ID NO: 1 to SEQ ID NO: 156, or a peptide comprising of amino acid sequence above 80% homology with above-mentioned sequences, or a peptide fragment of above-mentioned peptides.

TABLE 1

| SEQ ID NO | NAME | Position in Telomerase Sequence | | Length |
|---|---|---|---|---|
| 1. | pep2 | [660-689] | ALFSVLNYERARRPGLLGASVLGLDDIHRA | 30 aa |
| 2. | pep3 | [663-677] | SVLNYERARRPGLLG | 15 aa |
| 3. | pep4 | [674-683] | GLLGASVLGL | 10 aa |
| 4. | pep5 | [615-624] | ALLTSRLRFI | 10 aa |
| 5. | pep6 | [613-621] | RPALLTSRL | 9 aa |
| 6. | pep7 | [653-661] | RLTSRVKAL | 9 aa |
| 7. | pep8 | [691-705] | RTFVLRVRAQDPPPE | 15 aa |
| 8. | pep9 | [653-667] | RLTSRVKALFSVLNY | 15 aa |
| 9. | pep10 | [651-665] | AERLTSRVKALFSVL | 15 aa |
| 10. | pep11 | [667-675] | YERARRPGL | 9 aa |
| 11. | pep12 | [675-683] | LLGASVLGL | 9 aa |
| 12. | pep13 | [680-689] | VLGLDDIHRA | 10 aa |
| 13. | pep14 | [677-686] | GASVLGLDDI | 10 aa |
| 14. | pep15 | [660-669] | ALFSVLNYER | 10 aa |
| 15. | pep16 | [663-672] | SVLNYERARR | 10 aa |
| 16. | pep17 | [679-688] | SVLGLDDIHR | 10 aa |
| 17. | pep18 | [662-671] | FSVLNYERAR | 10 aa |
| 18. | pep19 | [666-675] | NYERARRPGL | 10 aa |
| 19. | pep20 | [667-676] | YERARRPGLL | 10 aa |
| 20. | pep21 | [672-681] | RPGLLGASVL | 10 aa |
| 21. | pep22 | [668-676] | ERARRPGLL | 9 aa |
| 22. | pep23 | [680-688] | VLGLDDIHR | 9 aa |
| 23. | pep24 | [663-671] | SVLNYERAR | 9 aa |
| 24. | pep25 | [664-672] | VLNYERARR | 9 aa |
| 25. | pep26 | [670-678] | ARRPGLLGA | 9 aa |
| 26. | pep27 | [673-681] | PGLLGASVL | 9 aa |
| 27. | pep28 | [671-679] | RRPGLLGAS | 9 aa |
| 28. | pep29 | [660-668] | ALFSVLNYE | 9 aa |
| 29. | pep30 | [674-682] | GLLGASVLG | 9 aa |
| 30. | pep31 | [679-687] | SVLGLDDIH | 9 aa |
| 31. | pep32 | [668-675] | ERARRPGL | 8 aa |
| 32. | pep33 | [670-677] | ARRPGLLG | 8 aa |
| 33. | pep34 | [671-681] | GLLGASVL | 8 aa |
| 34. | pep35 | [669-676] | RARRPGLL | 8 aa |
| 35. | pep36 | [676-683] | LGASVLGL | 8 aa |
| 36. | pep37 | [563-577] | VTETTFQKNRLFFYR | 8 aa |
| 37. | pep38 | [573-587] | LFFYRKSVWSKLQSI | 15 aa |
| 38. | pep39 | [583-597] | KLQSIGIRQHLKRVQ | 15 aa |
| 39. | pep40 | [603-617] | EAEVRQHREARPALL | 15 aa |

TABLE 1-continued

| SEQ ID NO | NAME | Position in Telomerase Sequence | | Length |
|---|---|---|---|---|
| 40. | pep41 | [613-627] | RPALLTSRLRFIPKP | 15 aa |
| 41. | pep42 | [623-637] | FIPKPDGLRPIVNMD | 15 aa |
| 42. | pep43 | [643-657] | RTFRREKRAERLTSR | 15 aa |
| 43. | pep45 | [683-697] | LDDIHRAWRTFVLRV | 15 aa |
| 44. | pep46 | [693-707] | FVLRVRAQDPPPELY | 15 aa |
| 45. | pep47 | [721-735] | PQDRLTEVIASIIKP | 15 aa |
| 46. | pep48 | [578-592] | KSVWSKLQSIGIRQH | 15 aa |
| 47. | pep49 | [593-608] | LKRVQLRELSEAEVRQ | 16 aa |
| 48. | pep50 | [1-20] | MPRAPRCRAVRSLLRSHYRE | 20 aa |
| 49. | pep51 | [21-40] | VLPLATFVRRLGPQGWRLVQ | 20 aa |
| 50. | pep52 | [41-60] | RGDPAAFRALVAQCLVCVPW | 20 aa |
| 51. | pep53 | [61-80] | DARPPPAAPSFRQVSCLKEL | 20 aa |
| 52. | pep54 | [81-100] | VARVLQRLCERGAKNVLAFG | 20 aa |
| 53. | pep55 | [101-120] | FALLDGARGGPPEAFTTSVR | 20 aa |
| 54. | pep56 | [121-140] | SYLPNTVTDALRGSGAWGLL | 20 aa |
| 55. | pep57 | [141-160] | LRRVGDDVLVHLIARCALFV | 20 aa |
| 56. | pep58 | [161-180] | LVAPSCAYWVCGPPLYQLGA | 20 aa |
| 57. | pep59 | [181-200] | ATQARPPPHASGPRRRLGCE | 20 aa |
| 58. | pep60 | [201-220] | RAWNHSVREAGVPLGLPAPG | 20 aa |
| 59. | pep61 | [221-240] | ARRGGSASRSLPLPKRPRR | 20 aa |
| 60. | pep62 | [241-260] | GAAPEPERTPVGQGSWAHPG | 20 aa |
| 61. | pep63 | [261-280] | RTRGPSDRGFCVVSPARPAE | 20 aa |
| 62. | pep64 | [280-300] | EATSLEGALSGTRHSHPSVG | 20 aa |
| 63. | pep65 | [301-320] | RQHHAGPPSTSRPPRPWDTP | 20 aa |
| 64. | pep66 | [321-340] | CPPVYAETKHFLYSSGDKEQ | 20 aa |
| 65. | pep67 | [341-350] | LRPSFLLSSLRPSLTGARRL | 20 aa |
| 66. | pep68 | [361-380] | VETIFLGSRPWMPGTPRRLP | 20 aa |
| 67. | pep69 | [381-400] | RLPQRYWQMRPLFLELLGNH | 20 aa |
| 68. | pep70 | [401-420] | AQCPYGVLLKTHCPLRAAVT | 20 aa |
| 69. | pep71 | [421-440] | PAAGVCAREKPQGSVAAPEE | 20 aa |
| 70. | pep72 | [441-460] | EDTDPRRLVQLLRQHSSPWQ | 20 aa |
| 71. | pep74 | [481-500] | RHNERRFLRNTKKFISLGKH | 20 aa |
| 72. | pep75 | [501-520] | AKLSLQELTWKMSVRDCAWL | 20 aa |
| 73. | pep76 | [521-540] | RRSPGVGCVPAAEHRLREEI | 20 aa |
| 74. | pep77 | [541-560] | LAKFLHWLMSVYVVEGGRSF | 20 aa |
| 75. | pep78 | [561-580] | FYVTETTFQKNRLFFYRKSV | 20 aa |
| 76. | pep79 | [581-600] | WSKLQSIGIRQHLKRVQLRE | 20 aa |
| 77. | pep80 | [601-620] | LSEAEVRQHREARPALLTSR | 20 aa |

TABLE 1-continued

| SEQ ID NO | NAME | Position in Telomerase | Sequence | Length |
|---|---|---|---|---|
| 78. | pep81 | [621-640] | LRFIPKPDGLRPIVNMDYVV | 20 aa |
| 79. | pep82 | [641-660] | GARTFRREKRAERLTSRVKA | 20 aa |
| 80. | pep83 | [661-680] | LFSVLNYERARRPGLLGASV | 20 aa |
| 81. | pep85 | [701-720] | DPPPELYFVKVDVTGAYDTI | 20 aa |
| 82. | pep86 | [721-740] | PQDRLTEVIASIIKPQNTYC | 20 aa |
| 83. | pep87 | [741-760] | VRRYAVVQKAAHGEVRKAFK | 20 aa |
| 84. | pep88 | [761-780] | SHVSTLTDLQPYMRQFVAHL | 20 aa |
| 85. | pep89 | [781-800] | QETSPLRDAVVIEQSSSLNE | 20 aa |
| 86. | pep90 | [801-820] | ASSGLFDVFLRFMCHHAVRI | 20 aa |
| 87. | pep91 | [821-840] | RGKSYVQCQGIPQGSILSTL | 20 aa |
| 88. | pep92 | [841-860] | LCSLCYGDMENKLFAGIRRD | 20 aa |
| 89. | pep93 | [861-880] | GLLLRLVDDFLLVTPHLTHA | 20 aa |
| 90. | pep94 | [881-900] | KTFLRTLVRGVPEYGCVVNL | 20 aa |
| 91. | pep95 | [901-920] | RKTVVNFPVEDEALGGTAFV | 20 aa |
| 92. | pep96 | [921-940] | QMPAHGLFPWCGLLLDTRTL | 20 aa |
| 93. | pep97 | [941-960] | EVQSDYSSYARTSIRASLTF | 20 aa |
| 94. | pep99 | [981-1000] | KCHSLFLDLQVNSLQTVCTN | 20 aa |
| 95. | pep100 | [1001-1020] | IYKILLLQAYRFHACVLQLP | 20 aa |
| 96. | pep101 | [1021-1040] | FHQQVWKNPTFFLRVISDTA | 20 aa |
| 97. | pep102 | [1041-1060] | SLCYSILKAKNAGMSLGAKG | 20 aa |
| 98. | pep103 | [1061-1080] | AAGPLPSEAVQWLCHQAFLL | 20 aa |
| 99. | pep104 | [1081-1100] | KLTRHRVTYVPLLGSLRTAQ | 20 aa |
| 100. | pep105 | [1101-1120] | TQLSRKLPGTTLTALEAAAN | 20 aa |
| 101. | pep106 | [1121-1132] | PALPSDFKTILD | 20 aa |
| 102. | pep107 | [1-10] | MPRAPRCRAV | 10 aa |
| 103. | pep108 | [11-30] | RSLLRSHYREVLPLATFVRR | 20 aa |
| 104. | pep109 | [31-50] | LGPQGWRLVQRGDPAAFRAL | 20 aa |
| 105. | pep110 | [51-70] | VAQCLVCVPWDARPPPAAPS | 20 aa |
| 106. | pep111 | [71-90] | FRQVSCLKELVARVLQRLCE | 20 aa |
| 107. | pep112 | [91-110] | RGAKNVLAFGFALLDGARGG | 20 aa |
| 108. | pep113 | [111-130] | PPEAFTTSVRSYLPNTVTDA | 20 aa |
| 109. | pep114 | [131-150] | LRGSGAWGLLLRRVGDDVLV | 20 aa |
| 110. | pep115 | [151-170] | HLLARVALFVLVAPSCAYQV | 20 aa |
| 111. | pep116 | [171-190] | CGPPLYQLGAATQARPPPHA | 20 aa |
| 112. | pep117 | [191-210] | SGPRRRLGCERAWNHSVREA | 20 aa |
| 113. | pep118 | [211-230] | GVPLGLPAPGARRRGGSASR | 20 aa |
| 114. | pep119 | [231-250] | SLPLPKRPRRGAAPEPERTP | 20 aa |
| 115. | pep120 | [251-270] | VGQGSWAHPGRTRGPSDRGF | 20 aa |
| 116. | pep121 | [271-290] | CVVSPARPAEEATSLEGALS | 20 aa |

TABLE 1-continued

| SEQ ID NO | NAME | Position in Telomerase Sequence | | Length |
|---|---|---|---|---|
| 117. | pep122 | [291-310] | GTRHSHPSVGRQHHAGPPST | 20 aa |
| 118. | pep123 | [311-330] | SRPPRPWDTPCPPVYAETKH | 20 aa |
| 119. | pep124 | [331-350] | FLYSSGDKEQLRPSFLLSSL | 20 aa |
| 120. | pep125 | [351-370] | RPSLTGARRLVETIFLGSRP | 20 aa |
| 121. | pep126 | [371-390] | WMPGTPRRLPRLPQRYWQMR | 20 aa |
| 122. | pep127 | [391-410] | PLFLELLGNHAQCPYGVLLK | 20 aa |
| 123. | pep128 | [411-430] | THCPLRAAVTPAAGVCAREK | 20 aa |
| 124. | pep129 | [431-450] | PQGSVAAPEEEDTDPRRLVQ | 20 aa |
| 125. | pep130 | [451-470] | LLRQHSSPWQVYGFVRACLR | 20 aa |
| 126. | pep131 | [471-490] | RLVPPGLWGSRHNERRFLRN | 20 aa |
| 127. | pep132 | [491-510] | TKKFISLGKHAKLSLQELTW | 20 aa |
| 128. | pep133 | [511-530] | KMSVRDCAWLRRSPGVGCVP | 20 aa |
| 129. | pep134 | [531-550] | AAEHRLREEILAKFLHWLMS | 20 aa |
| 130. | pep135 | [551-570] | VYVVELLRSFFYVTETTFQK | 20 aa |
| 131. | pep136 | [571-590] | NRLFFYRKSVWSKLQSIGIR | 20 aa |
| 132. | pep137 | [591-610] | QELKRVQLRELSEAEVRQHR | 20 aa |
| 133. | pep138 | [611-630] | EARPALLTSRLRFIPKPDGL | 20 aa |
| 134. | pep139 | [631-650] | RPIVNMDYVVGARTFRREKR | 20 aa |
| 135. | pep140 | [651-670] | AERLTSRVKALFSVLAYERA | 20 aa |
| 136. | pep141 | [671-690] | RRPGLLGASVLGLDDIHRAW | 20 aa |
| 137. | pep142 | [691-710] | RTFVLRVRAQDPPPELYFVK | 20 aa |
| 138. | pep143 | [711-730] | VDVTGAYDTIPQDRLTEVIA | 20 aa |
| 139. | pep145 | [751-770] | AHGHVRKAFKSHVSTLTDLQ | 20 aa |
| 140. | pep146 | [771-790] | PYMRQFVAHLQETSPLRDAV | 20 aa |
| 141. | pep147 | [791-810] | VIEQSSSLNEASSGLFDVFL | 20 aa |
| 142. | pep148 | [811-830] | RFMCHHAVRIRGKSYVQCQG | 20 aa |
| 143. | pep149 | [831-850] | IPQGSILSTLLCSLCYGDME | 20 aa |
| 144. | pep150 | [851-870] | NKLFAGIRRDGLLLRLVDDF | 20 aa |
| 145. | pep151 | [871-890] | LLVTPHLTHAKTFLRLTVRG | 20 aa |
| 146. | pep152 | [891-910] | VPEYGCVVNLRKTVVNFPVE | 20 aa |
| 147. | pep153 | [911-930] | DEALGGTAFVQMPAHGLFPW | 20 aa |
| 148. | pep154 | [931-950] | CGLLLDTRTLEVQSDYSSYA | 20 aa |
| 149. | pep156 | [971-990] | RRKLFGVLRLKCHSLFLDLQ | 20 aa |
| 150. | pep157 | [991-1010] | VNSLQTVCTNIYKILLLQAY | 20 aa |
| 151. | pep158 | [1011-1030] | RFHACVLQLPFHQQVWKNPT | 20 aa |
| 152. | pep159 | [1031-1050] | FFLRVISDTASLCYSILKAK | 20 aa |
| 153. | pep160 | [1051-1070] | NAGMSLGAKGAAGPLPSEAV | 20 aa |
| 154. | pep161 | [1071-1090] | QWLCHQAFLLKLTRHRVTYV | 20 aa |

TABLE 1-continued

| SEQ ID NO | NAME | Position in Telomerase | Sequence | Length |
|---|---|---|---|---|
| 155. | pep162 | [1091-1110] | PLLGSLRTAQTQLSRKLPGT | 20 aa |
| 156. | pep163 | [1111-1132] | TLTALEAAANPALPSDFKTILD | 20 aa |
| 157. | Telomerase | [1-1132] | MPRAPRCRAVRSLLRSHYREVLPLATFVRRLGPQGWRL VQRGDPAAFRALVAQCLVCVPWDARPPPAAPSFRQVSC LKELVARVLQRLCERGAKNVLAFGFALLDGARGGPPEA FTTSVRSYLPNTVTDALRGSGAWGLLLRRVGDDVLVHL LARCALFVLVAPSCAYQVCGPPLYQLGAATQARPPPHA SGPRRRLGCERAWNHSVREAGVPLGLPAPGARRRGGSA SRSLPLPKRPRRGAAPEPERTPVGQGSWAHPGRTRGPS DRGFCVVSPARPAEEATSLEGALSGTRHSHPSVGRQHH AGPPSTSRPPRPWDTPCPPVYAETKFLYSSGDKEQLRP SFLLSSLRPSLTGARRLVETIFLGSRPWMPGTPRRLPR LPQRYWQMRPLFLELLGNHAQCPYGVLLKTHCPLRAAV TPAAGVCAREKPQGSVAAPEEEDTDPRRLVQLLRQHSS PWQVYGFVRACLRRLVPPGLWGSRHNERRFLRNTKKFI SLGKHAKLSLQELTWKMSVRDCAWLRRSPGVGCVPAAE HRLREEILAKFLHWLMSVYVVELLRSFFYVTETTFQKN RLFFYRKSVWSKLQSIGIRQELKRVQLRELSEAEVRQH REARPALLTSRLRFIPKPDGLRPIVNMDYVVGARTFRR EKRAERLTSRVKALFSVLNYERARRPGLLGASVLGLDD IHRAWRTFVLRVRAQDPPPELYFVKVDVTGAYDTIPQD RLTEVIASIIKPQNTYCVRRYAVVQKAAHGHVRKAFKS HVSTLTDLQPYMRQFVAHLQETSPLRDAVVIEQSSSLN EASSGLFDVFLRFMCHHAVRIRGKSYVQCQGIPQGSIL STLLCSLCYGDMENKLFAGIRRDGLLLRLVDDFLLVTP HLTHAKTFLRTLVRGVPEYGCVVNLRKTVVNFPVEDEA LGGTAFVQMPAHGLFPWCGLLLDTRTLEVQSDYSSYAR TSIRASLTFNRGFKAGRNMRRKLFGVLRLKCHSLFLDL QVNSLQTVCTNIYKILLLQAYRFHACVLQLPFHQQVWK NPTFFLRVISDTASLCYSILKAKNAGMSLGAKGAAGPL PSEAVQWLCHQAFLLKLTRHRVTYVPLLGSLKRTAQTQ LSRKLPGTTLTALEAAANPALPSDFKTILD | 1132 |
| 164 | pep1 | [611-626] | EARPALLTSRLRFIPK | 16 aa |

In one embodiment of the present invention the polynucleotide codes a peptide comprising at least one amino acid sequence of SEQ ID NO: 1 to SEQ ID NO: 156, a peptide having above 80% homology with above-mentioned sequences, or a peptide being a fragment of the above-mentioned peptides. The polynucleotide mentioned above enables production of the peptides in large quantities. For example, cultivation of vectors that include polynucleotides encoding peptides allows production of peptides in large quantities.

The peptides disclosed herein can include a peptide comprising amino acid sequence above 80%, above 85%, above 90%, above 95%, above 96%, above 97%, above 98%, or above 99% homology. Moreover, the peptides disclosed in the present invention can include a peptide comprising any one amino sequence among SEQ ID NO: 1 to SEQ ID NO: 156 or its fragments, and a peptide with more than 1 transformed amino acid, more than 2 transformed amino acid, more than 3 transformed amino acid, more than 4 transformed amino acid, more than 5 transformed amino acid, more than 6 transformed amino acid, or more than 7 transformed amino acid.

In one embodiment of the present invention, changes in amino acid sequence belong to the modification of peptide's physical and chemical characteristics. For example, amino acid transformation can be performed by improving thermal stability of the peptide, altering substrate specificity, and changing the optimal pH.

The term "amino acid" herein includes not only the 22 standard amino acids that are naturally integrated into peptide but also the D-isomers and transformed amino acids. Therefore, in a specific embodiment of the present invention, a peptide herein includes a peptide having D-amino acids. On the other hand, a peptide may include non-standard amino acids such as those that have been post-translationally modified. Examples of post-translational modification include phosphorylation, glycosylation, acylation (including acetylation, myristorylation, plamitoylation), alkylation, carboxylation, hydroxylation, glycation, biotinylation, ubiquitinylation, transformation in chemical properties (e.g. β-removing deimidation, deamidation) and structural transformation (e.g. formation of disulfide bridge). Also, changes of amino acids are included and the changes of amino acids occur due to chemical reaction during the combination process with crosslinkers for formation of a peptide conjugate.

A peptide disclosed herein may be a wild-type peptide that has been identified and isolated from natural sources. On the other hand, when compared to peptide fragments of any one amino sequence among SEQ ID NO: 1 to SEQ ID NO: 156, the peptides disclosed herein may be artificial mutants that comprise one or more substituted, deleted and/or inserted amino acids. Amino acid alteration in wild-type polypeptide—not only in artificial mutants—comprises conservative substitution of amino acids that do not influence protein folding and or activation. Examples of conservative substitution belong to the group consisting of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activity are known in the art of the present invention. Most common occurred alteration are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations. Another example of conservative substitutions are shown in the following table 2.

TABLE 2

| Original amino acid | Examples of residue substitution | Preferable residue substitution |
| --- | --- | --- |
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | ala | Ala |
| Ser (S) | thr | Thr |
| Thr (T) | ser | Ser |
| Trp (W) | tyr; phe | Tyr |
| Tyr (Y) | trp; phe; thr; ser | Phe |
| Val (V) | ile; leu; met; phe; ala; norleucine | Leu |

The substantial transformation of the biological properties of peptides are performed by selecting significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in the target area, or (c) the efficacy of maintaining the bulk of the side chain. Natural residues are divided into groups by general side chain properties as the following:
(1) hydrophobicity: Norleucine, met, ala, val, leu, ile;
(2) neutral hydrophilicity: cys, ser, thr;
(3) acidity: asp, glu;
(4) basicity: asn, gln, his, lys arg;
(5) residue that affects chain orientation: gly, pro; and
(6) aromaticity: trp, tyr, phe.

Non-conservative substitutions may be performed by exchanging a member of the above classes to different classes. Any cystein residues that are not related in maintaining the proper three-dimensional structure of the peptide can typically be substituted into serine, thus increasing the oxidative stability of the molecule and preventing improper crosslinkage. Conversely, improvement of stability can be achieved by adding cysteine bond(s) to the peptide.

Altered types of amino acids variants of peptides are those that antibody glycosylation pattern changed. The term "change" herein relates to deletion of at least one carbohydrate residues that are found in a peptide and/or addition of at least one glycosylated residues that do not exist within a peptide Glycosylation in peptides are typically N-connected or O-connected. The term "N-connected" herein relates to that carbohydrate residues are attached to the side chain of asparagine residues. As tripeptide sequences, asparagine-X-serine and asparagine-X-threonine (where the X is any amino acid except proline) are the recognition sequence for attaching carbohydrate residue enzymatically to the side chain of asparagine. Therefore, with the presence of one of these tripeptide sequences in a polypeptide, the potential glycosylation sites are created. "O-connected glycosylation" means attaching one of sugar N-acetylgalactosamine, galactose, or xylose to hydroxyl amino acids. The hydroxyl amino acids are most typically serine or threonine, but 5-hydroxyproline or 5-hydroxylysine can be used.

Addition of glycosylation site to a peptide is conveniently performed by changing amino acid sequence to contain tripeptide sequence mentioned above (for N-linked glycosylation sites). These changes may be made by addition of at least one serine or threonine residues to the first antibody sequence, or by substitution with those residues (for O-linked glycosylation sites).

In one embodiment of the present invention, cell penetrating peptide comprising any one amino acid sequences of SEQ ID NO: 1 to SEQ ID NO: 156, a peptide having above 80% homology of amino acid sequence with above-mentioned sequences, or a fragment of the above-mentioned peptides, is provided.

In one embodiment of the present invention, a pharmaceutical composition comprising peptide as a drug delivery system to transport more than one active ingredient is provided, wherein the pepdite comprises any one amino acid sequence of SEQ ID NO: 1 to SEQ ID NO: 156, the peptide has above 80% homology with above-mentioned sequence, or the peptide is a fragment of above-mentioned peptide.

A peptide comprising any one amino acid sequence of SEQ ID NO: 1 to SEQ ID NO: 156, a fragment of above-mentioned peptide, or a peptide having above 80% homology with above-mentioned sequence, is safe and has outstanding efficacy as cell penetrating peptide. Therefore, the peptide can be conjugated with a drug to transport the drug inside the cell.

In one embodiment of the present invention, a conjugate of a peptide and an active ingredient to be transported is provided, wherein the peptide comprises any one amino acid sequence of SEQ ID NO: 1 to SEQ ID NO: 156, the peptide is a fragment of above-mentioned peptide, or the peptide has above 80% homology with above-mentioned peptide, in one embodiment of the present invention, an active ingredient may be at least one selected from proteins, nucleic acids, peptides, lipids, glycolipids, minerals, sugars, contrast substances, drugs and chemical compounds. In one embodiment of the present invention, the active ingredients may be peptides. In one embodiment of the present invention, the active ingredients may be cytokines, antibody, antibody fragments, therapeutic enzymes, soluble receptors, or ligands.

A cell penetrating peptide disclosed herein means a peptide which can transport cargo from in vitro and/or in vivo to inside the cell. A "cargo" disclosed herein comprises all the substances that can be transported inside the cell via conjugation with a cell penetrating peptide. For example, all the substances which want to increase cell penetrating efficacy, specifically drugs, cosmetics, or active ingredients of health food, more specifically substances which cannot be transported inside the cell via general route, more specifically, sugars, nano-particles, biological formulation, viruses, contrast substances or other chemical compounds which can have proteins, nucleic acids, peptide, minerals, glucose as an example, but not limited to those. A "drug" disclosed herein is a broad concept including a substance to be transported for alleviation, prophylaxis, treatment or diagnosis of diseases, wounds, or specific symptom.

A "carrier peptide" disclosed herein is a peptide which can transport active ingredients to a targeted site via conjugation with active ingredients.

In one embodiment of the present invention, protein or peptide as a cargo comprises one or more of hormone, hormone analogue, enzyme, enzyme inhibitors, signal transfer proteins (or peptides), antibody and vaccine, but not limited to those. In one embodiment of the present invention, a nucleic acid is a molecule that can be spontaneous or artificial DNA or RNA molecules, either single-stranded or double-stranded. The nucleic acid molecule can be one or more nucleic acids of same type (for example, having a same nucleotide sequence) or nucleic acids of different types. The nucleic acid molecules comprise one or more DNA, cDNA, decoy DNA, RNA, siRNA, miRNA shRNA, stRNA, snoRNA, snRNA PNA, antisense oligomer, plasmid and other modified nucleic acids, but not limited to those. In one embodiment of the present invention, virus comprises the whole virus or the core of virus which includes nucleic acids of the virus. In one embodiment of the present invention, a chemical substance is a broad indication comprising a natural or synthetic substance which can act as a drug.

In one embodiment of the present invention, drug to be delivered into cells by a cell-permeable peptide is iposomes, micelles, nanoparticles, or quantum dots as drug delivery.

The term "contrast substance" disclosed herein is a broad indication comprising all the substances used to contrast structures or fluids within the body in medical imaging. An appropriate contrast substance comprises radiopaque contrast agent, paramagnetic contrast agent, superparamagnetic contrast agent, CT (computed tomography) and other contrast substances, but not limited to those. For example, a radiopaque contrast agent (for x-ray imaging) will comprise inorganic iodine compound and organic iodine compound (for example, diatrizoate), radiopaque metals and their salts (for example, silver, gold, platinum, etc.) and other radiopaque compounds (for example, calcium salts, barium salt such as barium sulfate, tantalum and oxidized tantalum). An appropriate paramagnetic contrast substance (for MR imaging) comprises gadolinium diethylene triaminepentaacetic acid (Gd-DTPA) and its derivatives, other gadolinium, manganese, iron, dysprosium, copper, europium, erbium, chrome, nickel and cobalt complex, for example, 1,4,7,10-tetraazacyclododecan-N,N',N",N'''-tetraacetic acid (DOTA), ethylenediaminetetraacetic acid (EDTA), 1,4,7,10-tetraazacyclododecan-N,—N',N"-triacetic acid (DO3A), 1,4,7-triazacyclononane-N,N',N"-TRIACETIC ACID (NOTA), 1,4,8,10-tetraazacyclotetradecane-N,N',N",N'''-tetraacetic acid (TETA), hydroxybenlethylene-diamine diacetic acid (HBED). An appropriate superparamagnetic contrast substance (for MR imaging) comprises magnetite, super-paramagnetic iron oxide (SPIO), ultrasmall superparamagnetic iron oxide (USPIO) and monocrystailine iron oxide. Other appropriate contrast substances are iodinated, non-iodinated, ionic and non-ionic CT contrast agents, a contrast substance like spin-label or diagnostically effective agent.

Other examples of contrast substances comprise β-galactosidase, Green Fluorescent Protein, Cyan Fluorescent Protein, luciferase, but not limited to those, and a marker gene which codes for protein which can be easily detected when expressed within cells. Various labels such as radionuclide, flour, enzyme, enzyme-substrate, enzyme cofactor, enzyme inhibitor, ligands (especially hapten) can be used.

In one example of the present invention, a contrast substance is ferrocenecarboxylic acid of the below chemical formula 2, The structure of ferrocene is shown in the chemical formula 1.

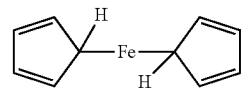

[Chemical Formula 1]

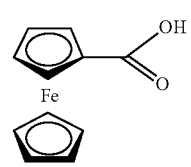

[Chemical formula 2]

In one example of the present invention, a conjugate of cell penetrating peptide and a contrast substance is Ferrocenecarboxylic-pep (Ferrocenecarboxylic-pep) shown in the below chemical formula 3.

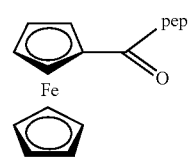

[Chemical formula 3]

In one embodiment of the present invention, a peptide or composition can be fused with one or more detectable labels. Labels may be compounds which can be detected in chemical, physical or enzymatic responses, or compounds which generate signals directly or indirectly in the responses. Labeling and detecting after then can be performed according to the known method in the art (For example, Sambrook, J., and Russel, D. W. (2001); and Lottspeich, F., and Zorbas H. (1998) Bioanalytik, Spektrum Akademischer Verlag, Heidelberg/Berlin, Germany). Labels comprise fluorescent label, enzyme label, chromogenic label, luminescence label, radiation label, hapten, biotin, metal complex, metal and colloidal gold, but not limited to those. All forms of these labels are well known in this field of work, they can be commercially obtained from various suppliers.

In one embodiment of the present invention, a cargo can be directly combined with the peptide. In another embodiment of the present invention, a cargo can be combined to the peptide via various types of bonds such as covalent or non-covalent bonds. A cargo, for example, can be combined to the N-terminal or C-terminal of the peptide in one embodiment of the present invention. For example, a cargo can be bonded to the peptide by disulfide bonds or covalent bonds. The covalent bonds are the bonds that a cargo can be bonded to α-amine of N-terminal glutamate, or amine of C-terminal Lysine residues. Also, a peptide and a cargo can be combined via a non-covalent bond, which can have either a peptide or a cargo can encapsulate the other as a capsule form.

In another embodiment of the present invention, a peptide can be combined with a cargo via a linker. For example, a peptide can be combined with a cargo by binding a cargo to a linker after introducing a linker such as Hynic (6-hydrazinopyridine-3-carboxylic acid) linker, to the α-amine of N-terminal glutamate, or amine of C-terminal Lysine residues.

In another embodiment of the present invention, when a cargo is DNA or RNA, SH group (thiol group) is introduced to the peptide, and maleimide group is introduced to DNA or RNA, then, SH group of the peptide and maleimide group of DNA or RNA are combined, thus creating a bond between the cargo and the peptide.

In another embodiment of the present invention, when a cargo is a peptide or protein, DNA which expresses a cargo is combined with DNA which expresses a carrier peptide, and by expressing this, a cargo and a peptide can be combined as a form of fusion protein. Specific examples of combination by a fusion protein are as follows: when manufacturing primer for production of fusion protein, a nucleotide coding a carrier peptide is attached in front of a nucleotide expressing a cargo, and the obtained nucleotide is inserted to a vector such as pET vector using a restriction enzyme, and the nucleotide is expressed by transformation into a cell such as BL-21(DE3). At this time, a fusion protein is to be effectively expressed by treating it with an expression inducing agent like IPTG (isopropyl-1-thio-β-D-galactopyranoside). Then, the expressed fusion protein is purified by His tag purification, and is dialyzed with PBS, and is added to a kit to be concentrated by centrifugation under such condition for 5 to 20 mins at 2,000 to 4,000 rpm.

In one embodiment of the present invention, a carrier peptide is combined with dying substances, fluorescent substances, specifically FITC (fluorescein isothiocyanate) or GFP (Green Fluorescent Protein). In one embodiment of the present invention, FITC is combined with amino group ($NH^{3+}$) of lysine at N-terminal or C-terminal of a carrier peptide. In the case of a peptide, where lysine does not exist at its terminal, the peptide can be combined with FITC via a linker including Lysine.

The carrier peptide disclosed herein which is the peptide comprising any one amino acid sequence of SEQ ID NO: 1 to SEQ ID NO: 156, or the peptide having above 80% homology of amino acid sequence with above-mentioned peptides, or a fragment of above-mentioned peptide, can be combined with a cargo at a mole fraction of 1:1, but it can be combined at mole fraction other than 1:1. For example, a mole fraction of CPP and a cargo may be more than 2:1, specifically, more than 2:1, more than 3:1, more than 4:1, more than 5:1, more than 6:1, more than 7:1, more than 8:1, more than 9:1 or more than 10:1. This means that numerous carrier peptide molecules can be combined with a cargo molecule. The numerous carrier peptide molecules can be combined in series or in parallel. "Combined in series" means that a carrier peptide and a cargo molecule are to be combined at terminal amino acids. "Combined in parallel" means that they are to be combined at a site other than terminal amino acids. On the other hand, the mole fraction of a carrier peptide and a cargo may be more than 1:2. This means that a carrier peptide molecule can be combined with numerous number of a cargo molecule. For example, a mole fraction of a carrier peptide and a cargo may be 1:2, specifically, more than 1:2, more than 1:3, more than 1:4, more than 1:5, more than 1:6, more than 1:7, more than 1:8, more than 1:9 or more than 1:10.

A movement pathway of the peptide combined with Fluorescein isothiocyanate can be easily found. Therefore, a carrier peptide in one embodiment of the present invention is to be used for cell imaging or detecting a pathway of drug delivery inside a cell.

In one embodiment of the present invention, a use of the peptide as a drug delivery carrier to transport more than one active ingredient is provided, wherein the peptide comprises any one amino acid sequence of SEQ ID NO: 1 to SEQ ID NO: 156, or the peptide is a fragment of above-mentioned peptide, or the peptide has above 80% homology of amino acid sequence with above-mentioned peptide. The use may indicate therapeutic or non-therapeutic use.

In one embodiment of the present invention, a method of delivering drugs inside a cell of a subject comprising a step of administering a composition comprising a drug; and the peptide is provided; wherein the peptide comprises any one amino acid sequence of SEQ ID NO: 1 to SEQ ID NO: 156, or the peptide is a fragment of above-mentioned peptide, or the peptide has above 80% homology of amino acid sequence with above-mentioned peptide.

In one embodiment of the present invention, a method of detecting drug delivery pathway comprising a step of applying the peptide and a contrast substance to a subject is provided; wherein the peptide comprises any one amino acid sequence of SEQ ID NO: 1 to SEQ ID NO: 156, or the peptide is a fragment of above-mentioned peptide, or the peptide has above 80% homology of amino acid sequence with above-mentioned peptide.

In one embodiment of the present invention, a method of detecting drug delivery pathway comprising a step of applying of the conjugate of the peptide and a contrast substance to a subject is provided; wherein the peptide comprises any one amino acid sequence of SEQ ID NO: 1 to SEQ ID NO: 156, or the peptide is a fragment of above-mentioned peptide, or the peptide has above 80% homology of amino acid sequence with above-mentioned peptide.

In one embodiment of the present invention, a kit for drug delivery into a cell of a subject containing the composition and an instruction is provided, wherein the composition comprises a conjugate of a peptide of the invention and a drug for delivery, wherein the peptide comprises any one amino acid sequence of SEQ ID NO: 1 to SEQ ID NO: 156 or the peptide is a fragment of above-mentioned peptide, or the peptide has above 80% homology of amino acid sequence with above-mentioned peptide, wherein the instruction includes at least one of administration dose, administration route, administration frequency, and indication of the composition.

In one embodiment of the present invention, cosmetic or food composition comprising an active ingredient; and the peptide is provided; wherein the peptide comprises amino acid sequence of SEQ ID NO: 1 to SEQ ID NO: 156, the peptide has above 80% homology of amino acid sequence with above-mentioned sequence, or the peptide is a fragment of the above-mentioned peptides. In another embodiment of the present invention, cosmetic or food composition comprising a conjugate of the peptide and active ingredients is provided; wherein the peptide comprises any one amino acid sequence of SEQ ID NO: 1 to SEQ ID NO: 156, the peptide has above 80% homology of amino acid sequence with above-mentioned sequence, or the peptide is a fragment of the above-mentioned peptides.

In one embodiment of the present invention, pharmaceutical, cosmetic or food composition with an outstanding ability to transport active ingredients inside a cell, comprising a conjugate of the peptide and an active ingredient, is provided; wherein the peptide comprises any one amino acid sequence of SEQ ID NO: 1 to SEQ ID NO: 156, the peptide has above 80% homology of amino acid sequence with above-mentioned sequence, or the peptide is a fragment of the above-mentioned peptides.

Mitochondria, as a central organelle in energy metabolism of a eukaryotic cell, is a first known intracellular organelle to be related to human diseases (Lull R, Ikkos D, Palmieri G, Ernster L, Afzelius B: A case of severe hypermetabolism of non thyroid origin with a defect in the maintenance of mitochondrial respiratory control: a correlated clinical, biochemical, and morphological study, J Clin Invest 41: 1776-804, 1962).

Since the mitochondria play an important role in control of energy metabolism of cell and apoptosis, they act as a major target for various therapeutic drugs. Also, this organelle is involved in control of the calcium concentration inside the cell, the mitochondrial respiratory chain acts as an electron transport system which is important in energy production, and it causes production of reactive oxygen species. As a result, the abnormal mitochondrial function has a close relationship with adult diseases such as diabetes, cardiomyopathy, infertility, blindness, renal/liver diseases, and stroke (Modica-Napolitano K S, Singh K K: April mitochondria as targets for detection and treatment of cancer. Expert Rev Mol Med 11:1-19, 2002). Also, it is being suggested that Mitochondrial genetic mutations to be involved in the outbreak of aging, degenerative neuronal disease and cancer etc.

The mitochondria targeting delivery system can be provided according to the one embodiment of the present invention may comprise any one of conjugates mentioned above, wherein the carrier peptide moves into intracellular mitochondria locally and performs a role of local intracellular mitochondria delivering the mentioned active ingredients, wherein the peptide having above 80% homology of amino acid sequence with above-mentioned sequence and the fragment of the same are the peptides that maintain mitochondria targeting delivery system, the above-mentioned mitochondria targeting peptide may be the peptide having any one amino acid sequences of SEQ ID NO: 1 to SEQ ID NO: 156.

The mitochondria activity adjusting composition can be provided, wherein the composition comprises a conjugate of a peptide of the invention and a carrier peptide for delivery, wherein the carrier peptide moves into intracellular mitochondria locally and performs a role of local intracellular mitochondria delivering the mentioned active ingredients, wherein the peptide having above 80% homology of amino acid sequence with above-mentioned sequence and the fragment of the same are the peptides that maintain mitochondria targeting delivery system, the above-mentioned mitochondria targeting peptide may be the composition having any one amino acid sequences of SEQ ID NO: 1 to SEQ ID NO: 156.

The mitochondria activity adjusting composition according to the one embodiment of the present invention, wherein the composition for the treatment of a mitochondrial related diseases or disorder, prevention, inhibitory of progress, or relief of symptoms as an a pharmaceutical composition, wherein the active ingredient will be treated for a mitochondrial related diseases or disorder, prevention, inhibitory of progress, or relief of symptoms.

The "Mitochondrial related diseases" disclosed herein comprise Huntington's disease, amyotrophic lateral sclerosis, MELAS (Mitochondrial Encephalomyopathy with Lactic Acidemia and Stroke-like episodes); MERRF (Myoclonus, epilepsy, and myopathy with ragged red fibers; NARP/MILS (Neurogenic muscular weakness, ataxia, retinitis pigmentosa/Maternally inherited leigh syndrome); LHON (Lebers hereditary optic neuropathy); KSS (Kearns-Sayre Syndrome); PMPS (Pearson Marrow-Pancreas Syndrome); CPEO (Chronic progressive external opthalnoplegia); Reye's syndrome; Alper's syndrome; Multiple mtDNA deletion syndrome; mtDNA depletion syndrome; Complex I deficiency; Complex II (SDH) deficiency; Complex III deficiency; Cytochrome c oxidase (COX, Complex IV) deficiency; Complex V deficiency; Adenine nucleotide translocator (ANT) deficiency; Pyruvate dehydrogenase (PDH) deficiency; Ethyl malonic acid aciduria having lactic acid acidemia; 3-methyl glutaconic acid aciduria having lactic acid acidemia; refractoriness epilepsy representing a decline during infection; Asperger's syndrome representing a decline during infection; Autism representing a decline during infection; Attention deficit hyperactivity disorder (ADHD); Cerebral palsy representing a decline during infection; Alexia representing a decline during infection; Maternal hereditary thrombocytopenia; Leukemia; MNGIE (Mitochondrial myopathy, peripheral and autonomic neuropathy, gastrointestinal dysfunction, and epilepsy); MARIAHS syndrome (Mitochondrial ataxia, recrudescent infection, aphasia, hypouricemia/hypomyelination, seizure and dicarboxylic acid aciduria); ND6 dystonia; Cyclic vomiting syndrome representing a decline during infection; 3-hydroxyisobutyric acid aciduria having lactic acid acidemia; Diabetes having lactic acid acidemia; Uridine reactive neural syndrome (URNS); Familial bilateral striatum necrosis (FBSN); Hearing loss related with aminoglycoside; Relaxed myocardiopathy; Spleen lymphoma; Wolframs syndrome; Multiple mitochondria DNA deletions syndrome; and Renal tubular acidosis/diabetes/ataxia syndrome, but not limited to those.

In another embodiment of the present invention, nucleic acid molecules encoding above-mentioned polypeptides are provided. The nucleic acid molecules, for example, have base sequences of GAA GCG CGC CCG GCG CTG CTG ACC AGC CGC CTG CGC TTT ATT CCG AAA (SEQUENCE NO: 181). The nucleic acids can be introduced into the host cell according to a known method to those skilled in the art. For example, the known methods may be transformation method by calcium phosphate method, liposome, electroporation, contacting a virus and a cell, or micro injection directly into the cell, etc. The host cell is higher eukaryotic cell, for example, mammalian cells, or lower eukaryotic cells, such as a yeast cell, or prokaryotic cells, such as a bacterial cell. The prokaryotic host cells appropriate for transformation may be the species which belong to *E. coli, Bacillus subtillis, Salmonella typhimurium, Pseudomonas, Streptomyces*, and Micro bacteria species, as examples.

The vector including above-mentioned nucleic acid molecules is generally recombinant expression vector and it comprises, origin of replication enabling a host cell transformation, and a selectable marker (for example, dihydrofolate reductase for eukaryotic cell culture, or tolerance of neomycin, tolerance of tetra-cycline or ampicillin in *E. coli*, or *S. cerevisiae* TRP1 gene), and the promoter for controlling transcription of protein coating sequences. Available expression vectors are, for example, known bacterial plasmids such as SV40, derivatives of pcDNA, and known bacterial plasmids such as colE1, pCR1, pBR322, pMal-C2, pET, pGEX (Smith, et al., Gene 67:31-40 (1988)), plasmids such as pMB9 and its derivative RP4, phage DNA which is the same as numerous derivatives of phage I such as NM989, phage DNA such as M13 and single-stranded phage DNA of filament type; yeast plasmid, for example, phage DNA or vector induced from a combination of modified plasmid for using expression suppression sequences and phage DNA. The mammalian expression vectors comprise origin of replication, an appropriate promoter and an enhancer. Also, they can comprise compulsory ribosome binding sites, polyadenylation sites, splice donor, and receptor part, transcription termination sequences, and 5' planking non-transcriptional sequences. The mammalian expression vectors can comprise an inducible promoter, for example, a vector containing dihydrofolate reductase promoter, any expression vectors containing DHFR expression cassette or DHFR/methotrexate co-amplification vector such as pED. (Randal J, kaufman, 1991, Randal J. Kaufman, Current Protocols in Molycular Biology, 16, 12 (1991)). Or, glutamine synthetase/methionine sulfoximine co-amplification vector, for example, pEE14 (Celltech), Epstein-Barr-Virus (EBV), or a vector directing episomal expression under the control of nuclear antigen (EBNA), for example, pREP4 (Invitrogen), pCEP4 (Invitrogen), pMEP4 (Invitrogen), pREP8 (Invitrogen), pREP9 (Invitrogen) and pEBVHis (Invitrogen) can be used. Selectable mammalian expression vectors are Rc/CMV (Invitrogen) and pRc/RSV (Invitrogen) etc. Vaccinia virus mammalian expression vectors which can be used in the present invention are pSC11, pMJ601, pTKgptF1S, etc.

Yeast expression vector system to be used in the present invention is non-fusion pYES2 vector (Invitrogen), fusion pYESHisA, B, C (Invitrogen), pRS vector, etc.

The above-mentioned vectors can be introduced to various cells, such as mammalian cells which is especially the human derived cells, or bacteria, yeast, fungi, insects, nematodes, and plant cells. The examples of appropriate cells are VERO cell, HELA cell for example, ATCC No. CCL2, CHO cell line, for example, ATCC No. CCL61, COS cell, for example COS-7 cell and ATCC No. CRL 1650 cell, W138, BHK, HepG2, 3T3, for example, ATCC No. CRL6361, A549, PC12, K562 cell, 293 cell, Sf9 cell, for example, ATCC No. CRL1711 and Cv1 cell, such as ATCC No. CCL70, etc.

Other appropriate cells to be used in the present invention are prokaryotic host cell strain, for example, the strains belonging to *E. coli* (e.g. DH5-α strain), *Bacillus subtilis, Salmonella typhimurium, Pseudomonas, Streptomyces* and *Staphylococcus*.

In one embodiment of the present invention, the composition may contain 0.1 µg/mg to 1 mg/mg, specifically 1 µg/mg to 0.5 mg/mg, more specifically 10 µg/mg to 0.1 mg/mg of a peptide comprising any one amino acid sequence of SEQ ID NO: 1 to SEQ ID NO: 156, a peptide comprising amino acid sequence above 80% homology with above-mentioned sequence, or a fragment of above-mentioned peptide. When the peptide is contained in the above-mentioned range, all the safety and stability of the composition can be satisfied and appropriate in terms of cost-effectiveness.

In one embodiment of the present invention, the composition may have application with all animals including human, dog, chicken, pig, cow, sheep, guinea pig, and monkey.

In one embodiment of the present invention, the pharmaceutical composition may be administered through oral, rectal, transdermal, intravenous, intramuscular, intraperitoneal, in the bone marrow, epidural or subcutaneous means.

Forms of oral administration may be, but not limited to, tablets, pills, soft or hard capsules, granules, powders, solution, or emulsion. Forms of non-oral administration can be, but not limited to, injections, drips, lotions, ointments, gels, creams, suspensions, emulsions, suppository, patch, or spray.

In one embodiment of the present invention, the pharmaceutical composition, if necessary, may contain additives, such as diluents, excipients, lubricants, binders, disintegrants, buffers, dispersants, surfactants, coloring agents, aromatics or sweeteners. In one embodiment of the present invention, the pharmaceutical composition may be manufactured by conventional methods of the industry in the art.

In one embodiment of the present invention, the active ingredient of the medical composition may vary according to the patient's age, sex, weight, pathology and state, administration route, or prescriber's judgment. Dosage based on these factors is determined within levels of those skilled in the art, and the daily dose for example may be, but not limited to, 0.1 µg/kg/day to 1 g/kg/day, specifically 1 µg/kg/day to 10 mg/kg/day, more specifically the 10 µg/kg/day to 1 mg/kg/day, more specifically the 50 µg/kg/day to 100 µg/kg/day. In one embodiment of the present invention, the pharmaceutical composition may be administered, but not limited to, 1 to 3 times a day.

In one embodiment of the present invention, cosmetic composition may be provided in all forms appropriate for topical applications. For example, forms may be provided as solutions, emulsions obtained by dispersion of oil phase in water, emulsion obtained by dispersion of water in oil phase, suspension, solid, gel, powder, paste, foam or aerosol. These forms may be manufactured by conventional methods of the industry in the art.

In one embodiment of the present invention, the cosmetic composition may include, within levels that won't harm the main effect, other ingredients that may desirably increase the main effect. In one embodiment of the present invention, the cosmetic composition may additionally include moisturizer, emollient agents, surfactants, UV absorbers, preservatives, fungicides, antioxidants, pH adjusting agent, organic or inorganic pigments, aromatics, cooling agent or antiperspirant. The formulation ratio of the above-mentioned ingredients may be decided by those skilled in the art within levels that won't harm the purpose and the effects of the present invention, and the formulation ratio based on total weight of the cosmetic composition may be 0.01 to 5% by weight, specifically 0.01 to 3% by weight.

In one embodiment of the present invention, food composition is not limited to forms, but for example may be granules, powder, liquid, and solid forms. Each form may be formed with ingredients commonly used in the industry appropriately chosen by those skilled in the art, in addition to the active ingredient, and may increase the effect with other ingredients.

Decision for dosage on the above-mentioned active ingredient is within the level of those skilled in the art, and daily dosage for example may be 1 µg/kg/day to 10 mg/kg/day, more specifically the 10 µg/kg/day to 1 mg/kg/day, more specifically the 50 µg/kg/day to 100 µg/kg/day, but not limited to these numbers and can vary according to age, health status, complications and other various factors.

The terms used herein is intended to be used to describe the embodiments, not to limit the present invention. Terms without numbers in front are not to limit the quantity but to show that there may be more than one thing of the term used. The term "including", "having", "consisting", and "comprising" shall be interpreted openly (i.e. "including but not limited to").

Mention of range of numbers is used instead of stating separate numbers within the range, so unless it is explicitly stated, each number can be read as separate numbers integrated herein. The end values of all ranges are included in the range and can be combined independently.

Unless otherwise noted or clearly contradicting in context, all methods mentioned herein can be performed in the proper order. The use of any one embodiment and all embodiment, or exemplary language (e.g., that use "like ~"), unless included in the claims, is used to more clearly describe the present invention, not to limit the scope of the present invention. Any language herein outside of the claims should not be interpreted as a necessity of the present invention. Unless defined otherwise, technical and scientific terms used herein have meaning normally understood by a person skilled in the art that the present invention belongs to.

The preferred embodiments of the present invention are the best mode known to the inventors to perform the present invention. It can become clear to those skilled in the art after reading the statements ahead of the variations in the preferred embodiments. The present inventors hope that those skilled in the art can use the variations adequately and present invention be conducted in other ways than listed herein. Thus, the present invention, as allowed by the patent law, includes equivalents, and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

Example 1: Synthesis of Peptide

The peptides of SEQ ID NO: 1 to SEQ ID NO: 156 were synthesized according to the existing method of solid phase peptide synthesis. In detail, the peptides were synthesized by coupling each amino acid from C-terminus through Fmoc solid phase peptide synthesis, SPPS, using ASP48S (Peptron, Inc., Daejeon ROK). Those peptides with their first amino acid at the C-terminus being attached to resin were used as follows:

$NH_2$-Lys(Boc)-2-chloro-Trityl Resin $NH_2$-Ala-2-chloro-Trityl Resin $NH_2$-Arg(Pbf)-2-chloro-Trityl Resin All the amino acid materials to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in acid. Such as:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

HBTU [2-(1H-Benzotriazole-1-yl)-1,1,3,3-tetamethylaminium hexafluorophosphate]/HOBt [N-Hydroxybenzotriazole]/NMM [4-Methylmorpholine] were used as the coupling reagents. In 20% of DMF, piperidine was used to remove Fmoc. In order to remove the protection from residue or to separate the synthesized peptide from Resin, cleavage cocktail [TFA (trifluoroacetic acid)/TIS (triisopropylsilane)/EDT (ethanedithiol)/$H_2O$=92.5/2.5/2.5/2.51] was used.

Peptides were synthesized by using the solid phase scaffold by adding each amino acid with the sequential proesses as follow; amino acid protection, coupling reaction, washing, and deprotection. After cutting off the synthesized peptide from the resin, it was purified by HPLC and verify for synthesis by MS, and then freeze-dried.

Specific peptide synthesis process is described by the following with example of Pep1 of

SEQ ID NO: 164
(EARPALLTSRLRFIPK).

1) Coupling

The amino acid (8 equivalent) protected with $NH_2$-Lys (Boc)-2-chloro-Trityl Resin was melted in coupling agent HBTU (8 equiv.)/HOBt (8 equiv.)/NMM (16 equiv.), and upon addition of DMF, the reaction mixture was incubated at room temperature for 2 hours, then washed sequentially with DMF, MeOH, and DMF.

2) Fmoc deprotection

Following the addition of 20% piperidine in DMF, the reaction mixture was incubated at room temperature for 5 minutes 2 times, then washed sequentially with DMF, MeOH, and DMF.

3) Make the basic framework of peptide by repeating reactions 1 and 2 repeatedly.

4) Cleavage: Add Cleavage Cocktail to the completely synthesized peptide and separate the peptide from the resin.

5) Add pre-chilled diethyl ether into the mixture, and then centrifuge the reaction mixture to precipitate out the peptides.

6) After purification by Prep-HPLC, check the molecular weight by LC/MS and lyophilize to obtain the peptides in a powder form.

Example 2: Preparation of pep(CPP)-FITC Conjugate (1) Preparation of FITC-CPP Conjugate A conjugate of the peptides with SEQ ID NO: 1 to SEQ ID NO: 156 combined with FITC was manufactured as follows, for example, a conjugate of pep1 (SEQ ID NO: 157) and FITC, in other words, FITC-linker-pep1 was manufactured as follows.

The basic framework of peptide, $NH_2$-linker-E(OtBu)-A-R(Pbf)-P-A-L-L-T(tBu)-S(tBu)-R(Pbf)L-R(Pbf)-F-I-P-K (Boc)-2-chloro-Trityl Resin) which was obtained according to the manufacturing methods described in Example 1, was reacted with FITC. Specifically, FITC (fluorescein-5isothiocyanate) (8 equivalent) and DIPEA (N,N-Diisopropylethtylamine) (16 equivalent) were melted in DMF. The DMF solution was added, and reacted at room temperature for 2 hours, then washed sequentially with DMF, MeOH and DMF. As a result, FITC-linker-E(OtBu)-A-R(Pbf)-P-A-L-L-T(tBu)-S(tBu)-R(Pbf)L-R(Pbf)-F-I-P-K(Boc)-2-chloro-Trityl Resin was obtained. The linker herein is 6-aminohexanoic acid, Ahx. TFA/TIS/$H_2O$=95/2.5/2.5 was added to the peptide made on the resin, and the conjugate was separated from the resin. A pre-chilled diethyl ether was added to the obtained mixture, and centrifugation was used to precipitate the peptide conjugates. After purification by Prep-HPLC, purity was confirmed with the analytical HPLC and the molecular weight was determined by LC/MS. The peptide synthesized as described above was verified as FITC-pep1 by confirmation of the molecular weight by LC/MS. Then the conjugates were lyophilized. SEQ ID NO: 1 to SEQ ID NO: 156 of peptides fused FITC with conjugate was also prepared as pep1 of SEQ ID NO: 157.

(2) Preparation of a CPP-FITC Conjugate

The basic framework of the peptide, ($NH_2$-E(OtBu)-A-R(Pbf)-P-A-L-L-T(tBu)-S(tBu)-R(Pbf)L-R(Pbf)-F-I-P-K(Dde)-2-chloro-Trityl Resin) was generated according to the manufacturing methods described in the Example 2 1. (1). To selectively introduce FITC to the C-term of the peptide, the N-term of the peptide was protected from Boc. Then, the Di-tert-butyl Bicarbonate (30 equivalent) and DIPEA (30 equivalent) were melted in DMF. The DMF solution was added to the peptide and incubated at room temperature for 2 hours, and the peptide was washed sequentially with DMF, MeOH, and DMF. As a result, Boc-E(OtBu)-A-R(Pbf)-P-A-L-L-T(tBu)-S(tBu)-R(Pbf)L-R(Pbf)-F-I-P-K(Dde)-2-chloro-Trityl Resin was obtained. Hydrazine in 2% of DMF was used to remove Dde which is the protecting group of the C-terminal residue Lys in order to add FITC to the C-terminal of Lys. Then, FITC (8 equivalent) and DIPEA (16 equivalent) were melted in DMF which was added to the peptide reaction mixture, and the mixture was incubated at room temperature for 2 hours, then washed sequentially with DMF, MeOH, DMF. As a result, Boc-E(OtBu)-A-R(Pbf)-P-A-L-L-T(tBu)-S(tBu)-R(PbF)L-R(Pbf)-F-I-P-K(FITC)-2-chloro-Trityl Resin was obtained. TFA/TIS/$H_2O$=95/2.5/2.5 was added to separate the peptide from resin. Pre-chilled diethyl ether was added to the the mixture, and centrifugation was used to precipitate the peptides. After purification by Prep-HPLC, purity was confirmed with the analytical HPLC and the molecular weight was confirmed with LC/MS. The obtained substances were verified as pep1-FITC by confirmation of the molecular weight by LC/MS. Then the conjugates were lyophilized. SEQ ID NO: 1 to SEQ ID NO: 156 of peptide-FITC conjugates were also prepared in the same manner as described above pep1-FITC.

Example 3: Experimental Cell Penetration of pep(CPP)-FITC Conjugate (1) Experimental Cell Penetration in HeLa Cell Line Cell Culture Homo sapiens cervix adenocarcinoma cell line as HeLa cell lines were purchased from ATCC (American Type Cell Culture). The cells were cultured in MEM supplemented with 10% fetal bovine serum (Invitrogen, USA), Earle's salts, non-essential amino acids, sodium pyruvate and 100 μg/ml penicillin and 10 units/ml streptomycin and cultured at 37° C., 5% $CO_2$ incubator.

Flow Cytometry and Confocal Microscopy Analysis of Cell Penetrating

Flow cytometry and Confocal microscope analysis were performed to compare the between degree of cellular uptake of the cells were treated with SEQ ID NO: 1 to SEQ ID NO: 156, pep (CPP) and control.

The cell line was divided in a 6-well plate and cultured in a medium containing 10% fetal bovine serum (Invitrogen, USA), 100 μg/ml penicillin, 100 units/ml streptomycin at 37° C., 5% $CO_2$ incubator for 12 hours. After washing the cell line with PBS, starvation was induced in a Minimum Essential Medium for an hour. 20 μM of each carrier peptide was treated and cultured at 37° C. for an hour. After repeating the step of washing the cells with PBS for three times, Trypsin-EDTA was treated form 10 mins at 37° C. to separate the carrier peptide on the outside of the cell. cells were collected with refrigerated PBS and centrifugation was performed to repeat the step of washing the cells for three times. After then, the cells were suspended in 0.5 ml of PBS containing 4% Paraformaldehyde and fluorescence of the cells was analyzed using FACS Calibur (Becton Dickinson). The cellular uptake aspect of control and various peptides combined with FITC was compared and analyzed by MFI (Mean Fluorescence Intensity).

The results are as shown in FIGS. 1 to 23. Analysis results shown in FIG. 1 to FIG. 23 are given in detail in Table 3 below.

TABLE 3

| | pep2 | pep3 | pep4 | pep5 | pep6 | pep7 | pep8 |
|---|---|---|---|---|---|---|---|
| control | 3.98 ± 0.87 | 2.39 ± 0.23 | 3.98 ± 0.87 | 3.98 ± 0.87 | 3.98 ± 0.87 | 3.98 ± 0.87 | 3.98 ± 0.87 |
| peptide | 37.6 ± 1.89 | 18.23 ± 3.21 | 28.35 ± 2.54 | 19.06 ± 1.33 | 15.81 ± 1.59 | 9.51 ± 2.95 | 17.75 ± 1.96 |
| | pep10 | pep11 | pep12 | pep13 | pep14 | pep15 | pep16 |
| control | 3.98 ± 0.87 | 2.39 ± 0.23 | 3.98 ± 0.87 | 3.98 ± 0.87 | 2.39 ± 0.23 | 3.98 ± 0.87 | 3.98 ± 0.87 |
| peptide | 559.78 ± 3.41 | 10.46 ± 1.99 | 22 ± 2.6 | 14.01 ± 1.32 | 10.51 ± 3.71 | 35.61 ± 1.29 | 20.12 ± 1.84 |
| | pep17 | pep18 | pep19 | pep20 | pep21 | pep22 | pep23 |
| control | 3.98 ± 0.87 | 3.98 ± 0.87 | 2.39 ± 0.23 | 3.98 ± 0.87 | 2.39 ± 0.23 | 3.98 ± 0.87 | 3.98 ± 0.87 |
| peptide | 15.26 ± 2.23 | 18.7 ± 1.21 | 13.04 ± 3.41 | 20.73 ± 2.45 | 13.22 ± 1.67 | 13.56 ± 0.23 | 15.68 ± 2.03 |
| | pep24 | pep25 | pep26 | pep27 | pep28 | pep29 | pep30 |
| control | 3.98 ± 0.87 | 3.98 ± 0.87 | 3.98 ± 0.87 | 3.98 ± 0.87 | 3.98 ± 0.87 | 3.98 ± 0.87 | 3.98 ± 0.87 |
| peptide | 13.78 ± 1.07 | 18.62 ± 0.69 | 14.81 ± 1.77 | 9.89 ± 2.51 | 14.08 ± 3.11 | 33.5 ± 2.48 | 14.37 ± 1.73 |
| | pep31 | pep32 | pep33 | pep34 | pep35 | pep36 | pep37 |
| control | 3.98 ± 0.87 | 3.98 ± 0.87 | 3.98 ± 0.87 | 3.98 ± 0.87 | 3.98 ± 0.87 | 3.98 ± 0.87 | 3.98 ± 0.87 |
| peptide | 14.93 ± 2.05 | 11.98 ± 2.92 | 14.36 ± 1.63 | 14.41 ± 3.44 | 15.54 ± 1.38 | 15.37 ± 2.65 | 20.81 ± 1.02 |
| | pep38 | pep39 | pep40 | pep41 | pep42 | pep43 | pep45 |
| control | 3.31 ± 0.62 | 3.98 ± 0.87 | 3.98 ± 0.87 | 3.98 ± 0.87 | 3.98 ± 0.87 | 3.98 ± 0.87 | 3.31 ± 0.62 |
| peptide | 380.4 ± 2.6 | 21.4 ± 0.99 | 11.63 ± 1.11 | 28.97 ± 3.44 | 20.82 ± 1.93 | 29.88 ± 2.35 | 203.77 ± 3.26 |

TABLE 3-continued

|  | pep46 | pep47 | pep48 | pep49 | pep50 | pep51 | pep52 |
|---|---|---|---|---|---|---|---|
| control | 3.98 ± 0.87 | 3.98 ± 0.87 | 3.98 ± 0.87 | 3.98 ± 0.87 | 2.39 ± 0.23 | 3.98 ± 0.87 | 3.98 ± 0.87 |
| peptide | 24.67 ± 2.02 | 15.85 ± 1.03 | 26.51 ± 2.36 | 13.91 ± 0.51 | 2228.76 ± 3.68 | 59.81 ± 1.38 | 16.67 ± 2.22 |

|  | pep53 | pep54 | pep56 | pep57 | pep58 | pep59 | pep60 |
|---|---|---|---|---|---|---|---|
| control | 3.98 ± 0.87 | 2.52 ± 0.41 | 3.98 ± 0.87 | 2.39 ± 0.23 | 3.98 ± 0.87 | 3.98 ± 0.87 | 3.98 ± 0.87 |
| peptide | 16.16 ± 0.66 | 388.45 ± 2.94 | 28.61 ± 0.44 | 568.02 ± 3.01 | 19.87 ± 0.94 | 18.58 ± 0.52 | 15.79 ± 1.63 |

|  | pep62 | pep63 | pep65 | pep66 | pep68 | pep70 | pep71 |
|---|---|---|---|---|---|---|---|
| control | 3.98 ± 0.87 | 3.98 ± 0.87 | 3.98 ± 0.87 | 2.52 ± 0.41 | 3.98 ± 0.87 | 3.98 ± 0.87 | 3.98 ± 0.87 |
| peptide | 14.55 ± 3.71 | 21.3 ± 1.55 | 12.72 ± 1.36 | 20.7 ± 2.57 | 27.28 ± 1.28 | 21.82 ± 1.76 | 16.61 ± 0.88 |

|  | pep72 | pep76 | pep79 | pep80 | pep81 | pep82 | pep83 |
|---|---|---|---|---|---|---|---|
| control | 3.98 ± 0.87 | 2.52 ± 0.41 | 3.98 ± 0.87 | 3.98 ± 0.87 | 2.39 ± 0.23 | 3.98 ± 0.87 | 3.98 ± 0.87 |
| peptide | 17.57 ± 2.31 | 13.98 ± 0.11 | 31.2 ± 1.52 | 12.45 ± 0.46 | 29.69 ± 2.49 | 22.44 ± 3.32 | 24.57 ± 1.36 |

|  | pep87 | pep88 | pep89 | pep91 | pep92 | pep94 | pep95 |
|---|---|---|---|---|---|---|---|
| control | 2.52 ± 0.41 | 3.98 ± 0.87 | 3.98 ± 0.87 | 3.93 ± 0.87 | 3.98 ± 0.87 | 2.39 ± 0.23 | 3.98 ± 0.87 |
| peptide | 38.35 ± 2.27 | 16.43 ± 0.55 | 13.54 ± 0.75 | 24.41 ± 2.79 | 19.91 ± 0.51 | 117.76 ± 4.24 | 10.92 ± 0.07 |

|  | pep96 | pep102 | pep103 | pep104 | pep105 | prep106 | pep107 |
|---|---|---|---|---|---|---|---|
| control | 2.39 ± 0.23 | 2.52 ± 0.41 | 3.98 ± 0.87 | 2.39 ± 0.23 | 3.98 ± 0.87 | 3.98 ± 0.87 | 3.98 ± 0.87 |
| peptide | 308.53 ± 3.61 | 45.84 ± 1.58 | 126.88 ± 2.14 | 36.74 ± 1.11 | 13.23 ± 2.21 | 12.45 ± 0.38 | 23.11 ± 0.56 |

|  | pep108 | pep109 | pep110 | pep113 | pep116 | pep117 | pep118 |
|---|---|---|---|---|---|---|---|
| control | 3.98 ± 0.87 | 3.98 ± 0.87 | 3.98 ± 0.87 | 3.98 ± 0.87 | 3.98 ± 0.87 | 3.98 ± 0.87 | 2.53 ± 0.17 |
| peptide | 22.53 ± 0.95 | 12.46 ± 1.32 | 22.04 ± 0.77 | 16.09 ± 2.5 | 20.5 ± 0.97 | 23.11 ± 2.46 | 14.69 ± 0.33 |

|  | pep119 | pep123 | pep124 | pep125 | pep126 | pep128 | pep131 |
|---|---|---|---|---|---|---|---|
| control | 2.53 ± 0.17 | 3.98 ± 0.87 | 2.53 ± 0.17 | 2.53 ± 0.17 | 2.53 ± 0.17 | 3.98 ± 0.87 | 2.39 ± 0.23 |
| peptide | 13.23 ± 0.64 | 18.03 ± 2.83 | 23.74 ± 3.62 | 28.62 ± 2.12 | 3362.29 ± 3.24 | 14.36 ± 1.21 | 32.51 ± 2.38 |

|  | pep132 | pep133 | pep134 | pep138 | pep139 | pep141 | pep145 |
|---|---|---|---|---|---|---|---|
| control | 3.98 ± 0.87 | 2.53 ± 0.17 | 2.39 ± 0.23 | 3.98 ± 0.87 | 2.39 ± 0.23 | 3.98 ± 0.87 | 3.98 ± 0.87 |
| peptide | 26.39 ± 0.95 | 46.79 ± 1.92 | 78.05 ± 2.26 | 16.43 ± 0.91 | 29.95 ± 0.28 | 20.89 ± 0.31 | 11.97 ± 0.78 |

|  | pep146 | pep150 | pep151 | pep153 | pep158 | pep160 |
|---|---|---|---|---|---|---|
| control | 2.53 ± 0.17 | 3.98 ± 0.87 | 3.98 ± 0.87 | 2.53 ± 0.17 | 3.98 ± 0.87 | 2.53 ± 0.17 |
| peptide | 18.32 ± 1.82 | 17.46 ± 0.24 | 23.52 ± 0.56 | 31.72 ± 1.74 | 87.75 ± 2.51 | 9.860.23 |

(2) Cell Penetrating Property in Huh7 Cell Line

Cell Culture human hepatocellular carcinoma cell line as Huh7 lines were purchased from ATCC (American Type Cell Culture) and used as suspended cells. The cells were cultured in MEM supplemented with 10% fetal bovine serum (Invitrogen, USA), EarleSA), Earle Huh7 lines were purchased from ATpyruvate and 100 μa/ml penicillin and 10 units/ml streptomycin and cultured at 37° C., 5% $CO_2$ incubator.

The Screening Analysis of Cell Penetrating Used by Flow Cytometry

To confirm the cell penetrating of peptides, the Huh7 cell lines were treated with SEQ ID NO: 1 to SEQ ID NO: 156 and analysed by Flow cytometry. The analysed method was also confirmed by the same manner as described above example (1) in Hela cell lines. Also, the result showed in FIG. 24 to FIG. 43.

(3) Experimental Cell Penetration in Human T Lymphocyte Cell Lines

Cell Culture human T-cell leukemia cell line as Jurket was purchased from ATCC (American Type Cell Culture) and used as suspended cells. The cells were cultured in RPMI 1640 supplemented with 10% fetal bovine serum (Invitrogen, USA), EarleSA), EarleC (American Type Cell Culture) and pyruvate and 100 om ATCC (American Type units/ml streptomycin and cultured at 37° C. 5% $CO_2$ incubator. Human derived lymphocytes (lymphocyte) separated from the healthy human blood (50 m) and then collected layer of peripheral blood mononuclear cells (PBMC) and lymphocytes used by Biocoll separating solution (Biochrom AG, Berlin, Germany).

The Screening Analysis of Cell Penetrating Used by Flow Cytometry

To confirm the cell penetrating of peptides, the human T-cell leukemia cell lines were treated with SEQ ID NO: 1 to SEQ ID NO: 156 and analysed by Flow cytometry. The analysed method was also confirmed by the same manner as described above example (1) in Hela cell lines. Also, the result showed in FIG. 44 to FIG. 58.

(4) Analysis of Cell Viability and Toxicity

The cell line was divided into 96-well plate and cultured in a medium containing 10% fetal bovine serum (Invitrogen, USA), 100 µg/ml penicillin, 100 units/ml streptomycin at 37° C., 5% $CO_2$ incubator for 12 hours. After washing the cell line with PBS, starvation was induced in a Minimum Essential Medium for an hour. 20 µM of each carrier peptide was treated and cultured at 37° C. for an hour. After cultured cells, analysed cell viability and toxicity used by MTT assay. The results showed in FIG. 59 to FIG. 72.

What is claimed is:

1. A conjugate of a cell penetrating carrier peptide and a heterologous active ingredient, wherein the carrier peptide is 20 or less amino acids in length and comprises of is any one amino acid sequence of SEQ ID NO: 9, SEQ ID NO: 79, and SEQ ID NO: 135, or the carrier peptide is 20 or less amino acids in length and has at least 80% sequence identity with any one of the amino acid sequence of SEQ ID NO: 9, SEQ ID NO: 79, and SEQ ID NO: 135 and maintains cell penetrating ability, and wherein the carrier peptide and the active ingredient are combined via a) a covalent bond, and optionally mediated by a linker; or b) a non-covalent bond.

2. The conjugate according to claim 1, wherein the active ingredient is at least one selected from protein, nucleic acid, peptide, lipid, glycol-lipid, mineral, sugar, nano-particle, biological products, contrast agent, drugs and chemical compounds.

3. The conjugate according to claim 2, wherein the protein is a cytokine, antibody, fragment of antibody, therapeutic enzyme, soluble receptor or ligand.

4. The conjugate according to claim 2, wherein the contrast agent is selected from the group consisting of a radiopaque contrast agent, paramagnetic contrast agent, superparamagnetic contrast agent and CT contrast agent.

5. The conjugate according to claim 2, wherein the contrast agent is based on iron.

6. The conjugate according to claim 5, wherein the contrast agent is a ferrocene carboxylate.

7. A contrast agent comprising a conjugate of claim 1.

8. A contrast agent comprising a conjugate of claim 2.

9. A contrast agent comprising a conjugate of claim 3.

10. A contrast agent comprising a conjugate of claim 4.

11. A contrast agent comprising a conjugate of claim 5.

12. A contrast agent comprising a conjugate of claim 6.

13. A composition comprising the conjugate according to claim 1.

14. The composition according to claim 13, wherein the active ingredient is selected from the group consisting of an active agent for treatment or prevention of disease, an active ingredient of functional cosmetics, and an active ingredient of health functional food; and wherein the composition is selected from the group consisting of a pharmaceutical composition, a cosmetic composition, and a health food composition.

15. A cell penetrating carrier peptide, wherein the carrier peptide is 20 or less amino acids in length and is any one amino acid sequence of SEQ ID NO: 79 and SEQ ID NO: 135, or the carrier peptide is 20 or less amino acids in length and has at least 80% sequence identity with any one of the amino acid sequence of SEQ ID NO: 79 and SEQ ID NO: 135 and maintains cell penetrating ability.

16. A polynucleotide that encodes the peptide according to claim 15.

17. A vector that comprises the polynucleotide according to claim 16.

18. A transformed cell that comprises the vector according to claim 17.

19. A method of treating a subject having a mitochondrial-related disease or disorder comprising administering to the subject a pharmaceutical composition comprising the conjugate of claim 1.

20. The method of claim 19, wherein the pharmaceutical composition is administered though oral, rectal, transdermal, intravenous, intramuscular, intraperitoneal, in the bone marrow, epidural, or subcutaneous means.

21. The method of claim 19, wherein the pharmaceutical composition comprises additives selected from the group consisting of diluents, excipients, lubricants, binders, disintegrants, buffers, dispersants, surfactants, coloring agents, aromatics, and sweeteners.

* * * * *

```
                        SEQUENCE LISTING

<160> NUMBER OF SEQ ID NOS: 164

<210> SEQ ID NO 1
<211> LENGTH: 30
<212> TYPE: PRT
<213> ORGANISM: Homo sapiens

<400> SEQUENCE: 1

Ala Leu Phe Ser Val Leu Asn Tyr Glu Arg Ala Arg Pro Gly Leu
1               5                   10                  15

Leu Gly Ala Ser Val Leu Gly Leu Asp Asp Ile His Arg Ala
            20                  25                  30

<210> SEQ ID NO 2
<211> LENGTH: 15
<212> TYPE: PRT
<213> ORGANISM: Homo sapiens

<400> SEQUENCE: 2

Ser Val Leu Asn Tyr Glu Arg Ala Arg Pro Gly Leu Leu Gly
1               5                   10                  15

<210> SEQ ID NO 3
<211> LENGTH: 10
<212> TYPE: PRT
<213> ORGANISM: Homo sapiens

<400> SEQUENCE: 3

Gly Leu Leu Gly Ala Ser Val Leu Gly Leu
1               5                   10

<210> SEQ ID NO 4
<211> LENGTH: 10
<212> TYPE: PRT
<213> ORGANISM: Homo sapiens

<400> SEQUENCE: 4

Ala Leu Leu Thr Ser Arg Leu Arg Phe Ile
1               5                   10

<210> SEQ ID NO 5
<211> LENGTH: 9
<212> TYPE: PRT
<213> ORGANISM: Homo sapiens

<400> SEQUENCE: 5

Arg Pro Ala Leu Leu Thr Ser Arg Leu
1               5

<210> SEQ ID NO 6
<211> LENGTH: 9
<212> TYPE: PRT
<213> ORGANISM: Homo sapiens

<400> SEQUENCE: 6
```

Arg Leu Thr Ser Arg Val Lys Ala Leu
1               5

<210> SEQ ID NO 7
<211> LENGTH: 15
<212> TYPE: PRT
<213> ORGANISM: Homo sapiens

<400> SEQUENCE: 7

Arg Thr Phe Val Leu Arg Val Arg Ala Gln Asp Pro Pro Pro Glu
1               5                   10                  15

<210> SEQ ID NO 8
<211> LENGTH: 15
<212> TYPE: PRT
<213> ORGANISM: Homo sapiens

<400> SEQUENCE: 8

Arg Leu Thr Ser Arg Val Lys Ala Leu Phe Ser Val Leu Asn Tyr
1               5                   10                  15

<210> SEQ ID NO 9
<211> LENGTH: 15
<212> TYPE: PRT
<213> ORGANISM: Homo sapiens

<400> SEQUENCE: 9

Ala Glu Arg Leu Thr Ser Arg Val Lys Ala Leu Phe Ser Val Leu
1               5                   10                  15

<210> SEQ ID NO 10
<211> LENGTH: 9
<212> TYPE: PRT
<213> ORGANISM: Homo sapiens

<400> SEQUENCE: 10

Tyr Glu Arg Ala Arg Arg Pro Gly Leu
1               5

<210> SEQ ID NO 11
<211> LENGTH: 9
<212> TYPE: PRT
<213> ORGANISM: Homo sapiens

<400> SEQUENCE: 11

Leu Leu Gly Ala Ser Val Leu Gly Leu
1               5

<210> SEQ ID NO 12
<211> LENGTH: 10
<212> TYPE: PRT
<213> ORGANISM: Homo sapiens

<400> SEQUENCE: 12

Val Leu Gly Leu Asp Asp Ile His Arg Ala
1               5                   10

<210> SEQ ID NO 13
<211> LENGTH: 10
<212> TYPE: PRT
<213> ORGANISM: Homo sapiens

<400> SEQUENCE: 13

Gly Ala Ser Val Leu Gly Leu Asp Asp Ile
1               5                   10

```
<210> SEQ ID NO 14
<211> LENGTH: 10
<212> TYPE: PRT
<213> ORGANISM: Homo sapiens

<400> SEQUENCE: 14

Ala Leu Phe Ser Val Leu Asn Tyr Glu Arg
1               5                   10

<210> SEQ ID NO 15
<211> LENGTH: 10
<212> TYPE: PRT
<213> ORGANISM: Homo sapiens

<400> SEQUENCE: 15

Ser Val Leu Asn Tyr Glu Arg Ala Arg Arg
1               5                   10

<210> SEQ ID NO 16
<211> LENGTH: 10
<212> TYPE: PRT
<213> ORGANISM: Homo sapiens

<400> SEQUENCE: 16

Ser Val Leu Gly Leu Asp Asp Ile His Arg
1               5                   10

<210> SEQ ID NO 17
<211> LENGTH: 10
<212> TYPE: PRT
<213> ORGANISM: Homo sapiens

<400> SEQUENCE: 17

Phe Ser Val Leu Asn Tyr Glu Arg Ala Arg
1               5                   10

<210> SEQ ID NO 18
<211> LENGTH: 10
<212> TYPE: PRT
<213> ORGANISM: Homo sapiens

<400> SEQUENCE: 18

Asn Tyr Glu Arg Ala Arg Arg Pro Gly Leu
1               5                   10

<210> SEQ ID NO 19
<211> LENGTH: 10
<212> TYPE: PRT
<213> ORGANISM: Homo sapiens

<400> SEQUENCE: 19

Tyr Glu Arg Ala Arg Arg Pro Gly Leu Leu
1               5                   10

<210> SEQ ID NO 20
<211> LENGTH: 10
<212> TYPE: PRT
<213> ORGANISM: Homo sapiens

<400> SEQUENCE: 20

Arg Pro Gly Leu Leu Gly Ala Ser Val Leu
1               5                   10
```

```
<210> SEQ ID NO 21
<211> LENGTH: 9
<212> TYPE: PRT
<213> ORGANISM: Homo sapiens

<400> SEQUENCE: 21

Glu Arg Ala Arg Arg Pro Gly Leu Leu
1               5

<210> SEQ ID NO 22
<211> LENGTH: 9
<212> TYPE: PRT
<213> ORGANISM: Homo sapiens

<400> SEQUENCE: 22

Val Leu Gly Leu Asp Asp Ile His Arg
1               5

<210> SEQ ID NO 23
<211> LENGTH: 9
<212> TYPE: PRT
<213> ORGANISM: Homo sapiens

<400> SEQUENCE: 23

Ser Val Leu Asn Tyr Glu Arg Ala Arg
1               5

<210> SEQ ID NO 24
<211> LENGTH: 9
<212> TYPE: PRT
<213> ORGANISM: Homo sapiens

<400> SEQUENCE: 24

Val Leu Asn Tyr Glu Arg Ala Arg Arg
1               5

<210> SEQ ID NO 25
<211> LENGTH: 9
<212> TYPE: PRT
<213> ORGANISM: Homo sapiens

<400> SEQUENCE: 25

Ala Arg Arg Pro Gly Leu Leu Gly Ala
1               5

<210> SEQ ID NO 26
<211> LENGTH: 9
<212> TYPE: PRT
<213> ORGANISM: Homo sapiens

<400> SEQUENCE: 26

Pro Gly Leu Leu Gly Ala Ser Val Leu
1               5

<210> SEQ ID NO 27
<211> LENGTH: 9
<212> TYPE: PRT
<213> ORGANISM: Homo sapiens

<400> SEQUENCE: 27

Arg Arg Pro Gly Leu Leu Gly Ala Ser
1               5

<210> SEQ ID NO 28
<211> LENGTH: 9
```

```
<212> TYPE: PRT
<213> ORGANISM: Homo sapiens

<400> SEQUENCE: 28

Ala Leu Phe Ser Val Leu Asn Tyr Glu
1               5

<210> SEQ ID NO 29
<211> LENGTH: 9
<212> TYPE: PRT
<213> ORGANISM: Homo sapiens

<400> SEQUENCE: 29

Gly Leu Leu Gly Ala Ser Val Leu Gly
1               5

<210> SEQ ID NO 30
<211> LENGTH: 9
<212> TYPE: PRT
<213> ORGANISM: Homo sapiens

<400> SEQUENCE: 30

Ser Val Leu Gly Leu Asp Asp Ile His
1               5

<210> SEQ ID NO 31
<211> LENGTH: 8
<212> TYPE: PRT
<213> ORGANISM: Homo sapiens

<400> SEQUENCE: 31

Glu Arg Ala Arg Arg Pro Gly Leu
1               5

<210> SEQ ID NO 32
<211> LENGTH: 8
<212> TYPE: PRT
<213> ORGANISM: Homo sapiens

<400> SEQUENCE: 32

Ala Arg Arg Pro Gly Leu Leu Gly
1               5

<210> SEQ ID NO 33
<211> LENGTH: 8
<212> TYPE: PRT
<213> ORGANISM: Homo sapiens

<400> SEQUENCE: 33

Gly Leu Leu Gly Ala Ser Val Leu
1               5

<210> SEQ ID NO 34
<211> LENGTH: 8
<212> TYPE: PRT
<213> ORGANISM: Homo sapiens

<400> SEQUENCE: 34

Arg Ala Arg Arg Pro Gly Leu Leu
1               5

<210> SEQ ID NO 35
<211> LENGTH: 8
<212> TYPE: PRT
<213> ORGANISM: Homo sapiens
```

<400> SEQUENCE: 35

Leu Gly Ala Ser Val Leu Gly Leu
1               5

<210> SEQ ID NO 36
<211> LENGTH: 15
<212> TYPE: PRT
<213> ORGANISM: Homo sapiens

<400> SEQUENCE: 36

Val Thr Glu Thr Thr Phe Gln Lys Asn Arg Leu Phe Phe Tyr Arg
1               5                   10                  15

<210> SEQ ID NO 37
<211> LENGTH: 15
<212> TYPE: PRT
<213> ORGANISM: Homo sapiens

<400> SEQUENCE: 37

Leu Phe Phe Tyr Arg Lys Ser Val Trp Ser Lys Leu Gln Ser Ile
1               5                   10                  15

<210> SEQ ID NO 38
<211> LENGTH: 15
<212> TYPE: PRT
<213> ORGANISM: Homo sapiens

<400> SEQUENCE: 38

Lys Leu Gln Ser Ile Gly Ile Arg Gln His Leu Lys Arg Val Gln
1               5                   10                  15

<210> SEQ ID NO 39
<211> LENGTH: 15
<212> TYPE: PRT
<213> ORGANISM: Homo sapiens

<400> SEQUENCE: 39

Glu Ala Glu Val Arg Gln His Arg Glu Ala Arg Pro Ala Leu Leu
1               5                   10                  15

<210> SEQ ID NO 40
<211> LENGTH: 15
<212> TYPE: PRT
<213> ORGANISM: Homo sapiens

<400> SEQUENCE: 40

Arg Pro Ala Leu Leu Thr Ser Arg Leu Arg Phe Ile Pro Lys Pro
1               5                   10                  15

<210> SEQ ID NO 41
<211> LENGTH: 15
<212> TYPE: PRT
<213> ORGANISM: Homo sapiens

<400> SEQUENCE: 41

Phe Ile Pro Lys Pro Asp Gly Leu Arg Pro Ile Val Asn Met Asp
1               5                   10                  15

<210> SEQ ID NO 42
<211> LENGTH: 15
<212> TYPE: PRT
<213> ORGANISM: Homo sapiens

<400> SEQUENCE: 42

Arg Thr Phe Arg Arg Glu Lys Arg Ala Glu Arg Leu Thr Ser Arg
1               5                   10                  15

<210> SEQ ID NO 43
<211> LENGTH: 15
<212> TYPE: PRT
<213> ORGANISM: Homo sapiens

<400> SEQUENCE: 43

Leu Asp Asp Ile His Arg Ala Trp Arg Thr Phe Val Leu Arg Val
1               5                   10                  15

<210> SEQ ID NO 44
<211> LENGTH: 15
<212> TYPE: PRT
<213> ORGANISM: Homo sapiens

<400> SEQUENCE: 44

Phe Val Leu Arg Val Arg Ala Gln Asp Pro Pro Glu Leu Tyr
1               5                   10                  15

<210> SEQ ID NO 45
<211> LENGTH: 15
<212> TYPE: PRT
<213> ORGANISM: Homo sapiens

<400> SEQUENCE: 45

Pro Gln Asp Arg Leu Thr Glu Val Ile Ala Ser Ile Ile Lys Pro
1               5                   10                  15

<210> SEQ ID NO 46
<211> LENGTH: 15
<212> TYPE: PRT
<213> ORGANISM: Homo sapiens

<400> SEQUENCE: 46

Lys Ser Val Trp Ser Lys Leu Gln Ser Ile Gly Ile Arg Gln His
1               5                   10                  15

<210> SEQ ID NO 47
<211> LENGTH: 16
<212> TYPE: PRT
<213> ORGANISM: Homo sapiens

<400> SEQUENCE: 47

Leu Lys Arg Val Gln Leu Arg Glu Leu Ser Glu Ala Glu Val Arg Gln
1               5                   10                  15

<210> SEQ ID NO 48
<211> LENGTH: 20
<212> TYPE: PRT
<213> ORGANISM: Homo sapiens

<400> SEQUENCE: 48

Met Pro Arg Ala Pro Arg Cys Arg Ala Val Arg Ser Leu Leu Arg Ser
1               5                   10                  15

His Tyr Arg Glu
            20

<210> SEQ ID NO 49
<211> LENGTH: 20
<212> TYPE: PRT
<213> ORGANISM: Homo sapiens -continued

```
<400> SEQUENCE: 49

Val Leu Pro Leu Ala Thr Phe Val Arg Arg Leu Gly Pro Gln Gly Trp
1               5                   10                  15

Arg Leu Val Gln
            20

<210> SEQ ID NO 50
<211> LENGTH: 20
<212> TYPE: PRT
<213> ORGANISM: Homo sapiens

<400> SEQUENCE: 50

Arg Gly Asp Pro Ala Ala Phe Arg Ala Leu Val Ala Gln Cys Leu Val
1               5                   10                  15

Cys Val Pro Trp
            20

<210> SEQ ID NO 51
<211> LENGTH: 20
<212> TYPE: PRT
<213> ORGANISM: Homo sapiens

<400> SEQUENCE: 51

Asp Ala Arg Pro Pro Ala Ala Pro Ser Phe Arg Gln Val Ser Cys
1               5                   10                  15

Leu Lys Glu Leu
            20

<210> SEQ ID NO 52
<211> LENGTH: 20
<212> TYPE: PRT
<213> ORGANISM: Homo sapiens

<400> SEQUENCE: 52

Val Ala Arg Val Leu Gln Arg Leu Cys Glu Arg Gly Ala Lys Asn Val
1               5                   10                  15

Leu Ala Phe Gly
            20

<210> SEQ ID NO 53
<211> LENGTH: 20
<212> TYPE: PRT
<213> ORGANISM: Homo sapiens

<400> SEQUENCE: 53

Phe Ala Leu Leu Asp Gly Ala Arg Gly Gly Pro Pro Glu Ala Phe Thr
1               5                   10                  15

Thr Ser Val Arg
            20

<210> SEQ ID NO 54
<211> LENGTH: 20
<212> TYPE: PRT
<213> ORGANISM: Homo sapiens

<400> SEQUENCE: 54

Ser Tyr Leu Pro Asn Thr Val Thr Asp Ala Leu Arg Gly Ser Gly Ala
1               5                   10                  15

Trp Gly Leu Leu
            20
```

```
<210> SEQ ID NO 55
<211> LENGTH: 20
<212> TYPE: PRT
<213> ORGANISM: Homo sapiens

<400> SEQUENCE: 55

Leu Arg Arg Val Gly Asp Asp Val Leu Val His Leu Leu Ala Arg Cys
1               5                   10                  15

Ala Leu Phe Val
            20

<210> SEQ ID NO 56
<211> LENGTH: 20
<212> TYPE: PRT
<213> ORGANISM: Homo sapiens

<400> SEQUENCE: 56

Leu Val Ala Pro Ser Cys Ala Tyr Gln Val Cys Gly Pro Pro Leu Tyr
1               5                   10                  15

Gln Leu Gly Ala
            20

<210> SEQ ID NO 57
<211> LENGTH: 20
<212> TYPE: PRT
<213> ORGANISM: Homo sapiens

<400> SEQUENCE: 57

Ala Thr Gln Ala Arg Pro Pro His Ala Ser Gly Pro Arg Arg
1               5                   10                  15

Leu Gly Cys Glu
            20

<210> SEQ ID NO 58
<211> LENGTH: 20
<212> TYPE: PRT
<213> ORGANISM: Homo sapiens

<400> SEQUENCE: 58

Arg Ala Trp Asn His Ser Val Arg Glu Ala Gly Val Pro Leu Gly Leu
1               5                   10                  15

Pro Ala Pro Gly
            20

<210> SEQ ID NO 59
<211> LENGTH: 20
<212> TYPE: PRT
<213> ORGANISM: Homo sapiens

<400> SEQUENCE: 59

Ala Arg Arg Arg Gly Gly Ser Ala Ser Arg Ser Leu Pro Leu Pro Lys
1               5                   10                  15

Arg Pro Arg Arg
            20

<210> SEQ ID NO 60
<211> LENGTH: 20
<212> TYPE: PRT
<213> ORGANISM: Homo sapiens

<400> SEQUENCE: 60

Gly Ala Ala Pro Glu Pro Glu Arg Thr Pro Val Gly Gln Gly Ser Trp
1               5                   10                  15
```

Ala His Pro Gly
        20

<210> SEQ ID NO 61
<211> LENGTH: 20
<212> TYPE: PRT
<213> ORGANISM: Homo sapiens

<400> SEQUENCE: 61

Arg Thr Arg Gly Pro Ser Asp Arg Gly Phe Cys Val Val Ser Pro Ala
1               5                   10                  15

Arg Pro Ala Glu
        20

<210> SEQ ID NO 62
<211> LENGTH: 20
<212> TYPE: PRT
<213> ORGANISM: Homo sapiens

<400> SEQUENCE: 62

Glu Ala Thr Ser Leu Glu Gly Ala Leu Ser Gly Thr Arg His Ser His
1               5                   10                  15

Pro Ser Val Gly
        20

<210> SEQ ID NO 63
<211> LENGTH: 20
<212> TYPE: PRT
<213> ORGANISM: Homo sapiens

<400> SEQUENCE: 63

Arg Gln His His Ala Gly Pro Pro Ser Thr Ser Arg Pro Pro Arg Pro
1               5                   10                  15

Trp Asp Thr Pro
        20

<210> SEQ ID NO 64
<211> LENGTH: 20
<212> TYPE: PRT
<213> ORGANISM: Homo sapiens

<400> SEQUENCE: 64

Cys Pro Pro Val Tyr Ala Glu Thr Lys His Phe Leu Tyr Ser Ser Gly
1               5                   10                  15

Asp Lys Glu Gln
        20

<210> SEQ ID NO 65
<211> LENGTH: 20
<212> TYPE: PRT
<213> ORGANISM: Homo sapiens

<400> SEQUENCE: 65

Leu Arg Pro Ser Phe Leu Leu Ser Ser Leu Arg Pro Ser Leu Thr Gly
1               5                   10                  15

Ala Arg Arg Leu
        20

<210> SEQ ID NO 66
<211> LENGTH: 20
<212> TYPE: PRT
<213> ORGANISM: Homo sapiens

<400> SEQUENCE: 66

Val Glu Thr Ile Phe Leu Gly Ser Arg Pro Trp Met Pro Gly Thr Pro
1               5                   10                  15

Arg Arg Leu Pro
            20

<210> SEQ ID NO 67
<211> LENGTH: 20
<212> TYPE: PRT
<213> ORGANISM: Homo sapiens

<400> SEQUENCE: 67

Arg Leu Pro Gln Arg Tyr Trp Gln Met Arg Pro Leu Phe Leu Glu Leu
1               5                   10                  15

Leu Gly Asn His
            20

<210> SEQ ID NO 68
<211> LENGTH: 20
<212> TYPE: PRT
<213> ORGANISM: Homo sapiens

<400> SEQUENCE: 68

Ala Gln Cys Pro Tyr Gly Val Leu Leu Lys Thr His Cys Pro Leu Arg
1               5                   10                  15

Ala Ala Val Thr
            20

<210> SEQ ID NO 69
<211> LENGTH: 20
<212> TYPE: PRT
<213> ORGANISM: Homo sapiens

<400> SEQUENCE: 69

Pro Ala Ala Gly Val Cys Ala Arg Glu Lys Pro Gln Gly Ser Val Ala
1               5                   10                  15

Ala Pro Glu Glu
            20

<210> SEQ ID NO 70
<211> LENGTH: 20
<212> TYPE: PRT
<213> ORGANISM: Homo sapiens

<400> SEQUENCE: 70

Glu Asp Thr Asp Pro Arg Arg Leu Val Gln Leu Leu Arg Gln His Ser
1               5                   10                  15

Ser Pro Trp Gln
            20

<210> SEQ ID NO 71
<211> LENGTH: 20
<212> TYPE: PRT
<213> ORGANISM: Homo sapiens

<400> SEQUENCE: 71

Arg His Asn Glu Arg Arg Phe Leu Arg Asn Thr Lys Lys Phe Ile Ser
1               5                   10                  15

Leu Gly Lys His
            20

<210> SEQ ID NO 72
<211> LENGTH: 20
<212> TYPE: PRT
<213> ORGANISM: Homo sapiens

<400> SEQUENCE: 72

Ala Lys Leu Ser Leu Gln Glu Leu Thr Trp Lys Met Ser Val Arg Asp
1               5                   10                  15

Cys Ala Trp Leu
            20

<210> SEQ ID NO 73
<211> LENGTH: 20
<212> TYPE: PRT
<213> ORGANISM: Homo sapiens

<400> SEQUENCE: 73

Arg Arg Ser Pro Gly Val Gly Cys Val Pro Ala Ala Glu His Arg Leu
1               5                   10                  15

Arg Glu Glu Ile
            20

<210> SEQ ID NO 74
<211> LENGTH: 20
<212> TYPE: PRT
<213> ORGANISM: Homo sapiens

<400> SEQUENCE: 74

Leu Ala Lys Phe Leu His Trp Leu Met Ser Val Tyr Val Val Glu Leu
1               5                   10                  15

Leu Arg Ser Phe
            20

<210> SEQ ID NO 75
<211> LENGTH: 20
<212> TYPE: PRT
<213> ORGANISM: Homo sapiens

<400> SEQUENCE: 75

Phe Tyr Val Thr Glu Thr Thr Phe Gln Lys Asn Arg Leu Phe Phe Tyr
1               5                   10                  15

Arg Lys Ser Val
            20

<210> SEQ ID NO 76
<211> LENGTH: 20
<212> TYPE: PRT
<213> ORGANISM: Homo sapiens

<400> SEQUENCE: 76

Trp Ser Lys Leu Gln Ser Ile Gly Ile Arg Gln His Leu Lys Arg Val
1               5                   10                  15

Gln Leu Arg Glu
            20

<210> SEQ ID NO 77
<211> LENGTH: 20
<212> TYPE: PRT
<213> ORGANISM: Homo sapiens

<400> SEQUENCE: 77

Leu Ser Glu Ala Glu Val Arg Gln His Arg Glu Ala Arg Pro Ala Leu

```
1               5                  10                 15
Leu Thr Ser Arg
            20

<210> SEQ ID NO 78
<211> LENGTH: 20
<212> TYPE: PRT
<213> ORGANISM: Homo sapiens

<400> SEQUENCE: 78

Leu Arg Phe Ile Pro Lys Pro Asp Gly Leu Arg Pro Ile Val Asn Met
1               5                   10                  15

Asp Tyr Val Val
            20

<210> SEQ ID NO 79
<211> LENGTH: 20
<212> TYPE: PRT
<213> ORGANISM: Homo sapiens

<400> SEQUENCE: 79

Gly Ala Arg Thr Phe Arg Arg Glu Lys Arg Ala Glu Arg Leu Thr Ser
1               5                   10                  15

Arg Val Lys Ala
            20

<210> SEQ ID NO 80
<211> LENGTH: 20
<212> TYPE: PRT
<213> ORGANISM: Homo sapiens

<400> SEQUENCE: 80

Leu Phe Ser Val Leu Asn Tyr Glu Arg Ala Arg Arg Pro Gly Leu Leu
1               5                   10                  15

Gly Ala Ser Val
            20

<210> SEQ ID NO 81
<211> LENGTH: 20
<212> TYPE: PRT
<213> ORGANISM: Homo sapiens

<400> SEQUENCE: 81

Asp Pro Pro Pro Glu Leu Tyr Phe Val Lys Val Asp Val Thr Gly Ala
1               5                   10                  15

Tyr Asp Thr Ile
            20

<210> SEQ ID NO 82
<211> LENGTH: 20
<212> TYPE: PRT
<213> ORGANISM: Homo sapiens

<400> SEQUENCE: 82

Pro Gln Asp Arg Leu Thr Glu Val Ile Ala Ser Ile Ile Lys Pro Gln
1               5                   10                  15

Asn Thr Tyr Cys
            20

<210> SEQ ID NO 83
<211> LENGTH: 20
<212> TYPE: PRT
```

<213> ORGANISM: Homo sapiens

<400> SEQUENCE: 83

Val Arg Arg Tyr Ala Val Val Gln Lys Ala Ala His Gly His Val Arg
1               5                   10                  15

Lys Ala Phe Lys
            20

<210> SEQ ID NO 84
<211> LENGTH: 20
<212> TYPE: PRT
<213> ORGANISM: Homo sapiens

<400> SEQUENCE: 84

Ser His Val Ser Thr Leu Thr Asp Leu Gln Pro Tyr Met Arg Gln Phe
1               5                   10                  15

Val Ala His Leu
            20

<210> SEQ ID NO 85
<211> LENGTH: 20
<212> TYPE: PRT
<213> ORGANISM: Homo sapiens

<400> SEQUENCE: 85

Gln Glu Thr Ser Pro Leu Arg Asp Ala Val Val Ile Glu Gln Ser Ser
1               5                   10                  15

Ser Leu Asn Glu
            20

<210> SEQ ID NO 86
<211> LENGTH: 20
<212> TYPE: PRT
<213> ORGANISM: Homo sapiens

<400> SEQUENCE: 86

Ala Ser Ser Gly Leu Phe Asp Val Phe Leu Arg Phe Met Cys His His
1               5                   10                  15

Ala Val Arg Ile
            20

<210> SEQ ID NO 87
<211> LENGTH: 20
<212> TYPE: PRT
<213> ORGANISM: Homo sapiens

<400> SEQUENCE: 87

Arg Gly Lys Ser Tyr Val Gln Cys Gln Gly Ile Pro Gln Gly Ser Ile
1               5                   10                  15

Leu Ser Thr Leu
            20

<210> SEQ ID NO 88
<211> LENGTH: 20
<212> TYPE: PRT
<213> ORGANISM: Homo sapiens

<400> SEQUENCE: 88

Leu Cys Ser Leu Cys Tyr Gly Asp Met Glu Asn Lys Leu Phe Ala Gly
1               5                   10                  15

Ile Arg Arg Asp
            20

```
<210> SEQ ID NO 89
<211> LENGTH: 20
<212> TYPE: PRT
<213> ORGANISM: Homo sapiens

<400> SEQUENCE: 89

Gly Leu Leu Leu Arg Leu Val Asp Asp Phe Leu Leu Val Thr Pro His
1               5                   10                  15

Leu Thr His Ala
            20

<210> SEQ ID NO 90
<211> LENGTH: 20
<212> TYPE: PRT
<213> ORGANISM: Homo sapiens

<400> SEQUENCE: 90

Lys Thr Phe Leu Arg Thr Leu Val Arg Gly Val Pro Glu Tyr Gly Cys
1               5                   10                  15

Val Val Asn Leu
            20

<210> SEQ ID NO 91
<211> LENGTH: 20
<212> TYPE: PRT
<213> ORGANISM: Homo sapiens

<400> SEQUENCE: 91

Arg Lys Thr Val Val Asn Phe Pro Val Glu Asp Glu Ala Leu Gly Gly
1               5                   10                  15

Thr Ala Phe Val
            20

<210> SEQ ID NO 92
<211> LENGTH: 20
<212> TYPE: PRT
<213> ORGANISM: Homo sapiens

<400> SEQUENCE: 92

Gln Met Pro Ala His Gly Leu Phe Pro Trp Cys Gly Leu Leu Leu Asp
1               5                   10                  15

Thr Arg Thr Leu
            20

<210> SEQ ID NO 93
<211> LENGTH: 20
<212> TYPE: PRT
<213> ORGANISM: Homo sapiens

<400> SEQUENCE: 93

Glu Val Gln Ser Asp Tyr Ser Ser Tyr Ala Arg Thr Ser Ile Arg Ala
1               5                   10                  15

Ser Leu Thr Phe
            20

<210> SEQ ID NO 94
<211> LENGTH: 20
<212> TYPE: PRT
<213> ORGANISM: Homo sapiens

<400> SEQUENCE: 94
```

-continued

Lys Cys His Ser Leu Phe Leu Asp Leu Gln Val Asn Ser Leu Gln Thr
1               5                   10                  15

Val Cys Thr Asn
            20

<210> SEQ ID NO 95
<211> LENGTH: 20
<212> TYPE: PRT
<213> ORGANISM: Homo sapiens

<400> SEQUENCE: 95

Ile Tyr Lys Ile Leu Leu Leu Gln Ala Tyr Arg Phe His Ala Cys Val
1               5                   10                  15

Leu Gln Leu Pro
            20

<210> SEQ ID NO 96
<211> LENGTH: 20
<212> TYPE: PRT
<213> ORGANISM: Homo sapiens

<400> SEQUENCE: 96

Phe His Gln Gln Val Trp Lys Asn Pro Thr Phe Phe Leu Arg Val Ile
1               5                   10                  15

Ser Asp Thr Ala
            20

<210> SEQ ID NO 97
<211> LENGTH: 20
<212> TYPE: PRT
<213> ORGANISM: Homo sapiens

<400> SEQUENCE: 97

Ser Leu Cys Tyr Ser Ile Leu Lys Ala Lys Asn Ala Gly Met Ser Leu
1               5                   10                  15

Gly Ala Lys Gly
            20

<210> SEQ ID NO 98
<211> LENGTH: 20
<212> TYPE: PRT
<213> ORGANISM: Homo sapiens

<400> SEQUENCE: 98

Ala Ala Gly Pro Leu Pro Ser Glu Ala Val Gln Trp Leu Cys His Gln
1               5                   10                  15

Ala Phe Leu Leu
            20

<210> SEQ ID NO 99
<211> LENGTH: 20
<212> TYPE: PRT
<213> ORGANISM: Homo sapiens

<400> SEQUENCE: 99

Lys Leu Thr Arg His Arg Val Thr Tyr Val Pro Leu Leu Gly Ser Leu
1               5                   10                  15

Arg Thr Ala Gln
            20

<210> SEQ ID NO 100
<211> LENGTH: 20

```
<212> TYPE: PRT
<213> ORGANISM: Homo sapiens

<400> SEQUENCE: 100

Thr Gln Leu Ser Arg Lys Leu Pro Gly Thr Thr Leu Thr Ala Leu Glu
1               5                   10                  15

Ala Ala Ala Asn
            20

<210> SEQ ID NO 101
<211> LENGTH: 12
<212> TYPE: PRT
<213> ORGANISM: Homo sapiens

<400> SEQUENCE: 101

Pro Ala Leu Pro Ser Asp Phe Lys Thr Ile Leu Asp
1               5                   10

<210> SEQ ID NO 102
<211> LENGTH: 10
<212> TYPE: PRT
<213> ORGANISM: Homo sapiens

<400> SEQUENCE: 102

Met Pro Arg Ala Pro Arg Cys Arg Ala Val
1               5                   10

<210> SEQ ID NO 103
<211> LENGTH: 20
<212> TYPE: PRT
<213> ORGANISM: Homo sapiens

<400> SEQUENCE: 103

Arg Ser Leu Leu Arg Ser His Tyr Arg Glu Val Leu Pro Leu Ala Thr
1               5                   10                  15

Phe Val Arg Arg
            20

<210> SEQ ID NO 104
<211> LENGTH: 20
<212> TYPE: PRT
<213> ORGANISM: Homo sapiens

<400> SEQUENCE: 104

Leu Gly Pro Gln Gly Trp Arg Leu Val Gln Arg Gly Asp Pro Ala Ala
1               5                   10                  15

Phe Arg Ala Leu
            20

<210> SEQ ID NO 105
<211> LENGTH: 20
<212> TYPE: PRT
<213> ORGANISM: Homo sapiens

<400> SEQUENCE: 105

Val Ala Gln Cys Leu Val Cys Val Pro Trp Asp Ala Arg Pro Pro Pro
1               5                   10                  15

Ala Ala Pro Ser
            20

<210> SEQ ID NO 106
<211> LENGTH: 20
<212> TYPE: PRT
```

<213> ORGANISM: Homo sapiens

<400> SEQUENCE: 106

Phe Arg Gln Val Ser Cys Leu Lys Glu Leu Val Ala Arg Val Leu Gln
1               5                   10                  15

Arg Leu Cys Glu
            20

<210> SEQ ID NO 107
<211> LENGTH: 20
<212> TYPE: PRT
<213> ORGANISM: Homo sapiens

<400> SEQUENCE: 107

Arg Gly Ala Lys Asn Val Leu Ala Phe Gly Phe Ala Leu Leu Asp Gly
1               5                   10                  15

Ala Arg Gly Gly
            20

<210> SEQ ID NO 108
<211> LENGTH: 20
<212> TYPE: PRT
<213> ORGANISM: Homo sapiens

<400> SEQUENCE: 108

Pro Pro Glu Ala Phe Thr Thr Ser Val Arg Ser Tyr Leu Pro Asn Thr
1               5                   10                  15

Val Thr Asp Ala
            20

<210> SEQ ID NO 109
<211> LENGTH: 20
<212> TYPE: PRT
<213> ORGANISM: Homo sapiens

<400> SEQUENCE: 109

Leu Arg Gly Ser Gly Ala Trp Gly Leu Leu Arg Arg Val Gly Asp
1               5                   10                  15

Asp Val Leu Val
            20

<210> SEQ ID NO 110
<211> LENGTH: 20
<212> TYPE: PRT
<213> ORGANISM: Homo sapiens

<400> SEQUENCE: 110

His Leu Leu Ala Arg Cys Ala Leu Phe Val Leu Val Ala Pro Ser Cys
1               5                   10                  15

Ala Tyr Gln Val
            20

<210> SEQ ID NO 111
<211> LENGTH: 20
<212> TYPE: PRT
<213> ORGANISM: Homo sapiens

<400> SEQUENCE: 111

Cys Gly Pro Pro Leu Tyr Gln Leu Gly Ala Ala Thr Gln Ala Arg Pro
1               5                   10                  15

Pro Pro His Ala
            20

<210> SEQ ID NO 112
<211> LENGTH: 20
<212> TYPE: PRT
<213> ORGANISM: Homo sapiens

<400> SEQUENCE: 112

Ser Gly Pro Arg Arg Leu Gly Cys Glu Arg Ala Trp Asn His Ser
1               5                   10                  15

Val Arg Glu Ala
            20

<210> SEQ ID NO 113
<211> LENGTH: 20
<212> TYPE: PRT
<213> ORGANISM: Homo sapiens

<400> SEQUENCE: 113

Gly Val Pro Leu Gly Leu Pro Ala Pro Gly Ala Arg Arg Gly Gly
1               5                   10                  15

Ser Ala Ser Arg
            20

<210> SEQ ID NO 114
<211> LENGTH: 20
<212> TYPE: PRT
<213> ORGANISM: Homo sapiens

<400> SEQUENCE: 114

Ser Leu Pro Leu Pro Lys Arg Pro Arg Arg Gly Ala Ala Pro Glu Pro
1               5                   10                  15

Glu Arg Thr Pro
            20

<210> SEQ ID NO 115
<211> LENGTH: 20
<212> TYPE: PRT
<213> ORGANISM: Homo sapiens

<400> SEQUENCE: 115

Val Gly Gln Gly Ser Trp Ala His Pro Gly Arg Thr Arg Gly Pro Ser
1               5                   10                  15

Asp Arg Gly Phe
            20

<210> SEQ ID NO 116
<211> LENGTH: 20
<212> TYPE: PRT
<213> ORGANISM: Homo sapiens

<400> SEQUENCE: 116

Cys Val Val Ser Pro Ala Arg Pro Ala Glu Glu Ala Thr Ser Leu Glu
1               5                   10                  15

Gly Ala Leu Ser
            20

<210> SEQ ID NO 117
<211> LENGTH: 20
<212> TYPE: PRT
<213> ORGANISM: Homo sapiens

<400> SEQUENCE: 117

```
Gly Thr Arg His Ser His Pro Ser Val Gly Arg Gln His His Ala Gly
1               5                   10                  15

Pro Pro Ser Thr
            20

<210> SEQ ID NO 118
<211> LENGTH: 20
<212> TYPE: PRT
<213> ORGANISM: Homo sapiens

<400> SEQUENCE: 118

Ser Arg Pro Pro Arg Pro Trp Asp Thr Pro Cys Pro Pro Val Tyr Ala
1               5                   10                  15

Glu Thr Lys His
            20

<210> SEQ ID NO 119
<211> LENGTH: 20
<212> TYPE: PRT
<213> ORGANISM: Homo sapiens

<400> SEQUENCE: 119

Phe Leu Tyr Ser Ser Gly Asp Lys Glu Gln Leu Arg Pro Ser Phe Leu
1               5                   10                  15

Leu Ser Ser Leu
            20

<210> SEQ ID NO 120
<211> LENGTH: 20
<212> TYPE: PRT
<213> ORGANISM: Homo sapiens

<400> SEQUENCE: 120

Arg Pro Ser Leu Thr Gly Ala Arg Arg Leu Val Glu Thr Ile Phe Leu
1               5                   10                  15

Gly Ser Arg Pro
            20

<210> SEQ ID NO 121
<211> LENGTH: 20
<212> TYPE: PRT
<213> ORGANISM: Homo sapiens

<400> SEQUENCE: 121

Trp Met Pro Gly Thr Pro Arg Arg Leu Pro Arg Leu Pro Gln Arg Tyr
1               5                   10                  15

Trp Gln Met Arg
            20

<210> SEQ ID NO 122
<211> LENGTH: 20
<212> TYPE: PRT
<213> ORGANISM: Homo sapiens

<400> SEQUENCE: 122

Pro Leu Phe Leu Glu Leu Leu Gly Asn His Ala Gln Cys Pro Tyr Gly
1               5                   10                  15

Val Leu Leu Lys
            20

<210> SEQ ID NO 123
<211> LENGTH: 20
```

```
<212> TYPE: PRT
<213> ORGANISM: Homo sapiens

<400> SEQUENCE: 123

Thr His Cys Pro Leu Arg Ala Ala Val Thr Pro Ala Ala Gly Val Cys
1               5                   10                  15

Ala Arg Glu Lys
            20

<210> SEQ ID NO 124
<211> LENGTH: 20
<212> TYPE: PRT
<213> ORGANISM: Homo sapiens

<400> SEQUENCE: 124

Pro Gln Gly Ser Val Ala Ala Pro Glu Glu Asp Thr Asp Pro Arg
1               5                   10                  15

Arg Leu Val Gln
            20

<210> SEQ ID NO 125
<211> LENGTH: 20
<212> TYPE: PRT
<213> ORGANISM: Homo sapiens

<400> SEQUENCE: 125

Leu Leu Arg Gln His Ser Ser Pro Trp Gln Val Tyr Gly Phe Val Arg
1               5                   10                  15

Ala Cys Leu Arg
            20

<210> SEQ ID NO 126
<211> LENGTH: 20
<212> TYPE: PRT
<213> ORGANISM: Homo sapiens

<400> SEQUENCE: 126

Arg Leu Val Pro Pro Gly Leu Trp Gly Ser Arg His Asn Glu Arg Arg
1               5                   10                  15

Phe Leu Arg Asn
            20

<210> SEQ ID NO 127
<211> LENGTH: 20
<212> TYPE: PRT
<213> ORGANISM: Homo sapiens

<400> SEQUENCE: 127

Thr Lys Lys Phe Ile Ser Leu Gly Lys His Ala Lys Leu Ser Leu Gln
1               5                   10                  15

Glu Leu Thr Trp
            20

<210> SEQ ID NO 128
<211> LENGTH: 20
<212> TYPE: PRT
<213> ORGANISM: Homo sapiens

<400> SEQUENCE: 128

Lys Met Ser Val Arg Asp Cys Ala Trp Leu Arg Arg Ser Pro Gly Val
1               5                   10                  15

Gly Cys Val Pro
```

20

<210> SEQ ID NO 129
<211> LENGTH: 20
<212> TYPE: PRT
<213> ORGANISM: Homo sapiens

<400> SEQUENCE: 129

Ala Ala Glu His Arg Leu Arg Glu Glu Ile Leu Ala Lys Phe Leu His
1               5                   10                  15

Trp Leu Met Ser
            20

<210> SEQ ID NO 130
<211> LENGTH: 20
<212> TYPE: PRT
<213> ORGANISM: Homo sapiens

<400> SEQUENCE: 130

Val Tyr Val Val Glu Leu Leu Arg Ser Phe Phe Tyr Val Thr Glu Thr
1               5                   10                  15

Thr Phe Gln Lys
            20

<210> SEQ ID NO 131
<211> LENGTH: 20
<212> TYPE: PRT
<213> ORGANISM: Homo sapiens

<400> SEQUENCE: 131

Asn Arg Leu Phe Phe Tyr Arg Lys Ser Val Trp Ser Lys Leu Gln Ser
1               5                   10                  15

Ile Gly Ile Arg
            20

<210> SEQ ID NO 132
<211> LENGTH: 20
<212> TYPE: PRT
<213> ORGANISM: Homo sapiens

<400> SEQUENCE: 132

Gln His Leu Lys Arg Val Gln Leu Arg Glu Leu Ser Glu Ala Glu Val
1               5                   10                  15

Arg Gln His Arg
            20

<210> SEQ ID NO 133
<211> LENGTH: 20
<212> TYPE: PRT
<213> ORGANISM: Homo sapiens

<400> SEQUENCE: 133

Glu Ala Arg Pro Ala Leu Leu Thr Ser Arg Leu Arg Phe Ile Pro Lys
1               5                   10                  15

Pro Asp Gly Leu
            20

<210> SEQ ID NO 134
<211> LENGTH: 20
<212> TYPE: PRT
<213> ORGANISM: Homo sapiens

<400> SEQUENCE: 134

```
Arg Pro Ile Val Asn Met Asp Tyr Val Val Gly Ala Arg Thr Phe Arg
1               5                   10                  15

Arg Glu Lys Arg
            20

<210> SEQ ID NO 135
<211> LENGTH: 20
<212> TYPE: PRT
<213> ORGANISM: Homo sapiens

<400> SEQUENCE: 135

Ala Glu Arg Leu Thr Ser Arg Val Lys Ala Leu Phe Ser Val Leu Asn
1               5                   10                  15

Tyr Glu Arg Ala
            20

<210> SEQ ID NO 136
<211> LENGTH: 20
<212> TYPE: PRT
<213> ORGANISM: Homo sapiens

<400> SEQUENCE: 136

Arg Arg Pro Gly Leu Leu Gly Ala Ser Val Leu Gly Leu Asp Asp Ile
1               5                   10                  15

His Arg Ala Trp
            20

<210> SEQ ID NO 137
<211> LENGTH: 20
<212> TYPE: PRT
<213> ORGANISM: Homo sapiens

<400> SEQUENCE: 137

Arg Thr Phe Val Leu Arg Val Arg Ala Gln Asp Pro Pro Glu Leu
1               5                   10                  15

Tyr Phe Val Lys
            20

<210> SEQ ID NO 138
<211> LENGTH: 20
<212> TYPE: PRT
<213> ORGANISM: Homo sapiens

<400> SEQUENCE: 138

Val Asp Val Thr Gly Ala Tyr Asp Thr Ile Pro Gln Asp Arg Leu Thr
1               5                   10                  15

Glu Val Ile Ala
            20

<210> SEQ ID NO 139
<211> LENGTH: 20
<212> TYPE: PRT
<213> ORGANISM: Homo sapiens

<400> SEQUENCE: 139

Ala His Gly His Val Arg Lys Ala Phe Lys Ser His Val Ser Thr Leu
1               5                   10                  15

Thr Asp Leu Gln
            20

<210> SEQ ID NO 140
```

```
<211> LENGTH: 20
<212> TYPE: PRT
<213> ORGANISM: Homo sapiens

<400> SEQUENCE: 140

Pro Tyr Met Arg Gln Phe Val Ala His Leu Gln Glu Thr Ser Pro Leu
1               5                   10                  15

Arg Asp Ala Val
            20

<210> SEQ ID NO 141
<211> LENGTH: 20
<212> TYPE: PRT
<213> ORGANISM: Homo sapiens

<400> SEQUENCE: 141

Val Ile Glu Gln Ser Ser Ser Leu Asn Glu Ala Ser Ser Gly Leu Phe
1               5                   10                  15

Asp Val Phe Leu
            20

<210> SEQ ID NO 142
<211> LENGTH: 20
<212> TYPE: PRT
<213> ORGANISM: Homo sapiens

<400> SEQUENCE: 142

Arg Phe Met Cys His His Ala Val Arg Ile Arg Gly Lys Ser Tyr Val
1               5                   10                  15

Gln Cys Gln Gly
            20

<210> SEQ ID NO 143
<211> LENGTH: 20
<212> TYPE: PRT
<213> ORGANISM: Homo sapiens

<400> SEQUENCE: 143

Ile Pro Gln Gly Ser Ile Leu Ser Thr Leu Leu Cys Ser Leu Cys Tyr
1               5                   10                  15

Gly Asp Met Glu
            20

<210> SEQ ID NO 144
<211> LENGTH: 20
<212> TYPE: PRT
<213> ORGANISM: Homo sapiens

<400> SEQUENCE: 144

Asn Lys Leu Phe Ala Gly Ile Arg Arg Asp Gly Leu Leu Leu Arg Leu
1               5                   10                  15

Val Asp Asp Phe
            20

<210> SEQ ID NO 145
<211> LENGTH: 20
<212> TYPE: PRT
<213> ORGANISM: Homo sapiens

<400> SEQUENCE: 145

Leu Leu Val Thr Pro His Leu Thr His Ala Lys Thr Phe Leu Arg Thr
1               5                   10                  15
```

```
Leu Val Arg Gly
            20

<210> SEQ ID NO 146
<211> LENGTH: 20
<212> TYPE: PRT
<213> ORGANISM: Homo sapiens

<400> SEQUENCE: 146

Val Pro Glu Tyr Gly Cys Val Val Asn Leu Arg Lys Thr Val Val Asn
1               5                   10                  15

Phe Pro Val Glu
            20

<210> SEQ ID NO 147
<211> LENGTH: 20
<212> TYPE: PRT
<213> ORGANISM: Homo sapiens

<400> SEQUENCE: 147

Asp Glu Ala Leu Gly Gly Thr Ala Phe Val Gln Met Pro Ala His Gly
1               5                   10                  15

Leu Phe Pro Trp
            20

<210> SEQ ID NO 148
<211> LENGTH: 20
<212> TYPE: PRT
<213> ORGANISM: Homo sapiens

<400> SEQUENCE: 148

Cys Gly Leu Leu Leu Asp Thr Arg Thr Leu Glu Val Gln Ser Asp Tyr
1               5                   10                  15

Ser Ser Tyr Ala
            20

<210> SEQ ID NO 149
<211> LENGTH: 20
<212> TYPE: PRT
<213> ORGANISM: Homo sapiens

<400> SEQUENCE: 149

Arg Arg Lys Leu Phe Gly Val Leu Arg Leu Lys Cys His Ser Leu Phe
1               5                   10                  15

Leu Asp Leu Gln
            20

<210> SEQ ID NO 150
<211> LENGTH: 20
<212> TYPE: PRT
<213> ORGANISM: Homo sapiens

<400> SEQUENCE: 150

Val Asn Ser Leu Gln Thr Val Cys Thr Asn Ile Tyr Lys Ile Leu Leu
1               5                   10                  15

Leu Gln Ala Tyr
            20

<210> SEQ ID NO 151
<211> LENGTH: 20
<212> TYPE: PRT
<213> ORGANISM: Homo sapiens
```

```
<400> SEQUENCE: 151

Arg Phe His Ala Cys Val Leu Gln Leu Pro Phe His Gln Gln Val Trp
1               5                   10                  15

Lys Asn Pro Thr
            20

<210> SEQ ID NO 152
<211> LENGTH: 20
<212> TYPE: PRT
<213> ORGANISM: Homo sapiens

<400> SEQUENCE: 152

Phe Phe Leu Arg Val Ile Ser Asp Thr Ala Ser Leu Cys Tyr Ser Ile
1               5                   10                  15

Leu Lys Ala Lys
            20

<210> SEQ ID NO 153
<211> LENGTH: 20
<212> TYPE: PRT
<213> ORGANISM: Homo sapiens

<400> SEQUENCE: 153

Asn Ala Gly Met Ser Leu Gly Ala Lys Gly Ala Ala Gly Pro Leu Pro
1               5                   10                  15

Ser Glu Ala Val
            20

<210> SEQ ID NO 154
<211> LENGTH: 20
<212> TYPE: PRT
<213> ORGANISM: Homo sapiens

<400> SEQUENCE: 154

Gln Trp Leu Cys His Gln Ala Phe Leu Leu Lys Leu Thr Arg His Arg
1               5                   10                  15

Val Thr Tyr Val
            20

<210> SEQ ID NO 155
<211> LENGTH: 20
<212> TYPE: PRT
<213> ORGANISM: Homo sapiens

<400> SEQUENCE: 155

Pro Leu Leu Gly Ser Leu Arg Thr Ala Gln Thr Gln Leu Ser Arg Lys
1               5                   10                  15

Leu Pro Gly Thr
            20

<210> SEQ ID NO 156
<211> LENGTH: 22
<212> TYPE: PRT
<213> ORGANISM: Homo sapiens

<400> SEQUENCE: 156

Thr Leu Thr Ala Leu Glu Ala Ala Ala Asn Pro Ala Leu Pro Ser Asp
1               5                   10                  15

Phe Lys Thr Ile Leu Asp
            20
```

<210> SEQ ID NO 157
<211> LENGTH: 1132
<212> TYPE: PRT
<213> ORGANISM: Homo sapiens

<400> SEQUENCE: 157

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

-continued

```
Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
            405                 410                 415

Ala Ala Val Thr Pro Ala Ala Gly Val Cys Ala Arg Glu Lys Pro Gln
        420                 425                 430

Gly Ser Val Ala Ala Pro Glu Glu Asp Thr Asp Pro Arg Arg Leu
    435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
            485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
        530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro Pro
            690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
        770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
```

```
                    805                 810                 815
Ala Val Arg Ile Arg Gly Lys Ser Tyr Val Gln Cys Gln Gly Ile Pro
            820                 825                 830

Gln Gly Ser Ile Leu Ser Thr Leu Cys Ser Leu Cys Tyr Gly Asp
        835                 840                 845

Met Glu Asn Lys Leu Phe Ala Gly Ile Arg Arg Asp Gly Leu Leu
    850                 855                 860

Arg Leu Val Asp Asp Phe Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln Gln
    1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
                1045                1050                1055

Gly Ala Lys Gly Ala Ala Gly Pro Leu Pro Ser Glu Ala Val Gln Trp
            1060                1065                1070

Leu Cys His Gln Ala Phe Leu Leu Lys Leu Thr Arg His Arg Val Thr
        1075                1080                1085

Tyr Val Pro Leu Leu Gly Ser Leu Arg Thr Ala Gln Thr Gln Leu Ser
    1090                1095                1100

Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
                1125                1130

<210> SEQ ID NO 158
<211> LENGTH: 239
<212> TYPE: PRT
<213> ORGANISM: Artificial Sequence
<220> FEATURE:
<223> OTHER INFORMATION: Green Fluorescent Protein

<400> SEQUENCE: 158

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
```

```
            35                  40                  45
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 159
<211> LENGTH: 720
<212> TYPE: DNA
<213> ORGANISM: Artificial Sequence
<220> FEATURE:
<223> OTHER INFORMATION: Green Fluorescent Protein

<400> SEQUENCE: 159
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720

<210> SEQ ID NO 160
<211> LENGTH: 21
<212> TYPE: RNA
<213> ORGANISM: Artificial Sequence
<220> FEATURE:
<223> OTHER INFORMATION: siRNA sense
```

```
<220> FEATURE:
<221> NAME/KEY: variation
<222> LOCATION: (20)..(21)
<223> OTHER INFORMATION: n is deoxythymidine (dT)

<400> SEQUENCE: 160
cuuacgcuga guacuucgan n                                              21

<210> SEQ ID NO 161
<211> LENGTH: 21
<212> TYPE: RNA
<213> ORGANISM: Artificial Sequence
<220> FEATURE:
<223> OTHER INFORMATION: siRNA antisense
<220> FEATURE:
<221> NAME/KEY: variation
<222> LOCATION: (20)..(21)
<223> OTHER INFORMATION: n is deoxythymidine (dT)

<400> SEQUENCE: 161
ucgaaguacu cagcguaagn n                                              21

<210> SEQ ID NO 162
<211> LENGTH: 21
<212> TYPE: RNA
<213> ORGANISM: Artificial Sequence
<220> FEATURE:
<223> OTHER INFORMATION: siCont sense
<220> FEATURE:
<221> NAME/KEY: variation
<222> LOCATION: (20)..(21)
<223> OTHER INFORMATION: n is deoxythymidine (dT)

<400> SEQUENCE: 162
gcaccuauaa caacgguagn n                                              21

<210> SEQ ID NO 163
<211> LENGTH: 21
<212> TYPE: RNA
<213> ORGANISM: Artificial Sequence
<220> FEATURE:
<223> OTHER INFORMATION: siCont antisense
<220> FEATURE:
<221> NAME/KEY: variation
<222> LOCATION: (20)..(21)
<223> OTHER INFORMATION: n is deoxythymidine (dT)

<400> SEQUENCE: 163
cuaccguugu uauaggugcn n                                              21

<210> SEQ ID NO 164
<211> LENGTH: 16
<212> TYPE: PRT
<213> ORGANISM: Homo sapiens

<400> SEQUENCE: 164

Glu Ala Arg Pro Ala Leu Leu Thr Ser Arg Leu Arg Phe Ile Pro Lys
1               5                   10                  15
```